US012698531B2

(12) United States Patent
Pirruccello et al.

(10) Patent No.: US 12,698,531 B2
(45) Date of Patent: Aug. 4, 2026

(54) METHODS OF PREDICTING ANEURYSMS OF THE ASCENDING AND DESCENDING AORTA

(71) Applicant: The General Hospital Corporation, Boston, MA (US)

(72) Inventors: James P. Pirruccello, Boston, MA (US); Patrick T. Ellinor, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 805 days.

(21) Appl. No.: 17/923,845

(22) PCT Filed: May 7, 2021

(86) PCT No.: PCT/US2021/031329
§ 371 (c)(1),
(2) Date: Nov. 7, 2022

(87) PCT Pub. No.: WO2021/226481
PCT Pub. Date: Nov. 11, 2021

(65) Prior Publication Data
US 2023/0203584 A1     Jun. 29, 2023

Related U.S. Application Data

(60) Provisional application No. 63/105,785, filed on Oct. 26, 2020, provisional application No. 63/105,189, filed on Oct. 23, 2020, provisional application No. 63/022,400, filed on May 8, 2020.

(51) Int. Cl.
*C12Q 1/68*      (2018.01)
*C12P 19/34*      (2006.01)
*C12Q 1/6883*      (2018.01)
*C12Q 1/6869*      (2018.01)

(52) U.S. Cl.
CPC ......... *C12Q 1/6883* (2013.01); *C12Q 1/6869* (2013.01); *C12Q 2600/118* (2013.01); *C12Q 2600/156* (2013.01)

(58) Field of Classification Search
None
See application file for complete search history.

(56) References Cited

FOREIGN PATENT DOCUMENTS

EP          2592157  A1      5/2013

OTHER PUBLICATIONS

Seamus C. Harrison, et al. "A gene-centric study of common carotid artery remodelling" Atherosclerosis, vol. 226, Issue 2, Feb. 2013, pp. 440-446 (Year: 2013).*
Submitted SNP(ss) Details: ss76695960 (Aug. 28, 2007), Submitter SNP ID AFFY_6_1M_SNP_A-8557279, RefSNP(rs#) rs1441358, from www.ncbi.nlm.nih.gov/projects/SNP (Year: 2007).*
Jack Lucentini ,"Gene Association Studies Typically Wrong" The Scientist, Dec. 20, 2004, p. 20. (Year: 2004).*
H. Juppner, "Functional Properties of the PTH/PTHrP Receptor" Bone vol. 17, No. 2, Supplement, Aug. 1995:39S-42S (Year: 1995).*
Wolfgang Enard, et al. "Intra- and Interspecific Variation in Primate Gene Expression Patterns" Science, vol. 296, Apr. 12, 2002, pp. 340-343. (Year: 2002).*
Elizabeth Pennisi, "A closer look at SNPs suggests difficulties" Science; Sep. 18, 1998; 281, 5384, p. 1787-1789. (Year: 1998).*
Vivian G. Cheung, et al. "Natural variation in human gene expression assessed in lymphoblastoid cells" Nature Genetics, vol. 33, Mar. 2003, pp. 422-425. (Year: 2003).*
Advic, Tarik , "Reduced Long-Term Risk of Aortic Aneurysm and Aortic Dissection Among Individuals With Type 2 Diabetes Mellitus: A Nationwide Observational Study", Journal of the American Heart Association, 2018, 18 pages.
Balistreri, Carmela Rita, "Genetic contribution in sporadic thoracic aortic aneurysm? Emerging evidence of genetic variants related to TLR-4-mediated signaling pathway as risk determinants", Vascular Pharmacology, vol. 74, pp. 1-10, Nov. 2015.
Bellenguez, Celine , "A robust clustering algorithm for identifying problematic samples in genome-wide association studies", Bioinformatics, Genetics and population analysis, vol. 28 No. 1, Nov. 3, 2011, 2 pages.
Benjamin, Emelia J, "Heart Disease and Stroke Statistics—2019 Update", <4 of 5> American Heart Association, Mar. 5, 2019, 94 pages.
Benjamin, Emelia J, "Heart Disease and Stroke Statistics—2019 Update", <5 of 5> American Heart Association, Mar. 5, 2019, 94 pages.
Benjamin, Emelia J, "Heart Disease and Stroke Statistics- 2019 Update", <1 of 5> American Heart Association, Mar. 5, 2019, 95 pages.
Benjamin, Emelia J, "Heart Disease and Stroke Statistics- 2019 Update", <2 of 5> American Heart Association, Mar. 5, 2019, 95 pages.

(Continued)

*Primary Examiner* — Stephen T Kapushoc
(74) *Attorney, Agent, or Firm* — FIG. 1 Patents

(57) ABSTRACT

The disclosure provides methods of assessing a subject's risk of ascending thoracic aortic aneurysm or descending thoracic aortic aneurysm by detecting one or more single nucleotide polymorphisms (SNP) in one or more specific genes. The disclosure also provides methods of calculating a polygenic score to assess a subjects risk. Such methods may be used, for example, to identify asymptomatic subjects at risk for aneurysm.

9 Claims, 32 Drawing Sheets

Specification includes a Sequence Listing.

(56)             References Cited

OTHER PUBLICATIONS

Benjamin, Emelia J, "Heart Disease and Stroke Statistics—2019 Update", <3 of 5> American Heart Association, Mar. 5, 2019, 95 pages.

Benjamin, Emelia J., "Variants in ZFHX3 are associated with atrial fibrillation in individuals of European ancestry", Nat Genet. Author manuscript; available in PMC, Feb. 1, 2010, 10 pages.

Bhuwania, Ridhirama , "Supervillin couples myosin-dependent contractility to podosomes and enables their turnover", Journal of Cell Science, The Company of Biologists Ltd, Jan. 5, 2012, 15 pages.

Bradley, Timothy , "The Expanding Clinical Spectrum of Extracardiovascular and Cardiovascular Manifestations of Heritable Thoracic Aortic Aneurysm and Dissection", Canadian Journal of Cardiology 32, Elsevier, 2016, 14 pages.

Bulik-Sullivan, Brendan , "An Atlas of Genetic Correlations across Human Diseases and Traits", Nat Genet., PMC, May 1, 2016, 22 pages.

Bulik-Sullivan, Brendan K, "LD Score Regression Distinguishes Confounding from Polygenicity in Genome-Wide Association Studies", Nat Genet. Author manuscript; available in PMC, Sep. 1, 2015, 21 pages.

Bycroft, Clare , "The UK Biobank resource with deep phenotyping and genomic data", Nature, vol. 562, Springer, Oct. 11, 2018, 25 pages.

Campens, Laurence , "Reference Values for Echocardiographic Assessment of the Diameter of the Aortic Root and Ascending Aorta Spanning All Age Categories", , 21 pages.

Chang, Christopher C., "Second-generation PLINK: rising to the challenge of larger and richer datasets", GIGA Science, BioMed Central, 2015, 16 pages.

Chen, Huimei , "WWP2 regulates pathological cardiac fibrosis by modulating SMAD2 signaling", Nature Communications, 2019, 19 pages.

Chen, Li , "A single nucleotide polymorphism in the matrix metalloproteinase 9 gene (-8202A/G) is associated with thoracic aortic aneurysms and thoracic aortic dissection", The Journal of Thoracic and Cardiovascular Surgery, vol. 131, No. 5,, May 2006, 8 pages.

Chou, Chon-Kit , "The Regulations of Deubiquitinase USP15 and Its Pathophysiological Mechanisms in Diseases", International Journal of Molecular Sciences, MDPI, 2017, 15 pages.

Das, Sayantan , "Next-generation genotype imputation service and methods", Nat Genet. Author manuscript; available in PMC, Oct. 1, 2017, 15 pages.

De Leeuw, Christiaan , "MAGMA: Generalized Gene-Set Analysis of GWAS Data", PLOS Computational Biology, Apr. 17, 2015, 19 pages.

Deng, Jia , "ImageNet: A Large-Scale Hierarchical Image Database", In Proceedings of IEEE Conference on Computer Vision and Pattern Recognition [retrieved Jun. 14, 2023]. Retrieved from the Internet <https://www-cs-faculty.stanford.edu/groups/vision/documents/ImageNet_CVPR2009.pdf>., Jun. 20, 2009, 8 pages.

Dietz, Harry C, "Marfan syndrome caused by a recurrent de novo missense mutation in the fibrillin gene", Nature, vol. 352, Jul. 25, 1991, 3 pages.

Eichhorn, Pieter J A, "USP15 stabilizes TGF-β receptor I and promotes oncogenesis through the activation of TGF-β signaling in glioblastoma", nature medicine, vol. 18, No. 3, Mar. 2012, 8 pages.

Elbitar, Sandy , "Pathogenic variants in THSD4, encoding the ADAMTS-like 6 protein, predispose to inherited thoracic aortic aneurysm", Genetics in Medicine, vol. 23, No. 1, Jan. 2021, 12 pages.

Elefteriades, John A, "Thoracic Aortic Aneurysm Clinically Pertinent Controversies and Uncertainties", Journal of the American College of Cardiology, vol. 55, No. 9, Mar. 2010, 17 pages.

Elefteriades, John A, "Thoracic Aortic Aneurysm: Clinically Pertinent Controversies and Uncertainties", Journal of the American College of Cardiology, vol. 55, No. 9, pp. 841-857, Mar. 2010, 31 pages.

Falak, Samreen , "Protease inhibitor 15, a candidate gene for abdominal aortic internal elastic lamina ruptures in the rat", Articles in PresS. Physiol Genomics, May 1, 2014, 25 pages.

Fann, James I, "Descending thoracic and thoracoabdominal aortic aneurysms", Coronary Artery Disease, vol. 13 No 2, 2002, 10 pages.

Finucane, Hilary K., "Heritability enrichment of specifically expressed genes identifies disease- relevant tissues and cell types", Nat Genet. Author manuscript; available in PMC, Apr. 2018, 30 pages.

Fleming, Stephen J, "Unsupervised removal of systematic background noise from droplet-based single- cell experiments using CellBender", bioRxiv preprint doi: https://doi.org/10.1101/791699, Jul. 12, 2022, 63 pages.

Gamazon, Eric R., "A gene-based association method for mapping traits using reference transcriptome data", Nat Genet. Author manuscript; available in PMC, Mar. 1, 2016, 28 pages.

GitHub , "benmarwick / cvequality", retrieved from <<https://github.com/benmarwick/cvequality>> on Jun. 9, 2025, Jan. 5, 2019, 4 pages.

Guo, Dong-Chong , "Pathogenesis of Thoracic and Abdominal Aortic Aneurysms", Annals New York Academy of Sciences, 2006, 14 pages.

Guo, Dong-chuan , "Genetic Variants in LRP1 and ULK4 Are Associated with Acute Aortic Dissections", The American Journal of Human Genetics, Sep. 1, 2016, 13 pages.

Gusev, Alexander , "Integrative approaches for large-scale transcriptome-wide association studies", Nat Genet. Author manuscript; available in PMC, Mar. 1, 2017, 27 pages.

Gusev, Alexander , "Transcriptome-wide association study of schizophrenia and chromatin activity yields mechanistic disease insights", Nat Genet. Author manuscript; available in PMC, Oct. 9, 2018, 32 pages.

Haas, Mary E., "Genetic Association of Albuminuria with Cardiometabolic Disease and Blood Pressure", The American Journal of Human Genetics, Oct. 4, 2018, 37 pages.

Hagan, Peter G, "The International Registry of Acute Aortic Dissection (IRAD)", American Medical Association, New Insights Into an Old Disease, Feb. 16, 2000, 7 pages.

He, Kaiming , "Deep Residual Learning for Image Recognition", Cornell University arXiv Preprint, arXiv.org [retrieved Aug. 11, 2023]. Retrieved from the Internet <https://arxiv.org/pdf/1512.03385.pdf>., Dec. 10, 2015, 12 pages.

He, Kaiming , "Spatial Pyramid Pooling in Deep Convolutional Networks for Visual Recognition", , Apr. 23, 2015, 14 pages.

Heuze, Melina L., "ASB2 targets filaminsAand B to proteasomal degradation", Blood, vol. 112, No. 13, The American Society of Hematology, Dec. 15, 2008, 11 pages.

Hof, Femke , "Shared Genetic Risk Factors of Intracranial, Abdominal, and Thoracic Aneurysms", Journal of the American Heart Association, Mar. 16, 2016, 19 pages.

Hong, Huixiao , "Assessing batch effects of genotype calling algorithm BRLMM for the Affymetrix GeneChip Human Mapping 500 K array set using 270 HapMap samples", BMC Bioinformatics, BioMed Central, Aug. 12, 2008, 13 pages.

Howard, Jeremy , "Fastai: A Layered API for Deep Learning", MDPI, Information 2020, 2020, 26 pages.

Iakoubova, Olga A, "Genetic Variants in FBN-1 and Risk for Thoracic Aortic Aneurysm and Dissection", Plos One, vol. 9, No. 4, Apr. 2014, 5 pages.

Isselbacker, Eric , "Thoracic and Abdominal Aortic Aneurysms", Contemporary Reviews in Cardiovascular Medicine, Aortic Center and Cardiology Division, Massachusetts General Hospital, Boston, Mass, Feb. 15, 2005, 13 pages.

Jondeau, Guillaume , "Familial thoracic aortic aneurysms", vol. 29, No. 6, Wolters Kluwer Health | Lippincott Williams & Wilkins, Nov. 2014, 7 pages.

Kaplan, Sarah , "Prevalence of an Increased Ascending and Descending Thoracic Aorta Diameter Diagnosed by Multislice Cardiac Computed Tomography in Men Versus Women and in Persons Aged 23 to 50 Years, 51 to 65 Years, 66 to 80 Years, and 81 to 88 Years", Elsevier, 2007, 2 pages.

Karczewski, Konrad , "Variation across 141,456 human exomes and genomes reveals the spectrum of loss-offunction intolerance across human protein-coding genes", bioRxiv, Aug. 13, 2019, 44 pages.

(56) References Cited

OTHER PUBLICATIONS

Kechin, Andrey , "cutPrimers: A New Tool for Accurate Cutting of Primers from Reads of Targeted Next Generation Sequencing", Journal of Computational Biology, vol. 24, No. 0, Mary Ann Liebert, Inc., 2017, 6 pages.

Kent, Craig K, "Analysis of risk factors for abdominal aortic aneurysm in a cohort of more than 3 million individuals", Journal of Vascular Surgery, vol. 52, No. 3, Sep. 2010, 10 pages.

Kingman, Diederik , "ADAM: a Method for Stochastic Optimization", ICLR, 2015, 15 pages.

Krizhevsky, Alex , "ImageNet Classification with Deep Convolutional Neural Networks", In Advances in Neural Information Processing Systems 25, Dec. 3, 2012, 9 pages.

Leeuw, C.A. , "The statistical properties of gene-set analysis", Nature Reviews. Genetics, 17, 6, 2016, 13 pages.

LeMaire, Scott A, "Genome-wide association study identifies a susceptibility locus for thoracic aortic aneurysms and aortic dissections spanning FBN1 at 15q21.1", Nat Genet. Author manuscript; available in PMC, Dec. 22, 2011, 12 pages.

Liberzon, Arthur , "Molecular signatures database (MSigDB) 3.0", Bioinformatics, vol. 27 No. 12, May 5, 2011, 2 pages.

Linder, Stefan , "Degrading Devices: Invadosomes in Proteolytic Cell Invasion", Institute for Medical Microbiology, Virology and Hygiene, University Medical Center, Jul. 21, 2011, 30 pages.

Lindsay, Mark , "Lessons on the pathogenesis of aneurysm from heritable conditions", NIH Public Access, Nature, May 19, 2011, 22 pages.

Liu, Ou , "Genetic analysis of six SNPs in candidate genes associated with high cross-race risk of development of thoracic aortic aneurysms and dissections in Chinese Han population", Acta Pharmacologica Sinica, vol. 31, No. 10, pp. 1376-1380, Sep. 2010, 5 pages.

Loh, Po-Ru , "Efficient Bayesian mixed model analysis increases association power in large cohorts", Nat Genet. Author manuscript; available in PMC, Sep. 1, 2015, 24 pages.

Loh, Po-Ru , "Mixed model association for biobank-scale data sets", Nat Genet. Author manuscript; available in PMC, Jan. 1, 2019, 6 pages.

Lonsdale, J , "The Genotype-Tissue Expression (GTEx) project", Nat Genet 45, (2013) https://doi.org.1038/ng.2653, Jun. 1, 2013, 5 pages.

Lopez, Romain , "Deep Generative Modeling for Single-cell Transcriptomics", Nat Methods. Author manuscript; available in PMC, May 30, 2019, 21 pages.

Love, Michael , "Moderated estimation of fold change and dispersion for RNA-seq data with DESeq2", Genome Biology, BioMed, 2014, 21 pages.

Lun, Aaron T.L., "Overcoming confounding plate effects in differential expression analyses of single-cell RNA-seq data", bioRxin, Sep. 8, 2016, 14 pages.

Maddika, Subbareddy , "WWP2 is an E3 ubiquitin ligase for PTEN", Nat Cell Biol. Author manuscript; available in PMC, Feb. 17, 2014, 15 pages.

Majesky, Mark W, "Developmental Basis of Vascular Smooth Muscle Diversity", Arterioscler Thromb Vasc Biol., Origins of Smooth Muscle Diversity, American Heart Association, Inc., Jun. 2007, 11 Pages.

Mchugh, Mary L., "Interrater reliability: the kappa statistic", Department of Nursing, National University, Biochemia Medica, Aug. 29, 2012, 7 pages.

Mcinnes, Leland , "UMAP: Uniform Manifold Approximation and Projection for Dimension Reduction", , Sep. 21, 2020, 63 pages.

McLaren, William , "The Ensembl Variant Effect Predictor", Genome Biology, BioMed Central, 2016, 14 pages.

Owens, Douglas , "Screening for Abdominal Aortic Aneurysm US Preventive Services Task Force Recommendation Statement", JAMA, vol. 322, No. 22, doi:10.1001/jama.2019.18928, Dec. 10, 2019, 8 pages.

Parolari, Alessandro , "Biological features of thoracic aortic diseases. Where are we now, where are we heading to: established and emerging biomarkers and molecular pathways", European Journal of Cardio-Thoracic Surgery, vol. 44, No. 1, Jan. 2013, 15 pages.

Parrot, Ashley , "Cantu syndrome: A longitudinal review of vascular findings in three individuals", American Journal of medical genetics, Part A Wiley, Jan. 23, 2020, 6 pages.

PCT/US2021/031329 , "International Search Report and Written Opinion", PCT Application No. PCT/US2021/031329, Oct. 7, 2021, 18 pages.

PCT/US2021/031329 , "Invitation to Pay Additional Fees and, Where Applicable, Protest Fee", PCT Application No. PCT/US2021/031329, Aug. 11, 2021, 13 pages.

Pers, Tune H., "SNPsnap: a Web-based tool for identification and annotation of matched SNPs", Bioinformatics, vol. 31 No. 3, Oct. 13, 2014, 3 pages.

Petersen, Steffen , "UK Biobank's cardiovascular magnetic resonance protocol", Journal of Cardiovascular Magnetic Resonance, 2016, 7 pages.

Petersen, Steffen E., "Imaging in population science: cardiovascular magnetic resonance in 100,000 participants of UK Biobank— rationale, challenges and approaches", Journal of Cardiovascular Magnetic Resonance, 2013, 10 pages.

Pinard, Amelie , "Genetics of Thoracic and Abdominal Aortic Diseases", Aortic Aneurysms Compendium, American Heart Association, Inc., 2019, 19 pages.

Pirruccello, James , "Analysis of cardiac magnetic resonance imaging traits in 29,000 individuals reveals shared genetic basis with dilated cardiomyopathy", bioRXiv, Feb. 13, 2020, 39 pages.

Prakash, Siddharth K., "Diabetes and Reduced Risk for Thoracic Aortic Aneurysms and Dissections: A Nationwide Case-Control Study", Journal of the American Heart Association, 2012, 8 pages.

Qazi, Saadia , "Increased Aortic Diameters on Multidetector Computed Tomographic Scan Are Independent Predictors of Incident Adverse Cardiovascular Events", The Framingham Heart Study, Circ Cardiovasc Imaging, American Heart Association, Inc., 2017, 8 pages.

Regier, Allison , "Functional equivalence of genome sequencing analysis pipelines enables harmonized variant calling across human genetics projects", Nature Communications, 2019, 8 pages.

Renard, Marjolijin , "Clinical Validity of Genes for Heritable Thoracic Aortic Aneurysm and Dissection", J Am Coll Cardiol. Author manuscript; available in PMC, Feb. 18, 2019, 19 pages.

Ritchie, Matthew E., "limma powers differential expression analyses for RNA-sequencing and microarray studies", Nucleic Acids Research, 2015, vol. 43, No. 7, Jan. 20, 2015, 13 pages.

Rogers, Ian , "Distribution, Determinants, and Normal Reference Values of Thoracic and Abdominal Aortic Diameters by Computed Tomography", From the Framingham Heart Study, Am J Cardiol. Author manuscript; available in PMC, May 15, 2014, 16 pages.

Ronneberger, Olaf , "U-Net: Convolutional Networks for Biomedical Image Segmentation", Cornell University arXiv, arXiv.org [retrieved Mar. 16, 2023]. Retrieved from the Internet <https://arxiv.org/pdf/1505.04597.pdf>., May 18, 2015, 8 pages.

Rosenfeld, Azriel , "Sequential Operations in Digital Picture Processing", J. ACM, 13(4):471-494 [retrieved from the internet on Mar. 4, 2025], <https://www.cs.virginia.edu/~jlp/66.sequential.op.pdf>, 1966, 24 Pages.

Scola, Letizia , "Role of TGF-B Pathway Polymorphisms in Sporadic Thoracic Aortic Aneurysm: rs900 TGF-B2 Is a Marker of Differential Gender Susceptibility", Mediators of Inflammation, vol. 2014, No. 165758, Feb. 2014, 8 pages.

Segre, Ayellet , "Common Inherited Variation in Mitochondrial Genes Is Not Enriched for Associations with Type 2 Diabetes or Related Glycemic Traits", PLoS Genetics, vol. Issue 8, Aug. 2010, 19 pages.

Smith, Leslie N., "Cyclical Learning Rates for Training Neural Networks", U.S. Naval Research Laboratory, Code 5514, Apr. 4, 2017, 10 pages.

Smyth, Gordon K., "Use of within-array replicate spots for assessing differential expression in microarray experiments", Bioinformatics, vol. 21 No. 9, Jan. 7, 2005, 9 pages.

Stuart, Tim J, "Comprehensive integration of single cell data", bioRxiv preprint doi: http://dx.doi.org/10.1101/460147, Nov. 2, 2018, 24 pages.

(56)            References Cited

OTHER PUBLICATIONS

Sudlow, Cathie , "UK Biobank: An Open Access Resource for Identifying the Causes of a Wide Range of Complex Diseases of Middle and Old Age", PLOS medicine, Mar. 31, 2015, 10 pages.

Teslovich , "Biological, Clinical, and Population Relevance of 95 Loci for Blood Lipids", Nature. Author manuscript; available in PMC, Feb. 15, 2011, 16 pages.

Tsutsui, Ko , "ADAMTSL-6 Is a Novel Extracellular Matrix Protein That Binds to Fibrillin-1 and Promotes Fibrillin-1 Fibril Formation*", The Journal of Biological Chemistry vol. 285, No. 7, Feb. 12, 2010, 13 pages.

Turkbey, Evrim B., "Determinants and Normal Values of Ascending Aortic Diameter by Age, Gender, and Race/Ethnicity in the Multi-Ethnic Study of Atherosclerosis (MESA)", Journal of Magnetic Resonance Imaging, Wiley Periodicals, Inc., Mar. 28, 2013, 9 pages.

Van der Auwera, Geraldine A, "From FastQ data to high confidence variant calls: the Genome Analysis Toolkit best practices pipeline", National Institutes of Health, Curr Protoc Bioinformatics, Nov. 25, 2014, 43 pages.

Van Hout, Cristopher V., "Whole exome sequencing and characterization of coding variation in 49,960 individuals in the UK Biobank", bioRxiv, Mar. 9, 2019, 34 pages.

Vapnik, Joshua S., "Characteristics and Outcomes of Ascending Versus Descending Thoracic Aortic Aneurysms", The American Journal of Cardiology, 2016, 8 pages.

Vasan, Ramachandra , "Genetic Variants Associated With Cardiac Structure and Function: A Meta-analysis and Replication of Genome-wide Association Data", JAMA. Author manuscript; available in PMC, Nov. 8, 2010, 20 pages.

Verstraeten, Aline , "Aetiology and management of hereditary aortopathy", Nature Reviews, Cardiology vol. 14, Apr. 2017, 12 pages.

Wain, Louise V., "Novel Blood Pressure Locus and Gene Discovery Using Genome-Wide Association Study and Expression Data Sets From Blood and the Kidney", Hypertension, American Heart Association, Inc., Jun. 30, 2017, 16 pages.

Wild, Philipp S., "Large-scale genome-wide analysis identifies genetic variants associated with cardiac structure and function", The Journal of Clinical Investigation, vol. 127 No. 5, May 2017, 15 pages.

Wolf, F. Alexander , "SCANPY: large-scale single-cell gene expression data analysis", Genome Biology, BioMed Central, 2018, 5 pages.

Wolock, Samuel L., "Scrublet: Computational Identification of Cell Doublets in Single-Cell Transcriptomic Data", Cell Systems, Elsevier Inc., 2018, 29 pages.

Wu, Gifford , "Mapping ICD-10 and ICD-10-CM Codes to Phecodes", JMIR Medical Informatics, May 11, 2020, 23 pages.

Yang, Jian , "FTO genotype is associated with phenotypic variability of body mass index", Nature. Author manuscript; available in PMC, Apr. 11, 2013, 16 pages.

Zhu, Zhihong , "Integration of summary data from GWAS and eQTL studies predicts complex trait gene targets", Nature Genetics, vol. 48, No. 5, May 2016, 9 pages.

* cited by examiner

Enlarged ascending aorta

Enlarged descending aorta

2x

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
aagcagtggt atcaacgcag agtacatggg                                        30

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
cccatgtact ctgcgttgat accactgctt                                        30

+

METHODS OF PREDICTING ANEURYSMS OF THE ASCENDING AND DESCENDING AORTA

CROSS REFERENCE TO RELATED APPLICATIONS

This application is a national stage filing under 35 U.S.C. § 371 of International PCT Application No. PCT/US2021/031329, filed May 7, 2021, entitled "METHODS OF PREDICTING ANEURYSMS OF THE ASCENDING AND DESCENDING AORTA," which claims the benefit under 35 U.S.C. § 119(e) of U.S. Provisional Application No. 63/022,400, filed May 8, 2020, entitled "METHODS OF PREDICTING ANEURYSMS OF THE ASCENDING AND DESCENDING AORTA," U.S. Provisional Application No. 63/105,189, filed Oct. 23, 2020, entitled "METHODS OF PREDICTING ANEURYSMS OF THE ASCENDING AND DESCENDING AORTA," and U.S. Provisional Application No. 63/105,785, filed Oct. 26, 2020, entitled "METHODS OF PREDICTING ANEURYSMS OF THE ASCENDING AND DESCENDING AORTA," the entire disclosure of each of which is hereby incorporated by reference in its entirety.

GOVERNMENT SUPPORT

This invention was made with government support under Grant Nos. HL092577, HL128914, and HL105780, awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Nov. 1, 2022, is named B119570107US03-SEQ-KVC, and is 836 bytes in size.

FIELD OF THE INVENTION

The present disclosure relates to methods of assessing a subject's risk of ascending thoracic aortic aneurysm or descending thoracic aortic aneurysm by detecting one or more single nucleotide polymorphisms (SNP) in one or more specific genes.

BACKGROUND OF THE INVENTION

Aortic aneurysm, a pathologic enlargement of the aorta, is common, having a prevalence of approximately 1% of people in industrialized nations (Emelia et al. (2019) *Circulation* 139, e56-e528). Over time, the enlarged aorta progressively expands; this process can lead to aortic dissection and rupture, which are the most catastrophic complications of aortic aneurysm and causes of sudden cardiac death. Currently, the most effective preventive therapy is surgical or endovascular repair of the aorta, morbid procedures that are only performed when aneurysms are detected prior to aortic dissection. However, timely detection is uncommon because thoracic aortic aneurysm is typically asymptomatic until the time of dissection or rupture. Unlike abdominal aortic aneurysm, which has clinical screening guidelines, population screening for thoracic aortic aneurysm is not routinely performed (Isselbacher (2005) *Circulation* 111, 816-828; Owens et al. (2019) *JAMA* 322, 2211-2218).

SUMMARY OF THE INVENTION

Aspects of the disclosure relate to methods for assessing a subject's risk for an aneurysm of the descending thoracic aorta, the method comprising detecting a single nucleotide polymorphism (SNP) in one or more of: PKN2, NAV1, GDF7, CCDC141, COL6A3, LMCD1, ULK4, FLNB, ZBTB20, MASP1, AFAP1, FIP1L1, FGF5, PDLIM5, FER, NKX2-5, MICA, CDKN1A, NT5E, ZNF292, TWIST1, TBX20, PI15, MAL2, SVIL, PLCE1, PCSK7, ADAMTS8, STAT6, ALDH2, ARHGEF40, MYH6, NFATC4, OTUB2, DISP2, FBN1, LOXL1, ADAMTS7, WWP2, TBC1D16, CTIF, DOT1L, ACTN4, SPTBN4, FBXO46, JAG1, and FHL1.

In some embodiments, methods further comprise calculating a polygenic score based on the number of SNPs detected. In some embodiments, methods further comprise comparing the polygenic score to a reference polygenic score. In some embodiments, methods further comprise determining that the subject is at increased risk for an aneurysm of the descending thoracic aorta if the polygenic score is greater than the reference polygenic score.

In some embodiments, the subject's risk for an aneurysm of the descending thoracic aorta is associated with the aortic diameter. In some embodiments, the aortic diameter is determined by computed tomography (CT), magnetic resonance imaging (MRI), or echocardiography. In some embodiments, the aortic diameter is positively correlated with one or more of the following parameters: age, height, weight, obesity, hypertension, varicose veins, cholelithiasis, and headache. In some embodiments, the aortic diameter is inversely associated with coronary artery disease status, type 1 diabetes status, or both.

In some embodiments, the subject's risk for an aneurysm of the descending thoracic aorta is associated with TGF-β signaling.

In some embodiments, the subject's risk for an aneurysm of the descending thoracic aorta is further assessed by detecting one or more of the following genes: SVIL, MASP1, STAT6, AC003986.6, ACTN4, RNASE7, C2orf43, DISP2, CAPN12, FER, SIDT2, PLEKHJ1, AC012065.7, ADAMTS7, and PI15. In some embodiments, the one or more genes is SVIL.

In some embodiments, methods further comprise treating the subject with medication, surgery, or both. In some embodiments, the medication is selected from the group consisting of: aspirin, blood pressure medications, and statins. In some embodiments, the surgery is open surgical repair or endovascular aneurysm repair.

In some embodiments, one or more SNPs is selected from the SNPs in Table 4.

Further aspects of the disclosure relate to methods for assessing a subject's risk for an aneurysm of the ascending thoracic aorta, comprising detecting a single nucleotide polymorphism (SNP) in one or more of: SPSB1, SF3A3, EDN2, FGGY, HMCN1, RYR2, OSR1, ZEB2, MBD5, FIGN, COL6A3, FGD5, ULK4, FLNB, LRIG1, GATA2, MASP1, FGF5, HAND2, ATP6AP1L, PCSK1, PPIC, PRDM6, KCNMB1, ADTRP, EDN1, CDKN1A, COL21A1, AIG1, ESR1, TBX20, HERPUD2, ELN, LIMK1, SEMA3D, MSRA, SLC25A37, PI15, ANGPT1, ENPP2, HAS2, FBXO32, TRAPPC9, LPAR1, CACNB2, ARIDSB, JMJD1C, PLCE1, NOC3L, ENTPD1, VTI1A, ABCC8, DCDC1, ANO1, NCAM1, ADAMTS8, RERG, ABCC9, USP15, LLPH, POC1B-GALNT4, CRADD, C12orf75, MED13L, FGF9, DLEU1, ASB2, DISP2, FBN1, THSD4, GNAO1, WWP2, HYDIN, CDH13, CBFA2T3, SMG6, CD68, MAP2K4, ATAD5, COPRS, PIEZO2, CCNE1, SLX4IP, SLC24A3, KCNE2, and TNRC6B.

In some embodiments, methods further comprise calculating a polygenic score based on the number of SNPs detected. In some embodiments, methods further comprise comparing the polygenic score to a reference polygenic score. In some embodiments, methods further comprise determining that the subject is at increased risk for an aneurysm of the descending thoracic aorta if the polygenic score is greater than the reference polygenic score.

In some embodiments, the subject's risk for an aneurysm of the ascending thoracic aorta is associated with the aortic diameter. In some embodiments, the aortic diameter is determined by computed tomography (CT), magnetic resonance imaging (MRI), or echocardiography. In some embodiments, the aortic size is positively correlated with one or more of the following parameters: height, weight, age, cardiovascular disease status, varicose veins, obesity, and osteoarthritis. In some embodiments, the cardiovascular diseases are selected from the group consisting of: hypertension, valvular disorders, and cardiac arrhythmias.

In some embodiments, the subject's risk for an aneurysm of the ascending thoracic aorta is associated with TGF-β signaling.

In some embodiments, the subject's risk for an aneurysm of the ascending thoracic aorta is further assessed by detecting one or more of the following genes: CTD-2337A12.1, RP11-254122.1, PRDM6, ULK4, AC008592.4, USP15, FIGN, AC092594.1, CBFA2T3, SRR, ABCC9, P11-589N15.2, ESR1, RP11-227D13.1, RP11-46107.1, AC008592.3, SMG6, GNAO1, RP11-441F2.5, THSD4, PI15, CDH13, RP11-981G7.2, FAM85B, TNRC6B, RP11-731K22.1, MTMR9, MASP1, HNRNPA1P16, MPPED2, SGK223, AF131215.8, CYP2C9, FLNB, RP11-713H12.1, NOC3L, RP11-470E16.1, ATP2B1, FHL3, SF3A3, ERI1, SNX24, RP11-830F9.6, RP11-467C18.1, AF131215.2, AF131215.9, MBD5, ACVR2A, FAM66A, RYR2, HSPD1, UTP11L, and RP11-145M4.3.

In some embodiments, the one or more genes is ULK4. In some embodiments, the one or more genes is THSD4. In some embodiments, the one or more genes is USP15.

In some embodiments, methods further comprise treating the subject with medication, surgery, or both. In some embodiments, the medication is selected from the group consisting of: aspirin, blood pressure medications, and statins. In some embodiments, the surgery is open surgical repair or endovascular aneurysm repair.

In some embodiments, one or more SNPs is selected from the SNPs in Table 3.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations of thereof herein, is meant to encompass the items listed thereafter and equivalents thereof as well as additional items

BRIEF DESCRIPTION OF THE DRAWINGS

The accompanying drawings are not intended to be drawn to scale. The drawings are illustrative only and are not required for enablement of the disclosure. For purposes of clarity, not every component may be labeled in every drawing. In the drawings:

FIG. 2A (Ascending Thoracic Aorta) and FIG. 2B (Descending Thoracic Aorta) depict loci with $P<5\cdot10^{-8}$ shown in dark gray (if not previously reported) or starred (if previously reported in common variant association studies for aortic size or disease status [aneurysm or dissection]). The X chromosome is represented as '23'. FIG. 2C depicts a Venn diagram showing the number of loci uniquely associated at $P<5\cdot10^{-8}$ with either the ascending or descending thoracic aorta. Loci associated with both ascending and descending thoracic aorta are enumerated in the table to the right. Loci whose lead SNP's nearest gene differs between ascending and descending are demarcated as "Ascending/Descending".

FIG. 3A shows protein-coding genes associated with the size of the ascending (left panel) and descending (right panel) thoracic aorta based on an integrated gene expression prediction. The x axis represents the magnitude of the TWAS Z score, while the y axis represents the $-\log_{10}$ of the TWAS P value. Genes achieving Bonferroni significance are labeled to show positive correlation or negative correlation. The top 5 positively and negatively correlated genes are labeled. FIG. 3B shows rare variant collapsing burden test results for the genes within a 500 kb window around GWAS loci (69 for ascending and 61 for descending). Loss of function (LoF) carrier status in each gene was tested for association with the size of the ascending (left panel) and descending (right panel) thoracic aorta. The x axis represents the effect size of LoF in each gene on aortic size, while the y axis represents the $-\log 10$ of the association P value in a logistic model. SVIL achieved $P<0.05/61$ in the descending aorta. The top 5 positively and negatively correlated genes are labeled.

FIG. 4A shows that uniform manifold approximation and projection (UMAP) revealed 10 main clusters. Each dot represents an individual nucleus, labeled by putative cell type as identified from Leiden clustering. FIG. 4B shows that the top five most selectively expressed genes for each cluster were identified as those with the largest fold-change difference in expression comparing the given cluster with all other clusters, only considering genes expressed in at least 30% of nuclei and with a Benjamini-Hochberg corrected p<0.01. The shade of the dot represents the average log 2 expression for a gene across all nuclei in a given cluster and the size of the dot represents the percentage of nuclei in the cluster with non-zero expression. The cell type labels were created by comparing selectively expressed genes in each cluster of nuclei with the literature. FIGS. 4C-4D show cell-type specificity of genes with expression data supported by the TWAS in the ascending (FIG. 4C) and descending (FIG. 4D) aorta. The size of each square represents the average log 2(Expr) for a gene across all nuclei in a given cluster. The darkness of each square represents the magnitude of the log fold-change comparing the expression of the given gene in each cluster to all other clusters based on a formal differential expression model, with circled squares representing negative log fold-change and non-circled squares representing positive log fold-change. A dot represents significant up- or down-regulation in the given cluster based on a Benjamini-Hochberg correction for multiple testing at FDR <0.01. Expr=Normalized nucleus-level expression calculated as the number of counts of a gene divided by the total number of counts in the nucleus and multiplied by 10,000; FC=Fold-change.

Figure 5:
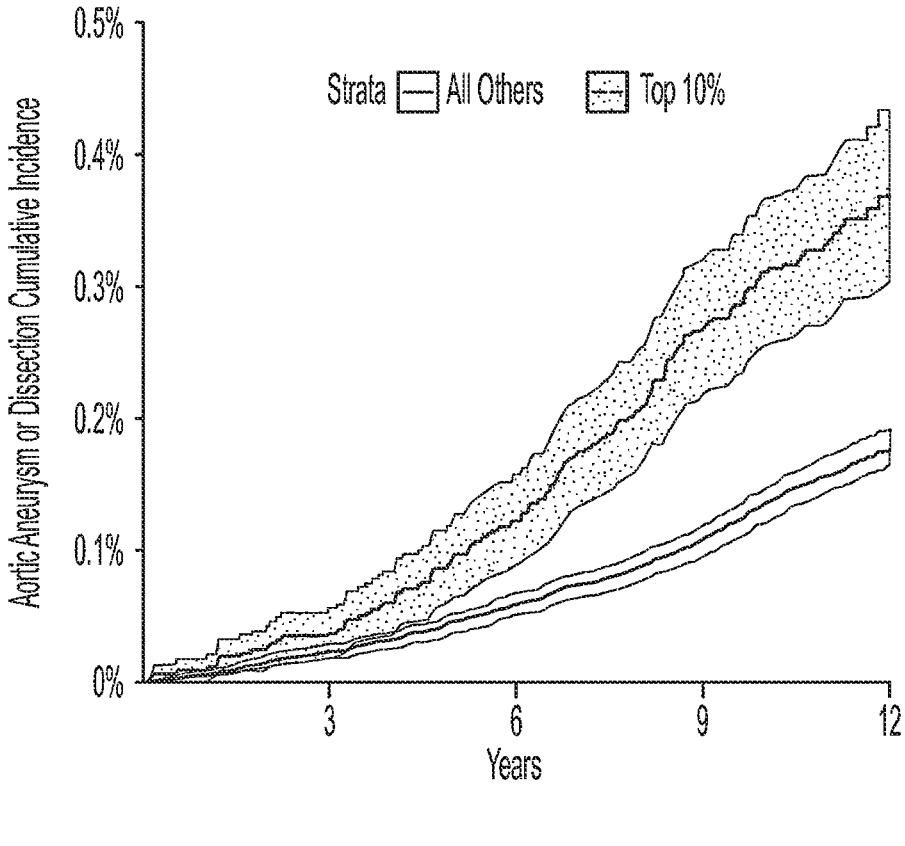

FIG. 5 shows cumulative incidence of thoracic aortic aneurysm or dissection stratified by polygenic score. The cumulative incidence (1 minus the Kaplan-Meier survival estimate) of a diagnosis of aortic aneurysm or dissection (Y axis) is plotted against the number of years since UK Biobank enrollment (X axis). Individuals in the top tenth percentile of the polygenic score for ascending aorta size are shown in dark gray; the remaining 90% are shown in light gray. The 95% confidence intervals (from the cumulative hazard standard error) are represented with lighter shades.

Figure 6:
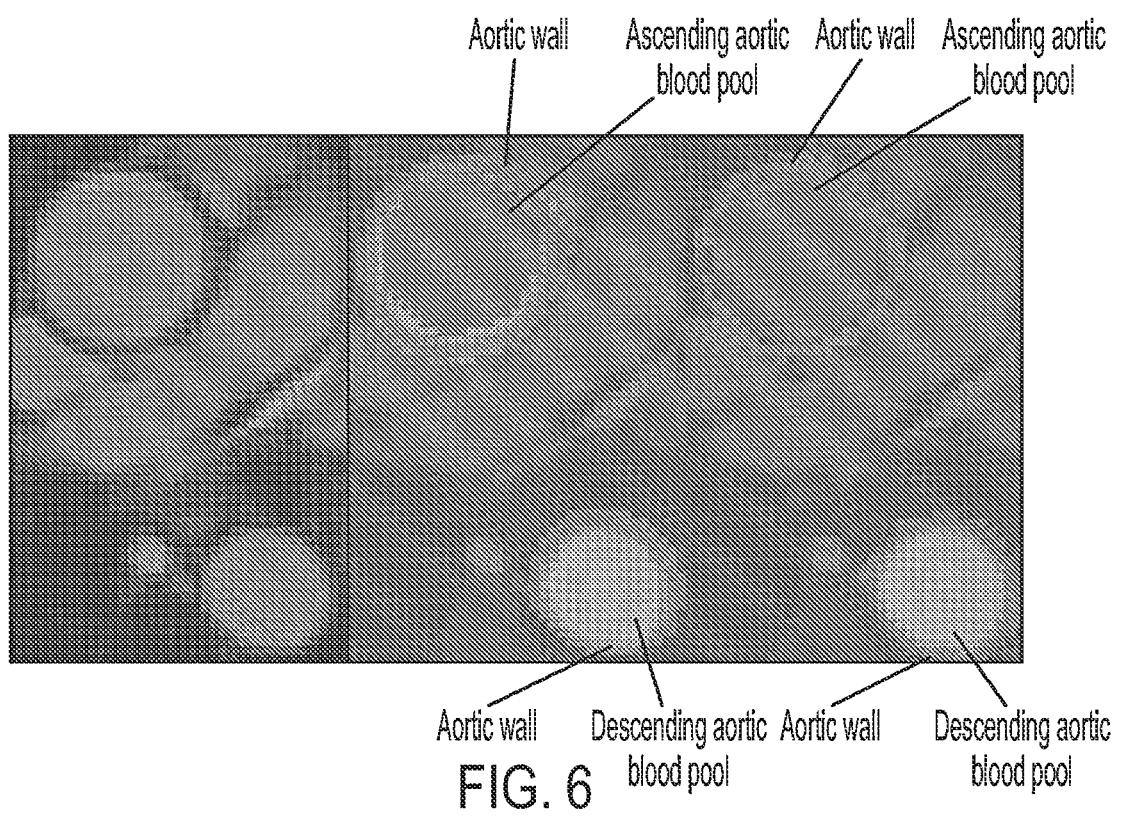

FIG. 6 shows a comparison of 3 pixel and 1 pixel resolution annotation. The left panel shows a zoomed-in view of an aortic distensibility image. The center panel shows a deep learning segmentation output of the distensibility image, colorized by a model trained on images that were annotated with a 3 pixel radius brush. As can be seen in this panel, the aortic wall annotations cross into the aortic blood pool. The right panel shows a deep learning segmentation output of the distensibility image, colorized by a model trained on images that were annotated with a 1 pixel radius brush, yielding a tighter boundary between the aortic blood pool and the aortic wall. In the center and right panels, the ascending aortic blood pool, the descending aortic blood pool, and the aortic wall are labeled.

Figure 7:
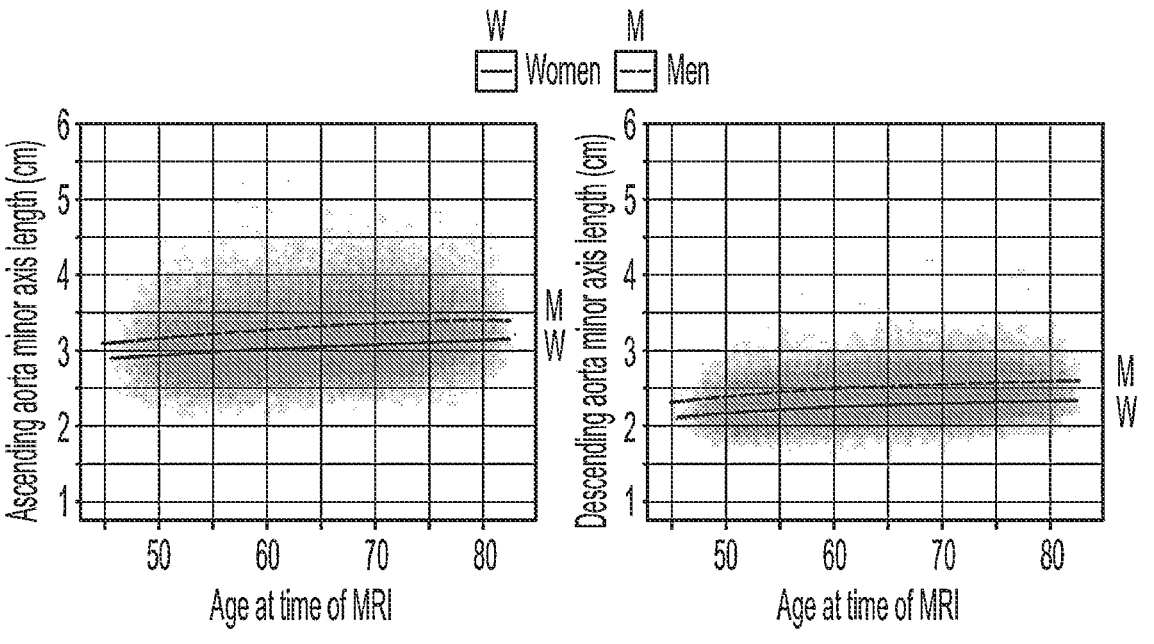

FIG. 7 shows aortic size by age and sex. The length of the minor elliptical axis of aorta at its maximum size during the cardiac cycle (i.e., the diameter) is shown for the ascending aorta (left panel) and the descending aorta (right panel). The x axis represents the participant's age at the time of cardiac MRI and the y axis represents the size of aorta. Each point represents one person's measurements; the trend lines for men and women are labeled. Sex-specific locally weighted scatterplot smoothing (LOESS) curves are overplotted. Each point represents one of the 42,518 participants who passed imaging quality control for at least one of the ascending or descending aorta measurements: 40,363 had accepted measurements for ascending aorta, and 41,415 had accepted measurements for descending aorta.

Figure 8:
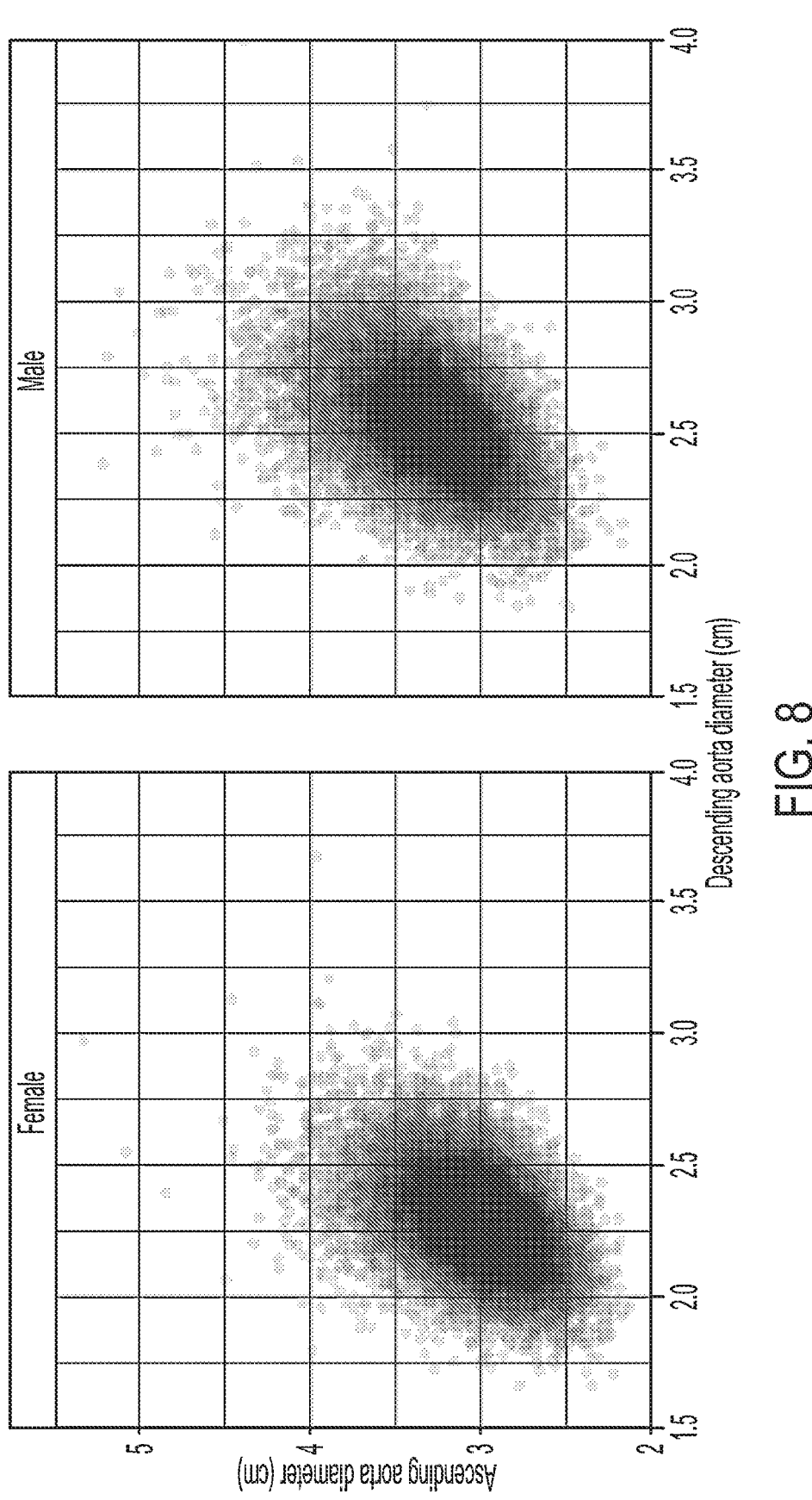

FIG. 8 shows the correlation between ascending and descending aortic diameter. The 39,260 participants with non-missing values for both ascending and descending aortic diameter are plotted. On the x axis is the diameter of descending aorta and on the y axis is the diameter of the ascending aorta. Each individual represents one point. Women are represented in the left panel and men in the right panel. Both panels are plotted to the same scale (1.5-4 cm for descending aorta and 2-5.5 cm for the ascending aorta).

Figure 9A:
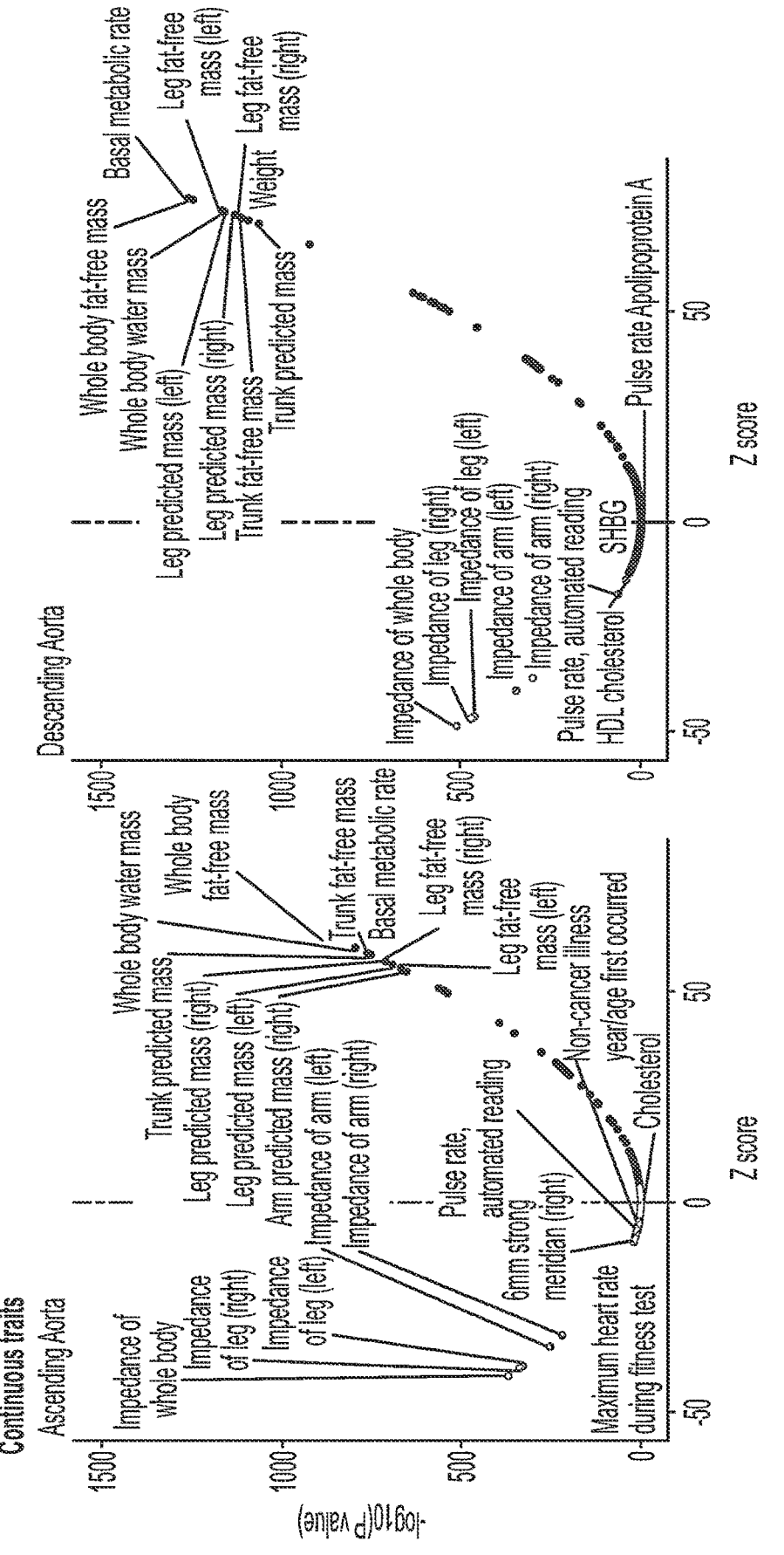
Figure 9B:
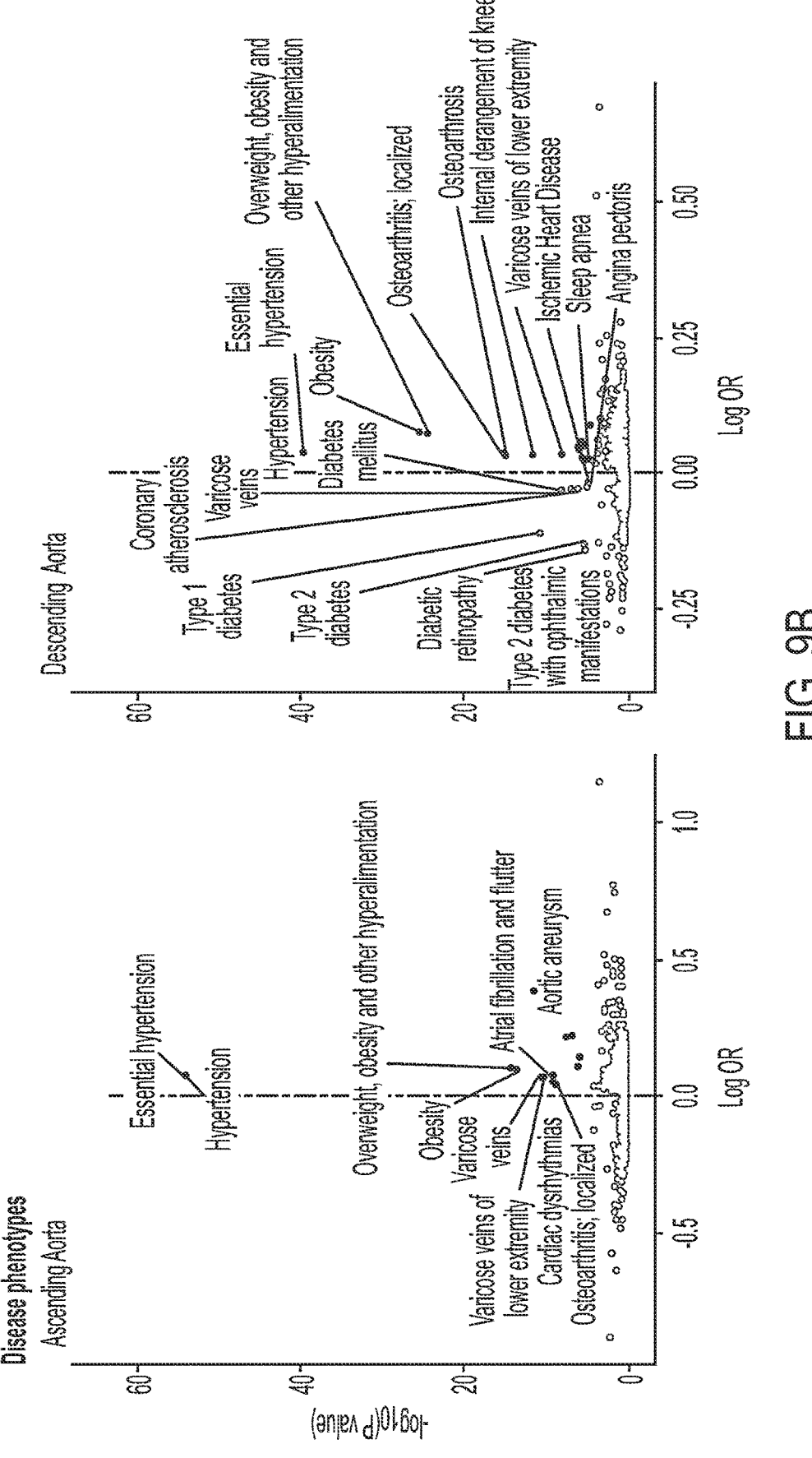

FIGS. 9A-9B show PheWAS with observed aortic traits. FIG. 9A shows phenotypes associated with the size of the ascending (left panel) and descending (right panel) thoracic aorta are represented in volcano plots from a least squares linear model. The x axis represents the magnitude of the association Z score, while the y axis represents the −log 10 of the association P value. Traits achieving Bonferroni significance are labeled and separated by a dashed line, with traits with a positive correlation to the right of the dashed line and traits with a negative correlation to the left of the dashed line. The top 5 positively and negatively correlated traits are labeled. FIG. 9B shows PheCode-based diseases associated with the size of the ascending (left panel) and descending (right panel) thoracic aorta from a logistic regression model. The x axis represents the log of the odds ratio for association between disease and aortic size, while the y axis represents the −log 10 of the association P value. Diseases achieving Bonferroni significance are labeled and separated by a dashed line, with disease phenotypes with a positive correlation to the right of the dashed line and disease phenotypes with a negative correlation to the left of the dashed line. Up to 10 positively and negatively correlated diseases are labeled. Some PheCodes have nearly overlapping definitions (e.g., 'Essential hypertension' and 'Hypertension') but are displayed without modification for completeness.

Figure 10:
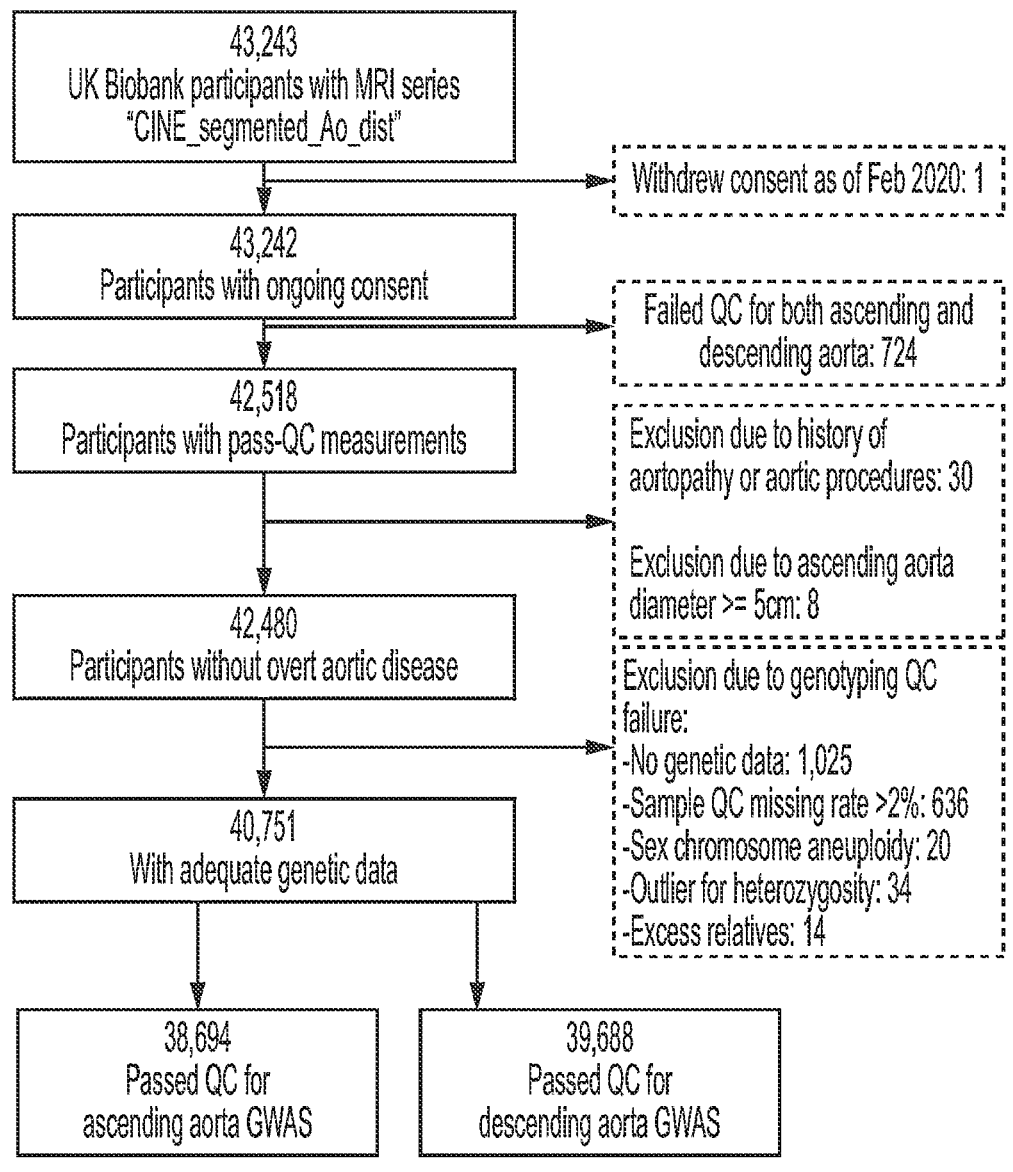

FIG. 10 shows a GWAS Sample Flow Diagram.

Figure 11:
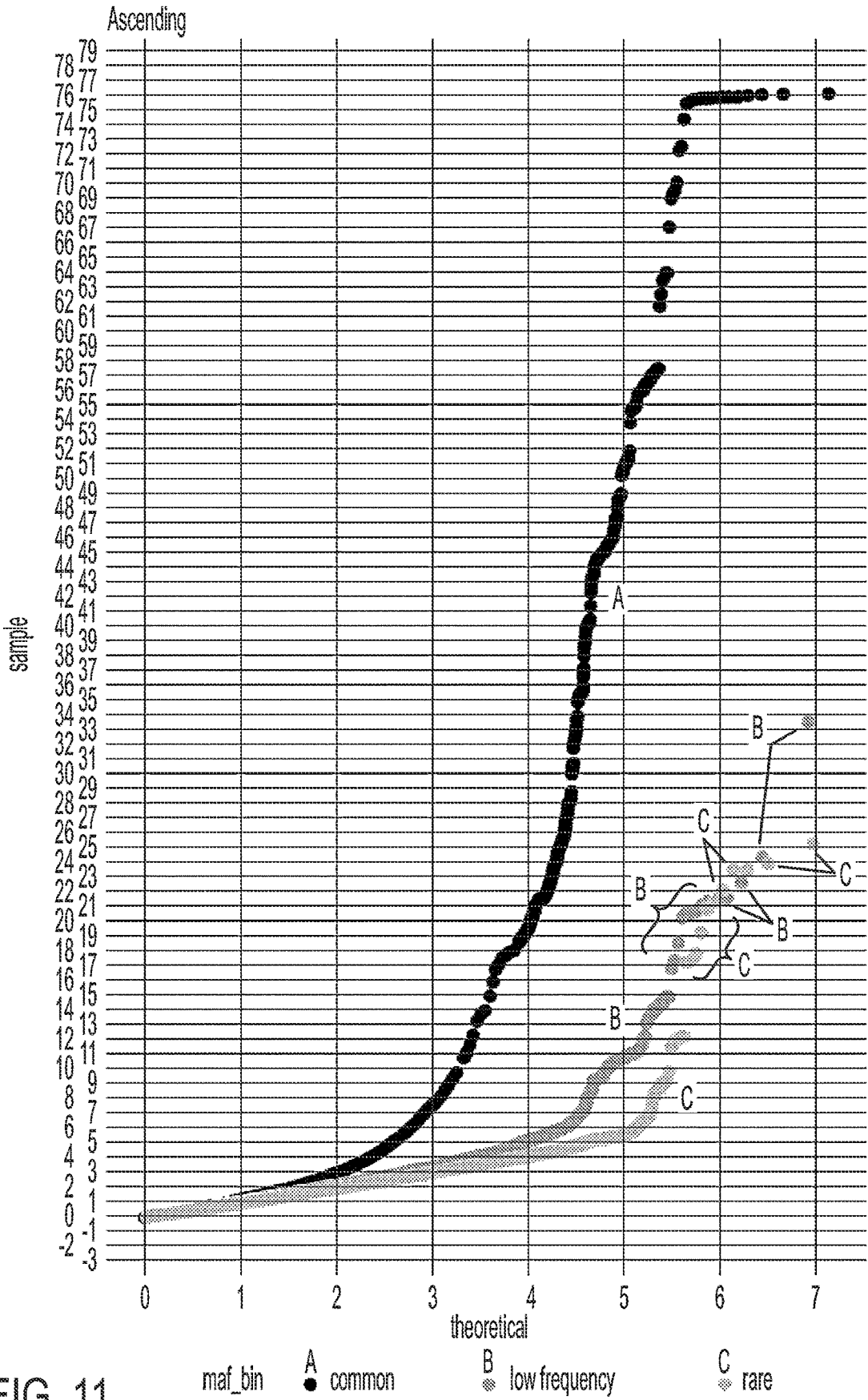
Figure 11:
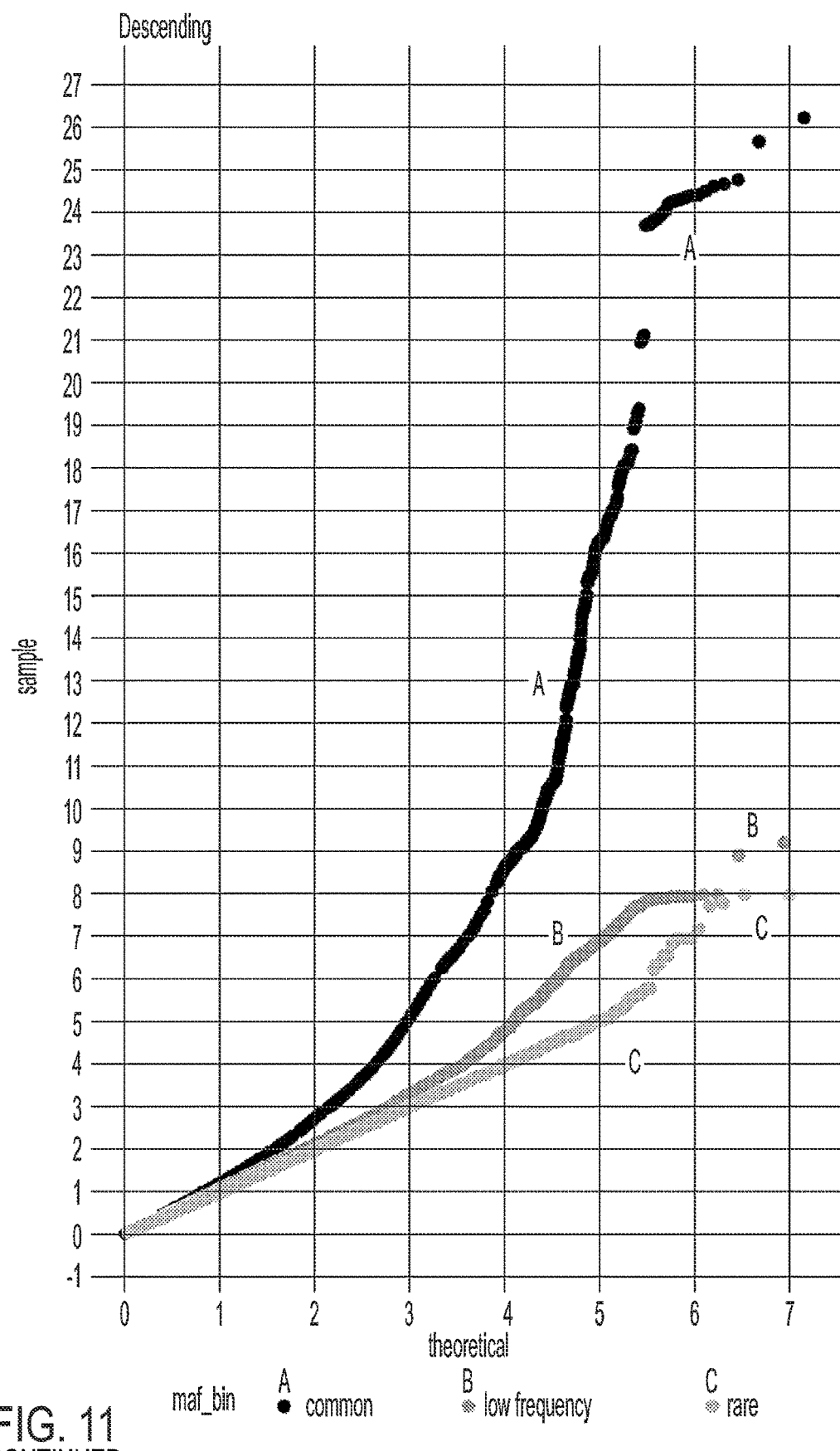

FIG. 11 shows GWAS QQ plots.

Figure 12A:
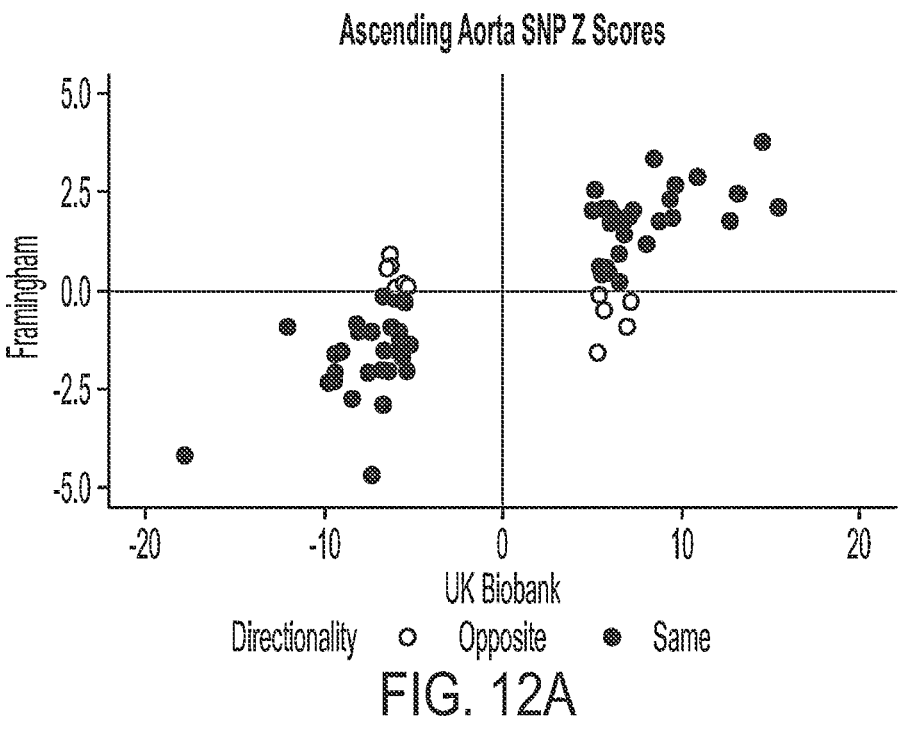
Figure 12B:
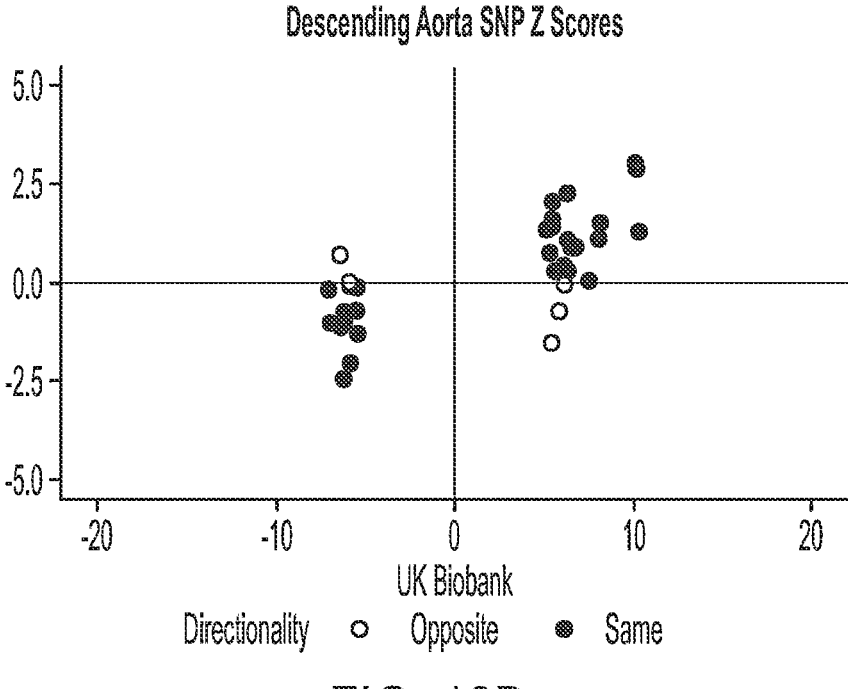

FIGS. 12A-12B show GWAS replication in Framingham. For lead SNPs from the main UK Biobank GWAS that could be identified in a GWAS from FHS, each SNP is plotted based on the UK Biobank Z score (x axis) and the FHS Z score (y axis). 72 SNPs for ascending aortic diameter (FIG. 12A) and 41 SNPs for descending aortic diameter (FIG. 12B) could be identified in FHS and are plotted here. SNPs where the direction of effect is in agreement between FHS and UK Biobank are plotted in light gray, while those with opposite direction of effect are marked in dark gray.

Figure 13A:
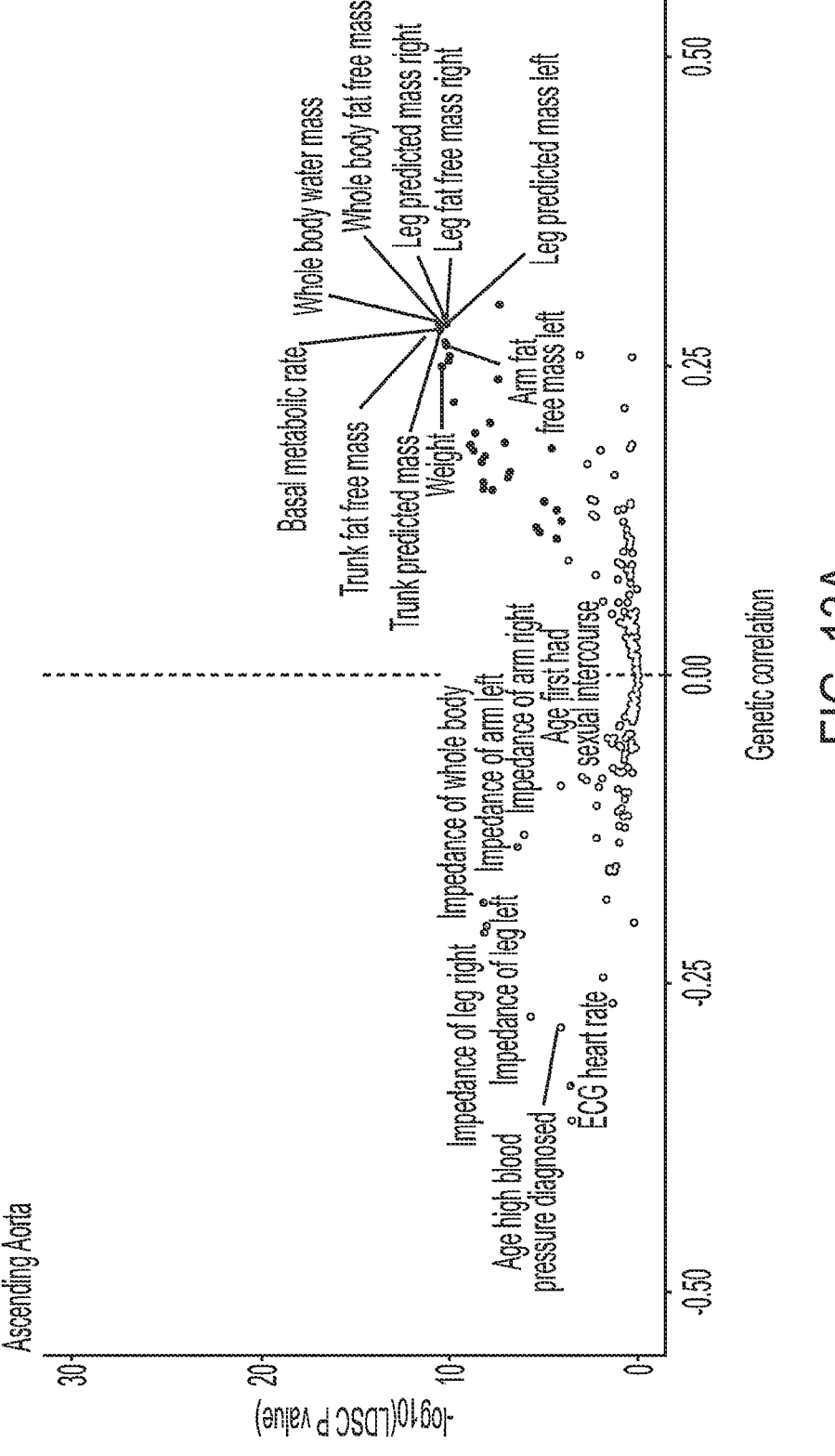
Figure 13B:
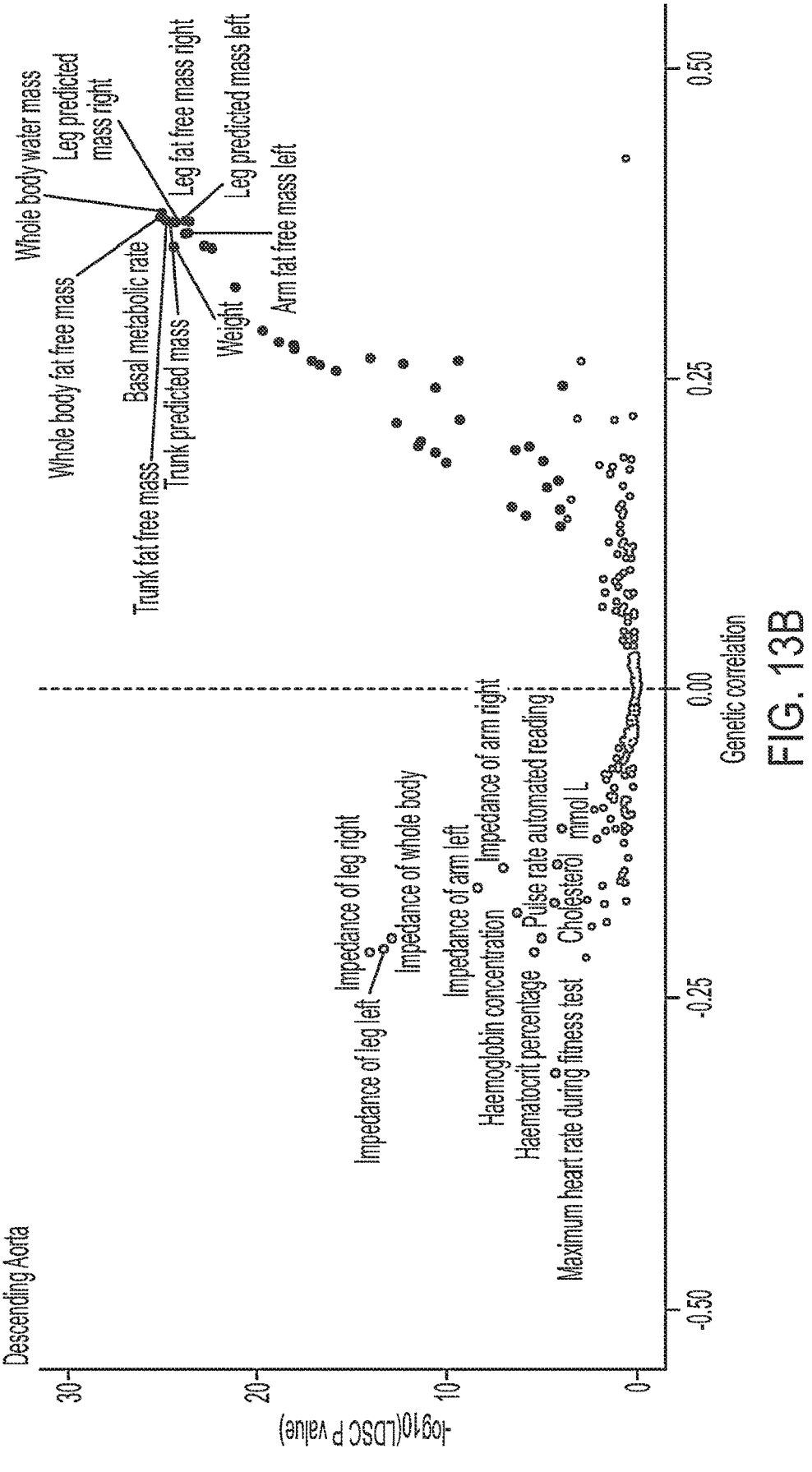

FIGS. 13A-13B show genetic correlation with continuous traits. The genetic correlation between continuous traits and the ascending (FIG. 13A) and descending (FIG. 13B) thoracic aorta in the UK Biobank are represented in volcano plots. Of the 281 tested traits, genetic correlation with 257 traits was computable in the ascending aorta and with 256 traits in the descending aorta. The x axis represents the magnitude of genetic correlation, while the y axis represents the −log 10 of the genetic correlation P value, based on ldsc. Traits achieving Bonferroni significance are labeled and separated by a dashed line, with traits with a positive correlation to the right of the dashed line and traits with a negative correlation to the left of the dashed line. The top 10 positively and negatively associated traits are labeled.

Figure 14:
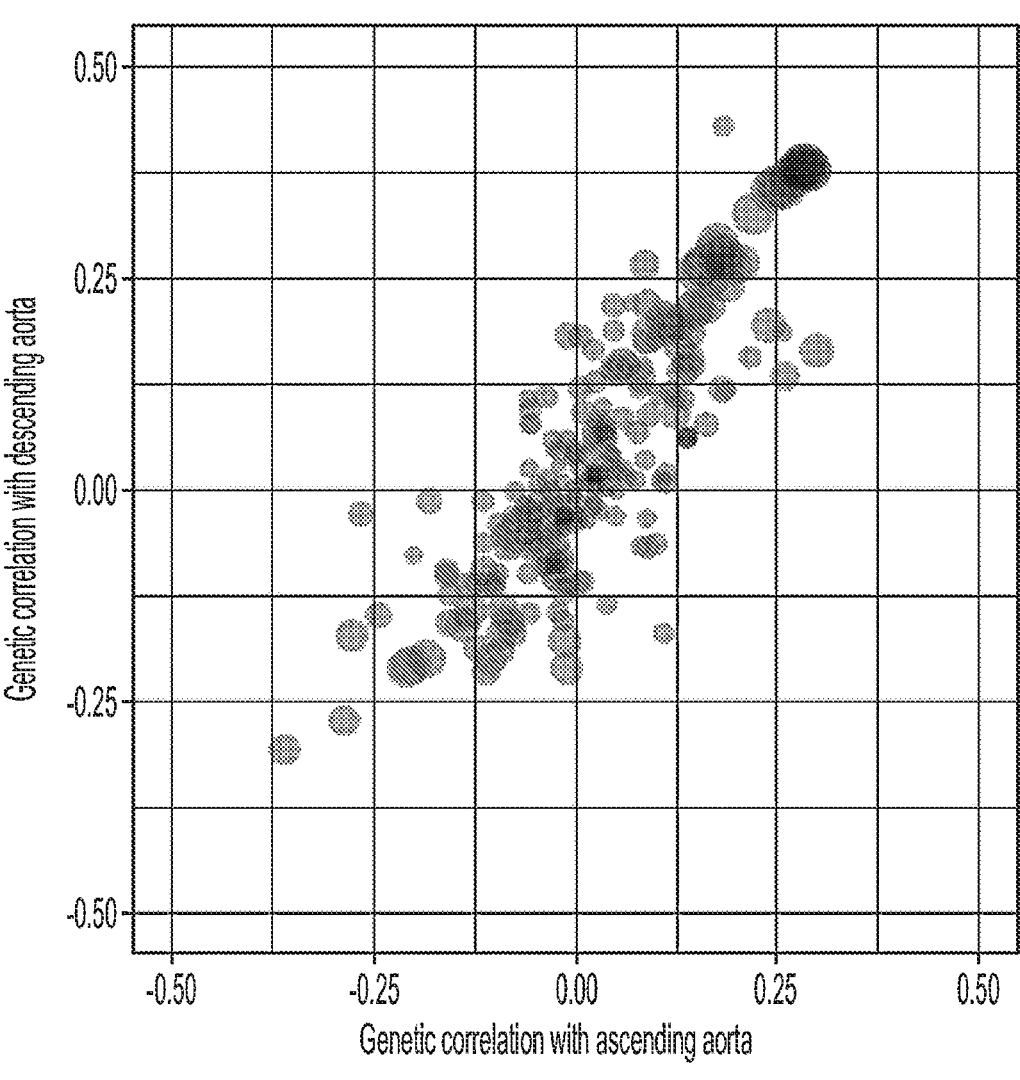

FIG. 14 shows genetic correlation between continuous traits and the ascending and descending aorta. The Z scores for genetic correlation between continuous traits measured by the Neale Lab in the UK Biobank and the ascending and descending aorta using ldsc are plotted based on association with ascending aorta (x axis) and descending aorta (y axis). These represent the same data as in FIGS. 13A-13B. 256 traits had computable values for both ascending and descending aorta and are plotted here. Traits with a stronger association P value have a larger point on the plot.

Figure 15:
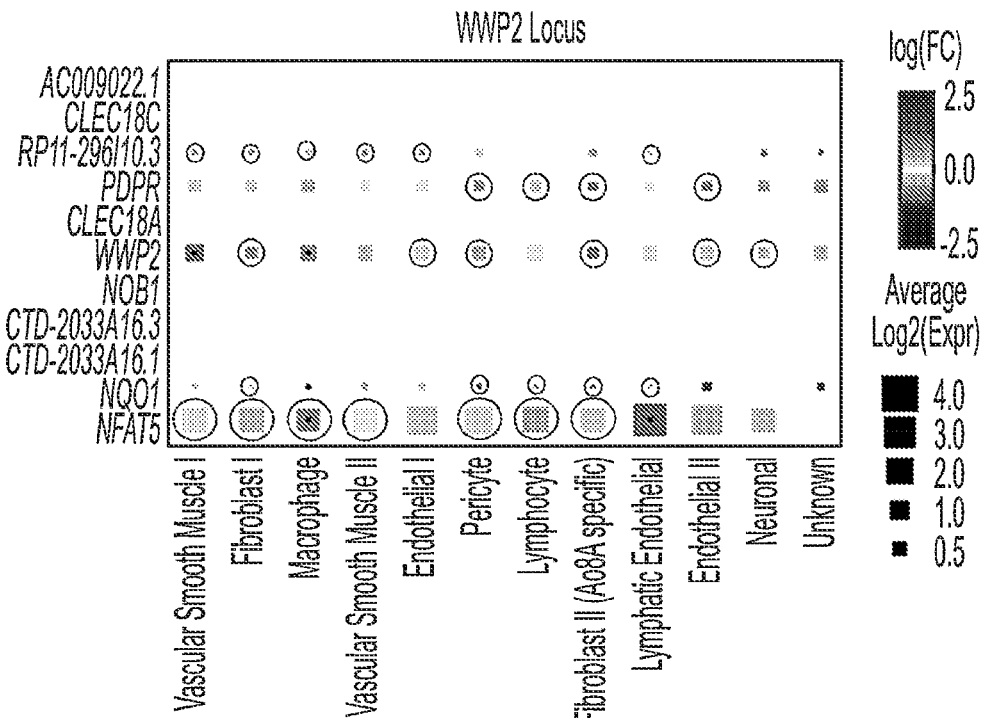

FIG. 15 shows cell type-specific gene expression at the WWP2 locus. Cell-type specificity of genes with expression data within 500 kb of the lead SNP near WWP2. As with FIGS. 4A-4D, the size of each square represents the average log 2(Expr) for a gene across all nuclei in a given cluster. The darkness of each square represents the magnitude of the log fold-change comparing the expression of the given gene in each cluster to all other clusters based on a formal differential expression model, with circled squares representing negative log fold-change and non-circled squares representing positive log fold-change. A dot represents significant up- or down-regulation in the given cluster based on a Benjamini-Hochberg correction for multiple testing at FDR <0.01. Expr=Normalized nucleus-level expression calculated as the number of counts of a gene divided by the total number of counts in the nucleus and multiplied by 10,000; FC=Fold-change.

Figure 16A:
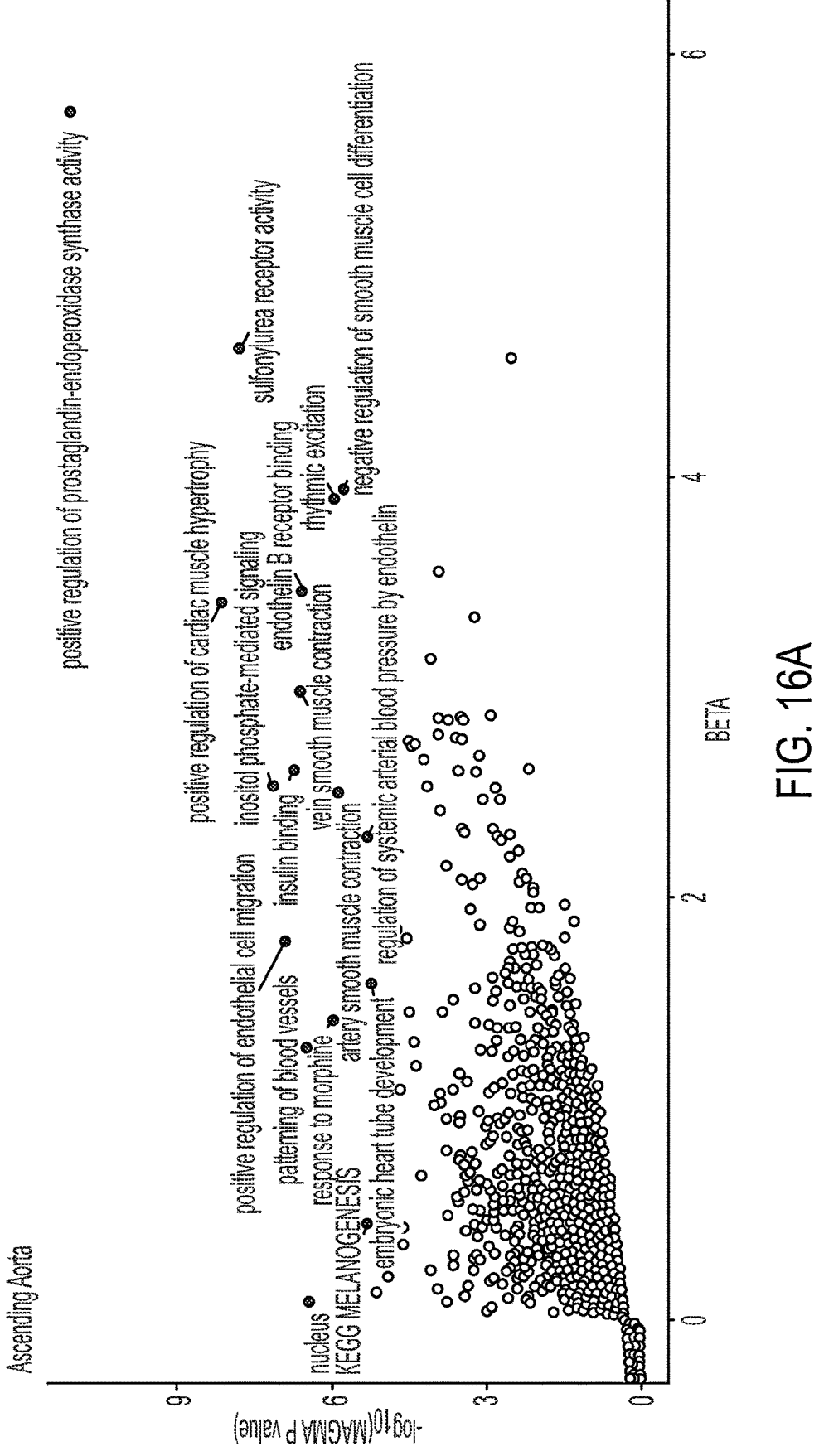
Figure 16B:
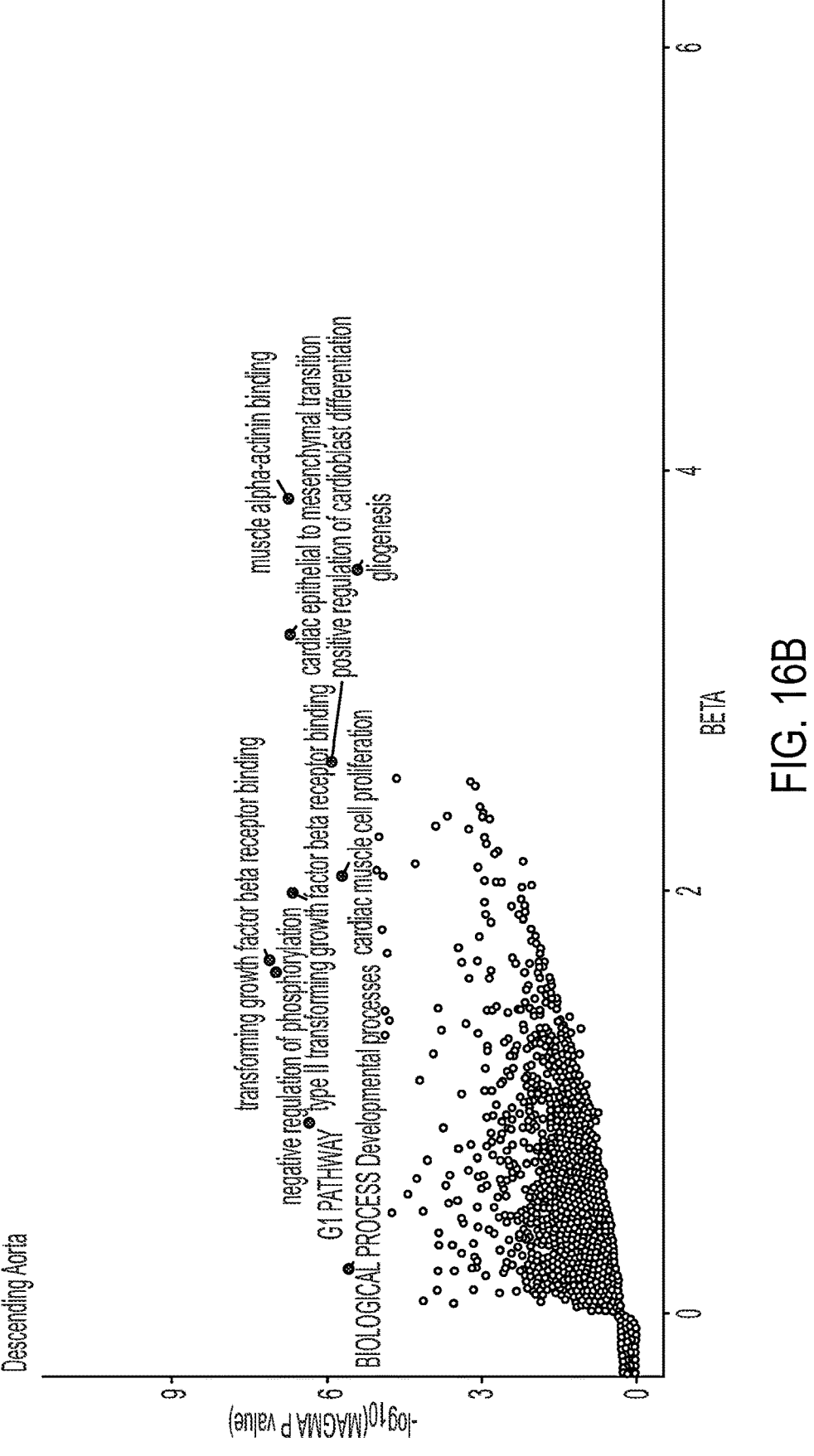

FIGS. 16A-16B show MAGMA gene set associations. Gene sets enriched in MAGMA analysis of the GWAS of the ascending (FIG. 16A) and descending (FIG. 16B) thoracic aorta are represented in volcano plots. The x axis represents the magnitude of estimated effect of a pathway-based gene set on the aortic trait, while the y axis represents the $-\log 10$ of the MAGMA association P value. Pathways achieving Bonferroni significance are colored dark gray and labeled.

Figure 17:
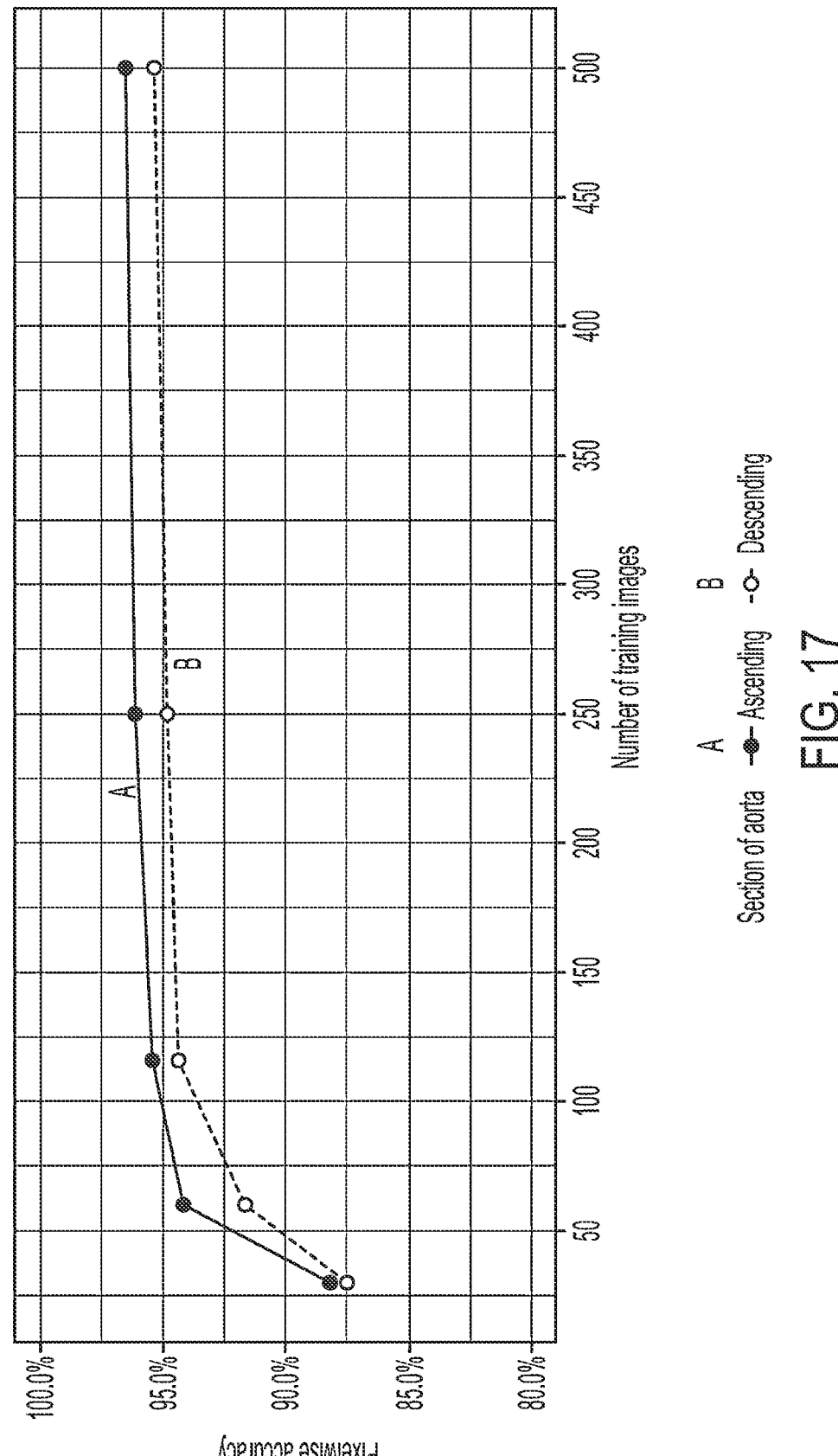

FIG. 17 shows dependence of deep learning model accuracy on number of training samples. The same modeling procedure was performed using 30, 60, 116, 250, or 500 manually annotated images (x-axis), with 5-fold cross validation. The mean pixel accuracy (y-axis) for ascending and descending aorta is reported.

Figure 18A:
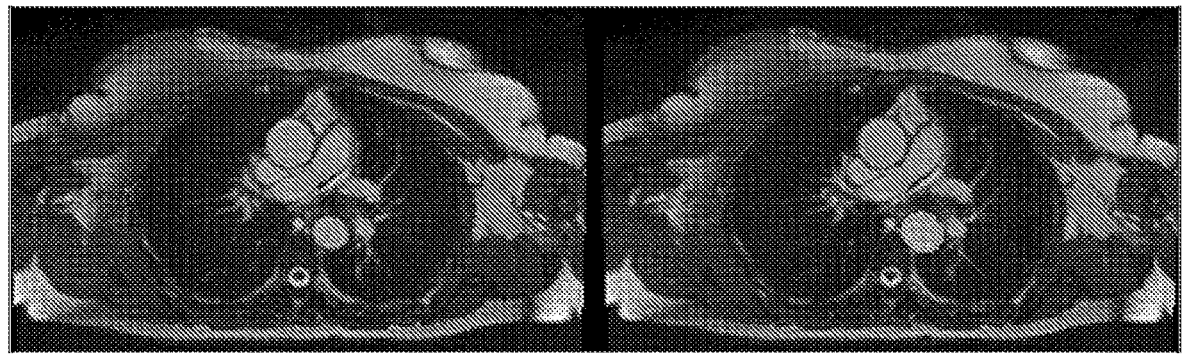
Figure 18B:
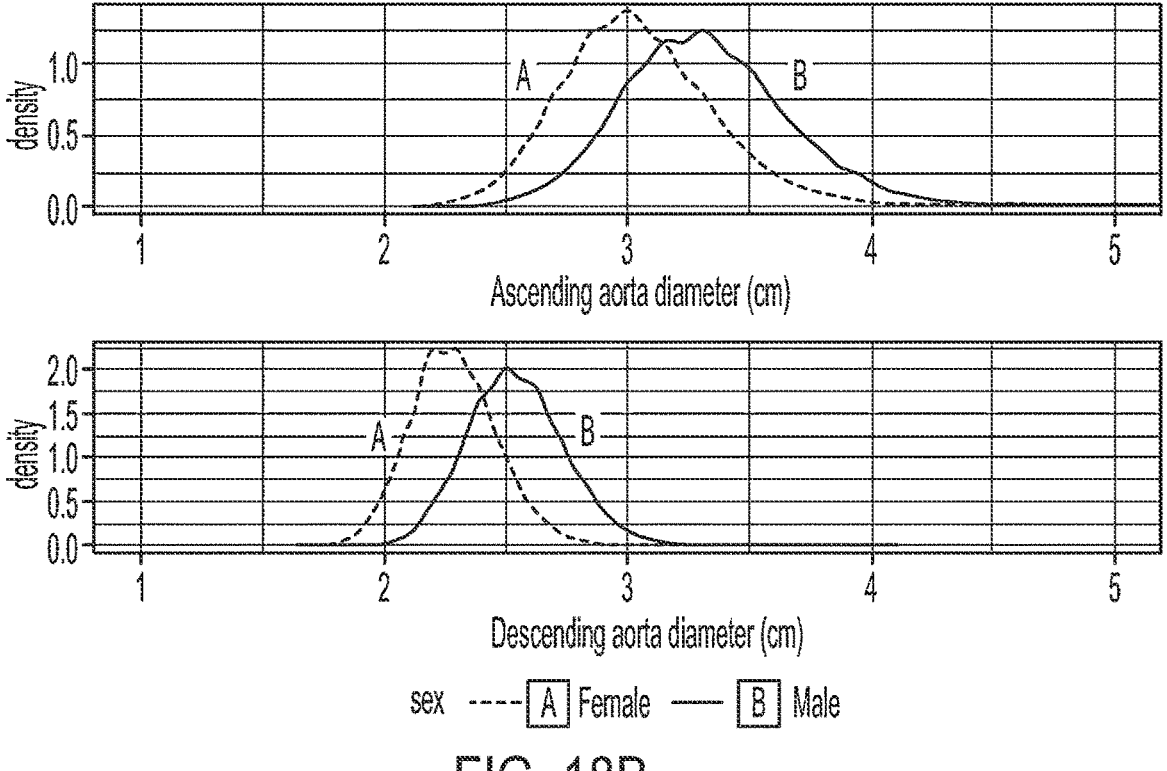
Figure 18C:
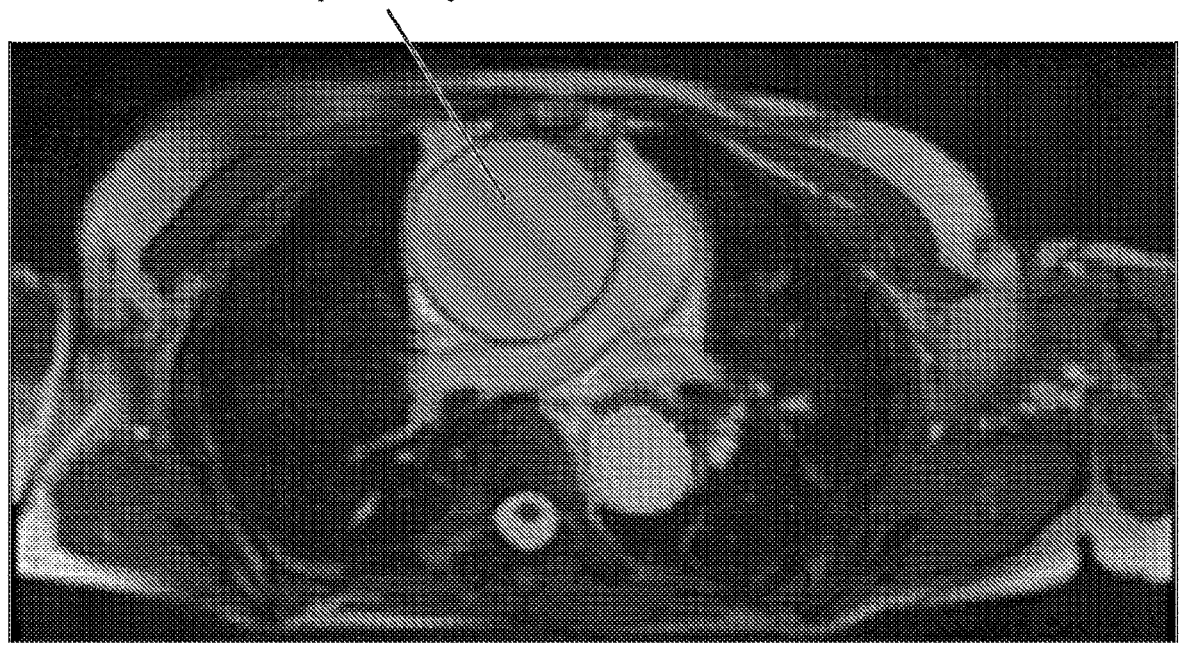
Figure 18D:
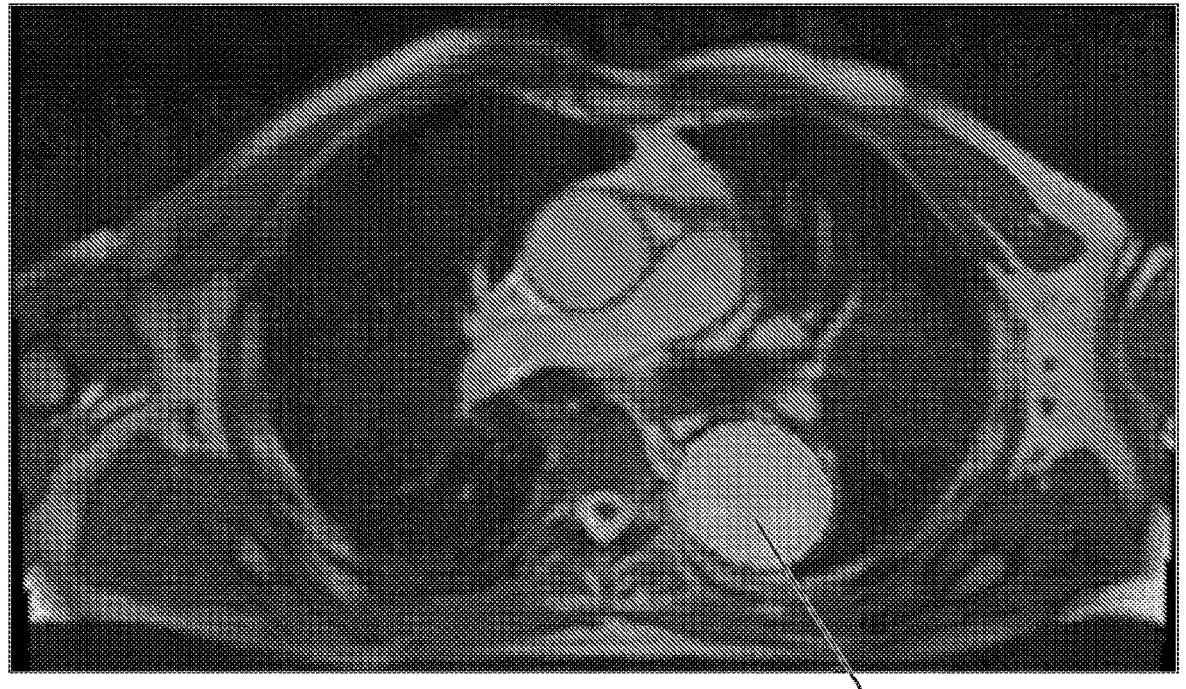

FIGS. 18A-18D show visual quality control for the deep learning model accuracy. The modeling procedure takes an MRI scan as input (FIG. 18A, left) and produces a deep learning segmentation output (FIG. 18A, right). FIG. 18B shows the distributions of deep learning segmentation outputs for ascending aorta diameter (top panel) and descending aorta diameter (bottom panel) in both male and female subjects. The x-axes show aorta diameter in centimeters and the y-axes show data densities. FIG. 18C shows a visual quality control image for an enlarged ascending aorta, as determined by deep learning segmentation. FIG. 18D shows a visual quality control image for an enlarged descending aorta, as determined by deep learning segmentation.

Figure 19:
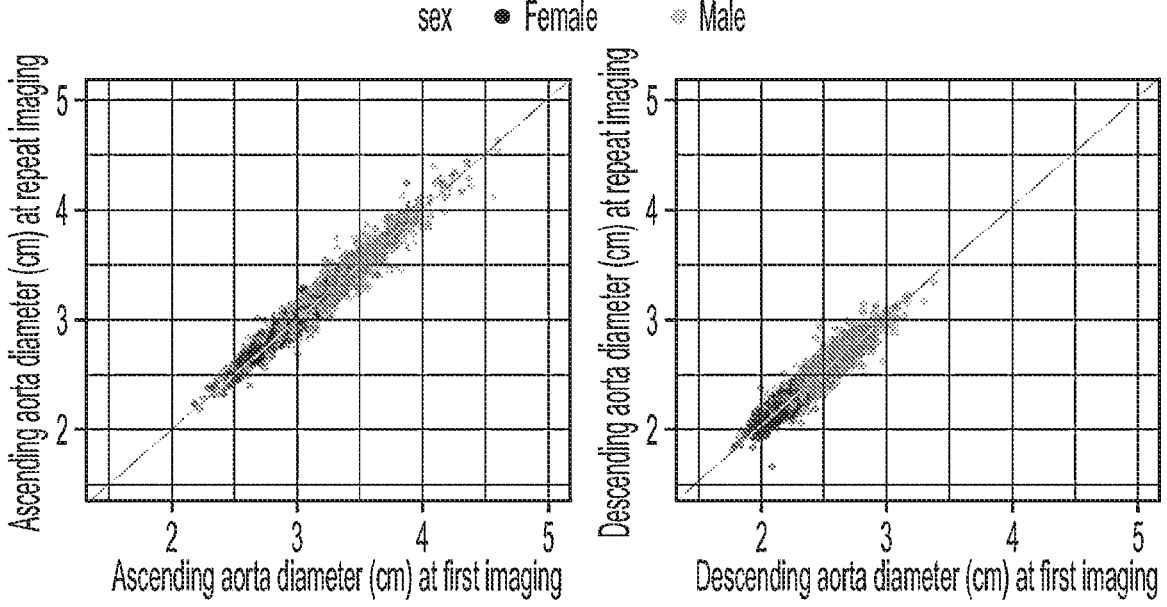

FIG. 19 shows linear regression correlation for ascending aorta diameter and descending aorta diameter values at repeat imaging and at first imaging for the nearly 3,000 UK Biobank participants (both males and females) who underwent imaging at two separate visits. The left panel shows the estimated ascending aorta diameters derived from the deep learning model from the first visit (x-axis) and the estimated ascending aorta diameters derived from the deep learning model from the second visit (y-axis), correlated by linear regression. The right panel shows the same information for the descending aorta diameters. In both panels, male subjects clustered on the higher end of the linear correlation line, while female subjects clustered on the lower end.

Figure 20:
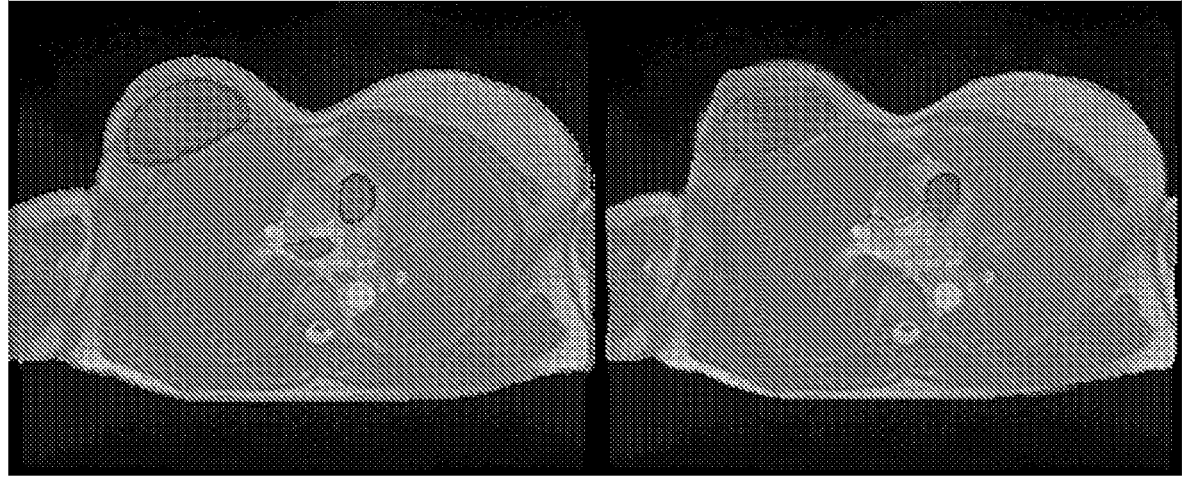

FIG. 20 shows two images used as deep learning training data.

Figure 21:
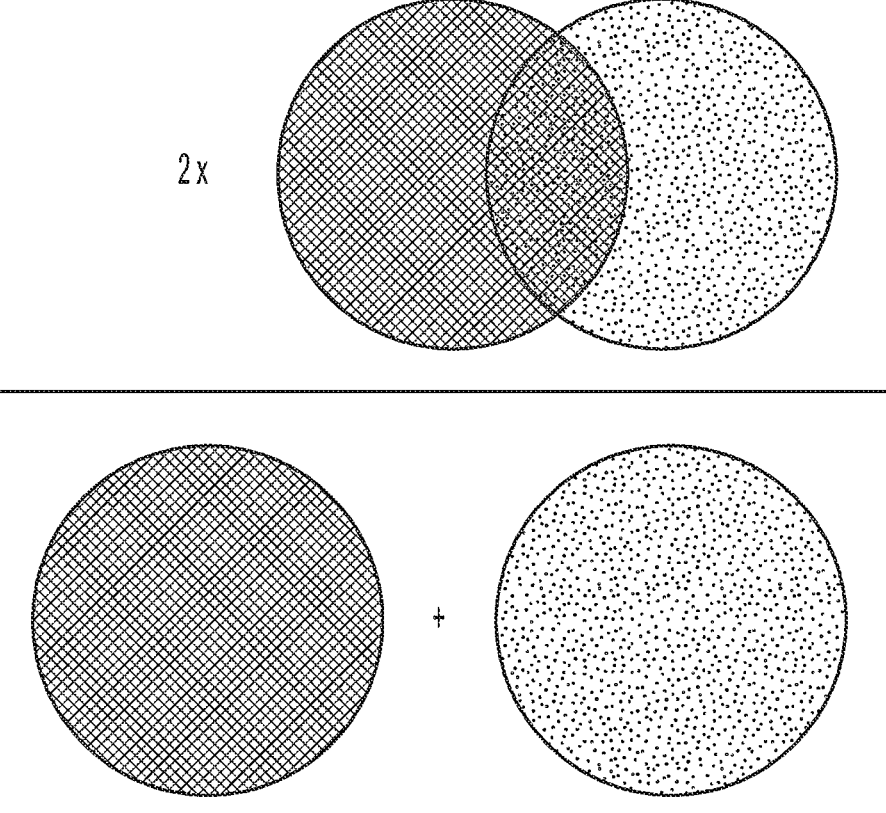

FIG. 21 shows a pictorial representation of the Sorensen-Dice coefficient statistic. The statistic is used to determine the similarity between two images. Two images are compared and overlapping image pixels between the two images are identified. The overlapping area between the two pixels is multiplied by two and the product is divided by the sum of the pixels in each image.

Figure 22:
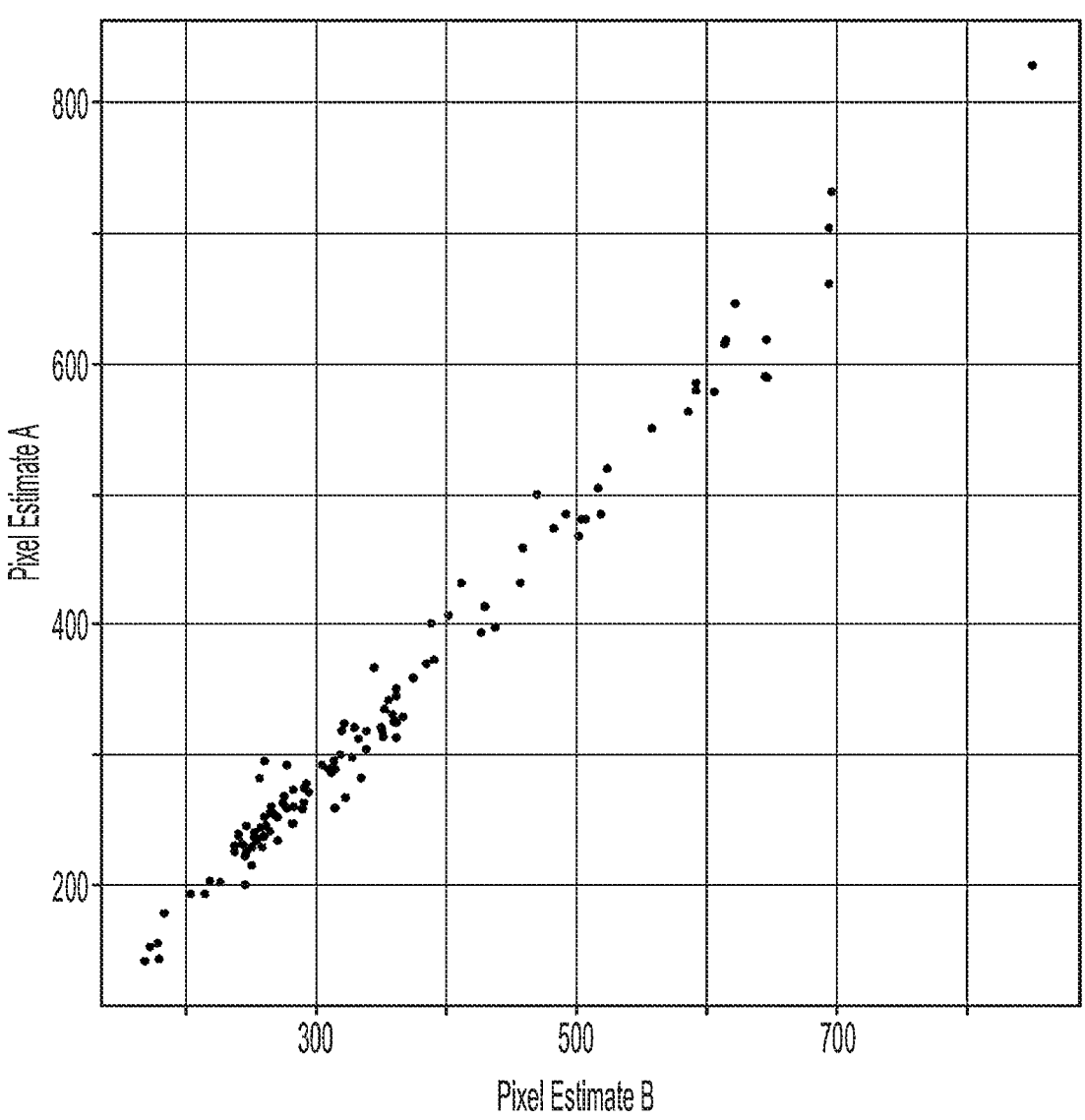

FIG. 22 shows a scatterplot of pixel counts estimated from two individuals.

Figure 23:
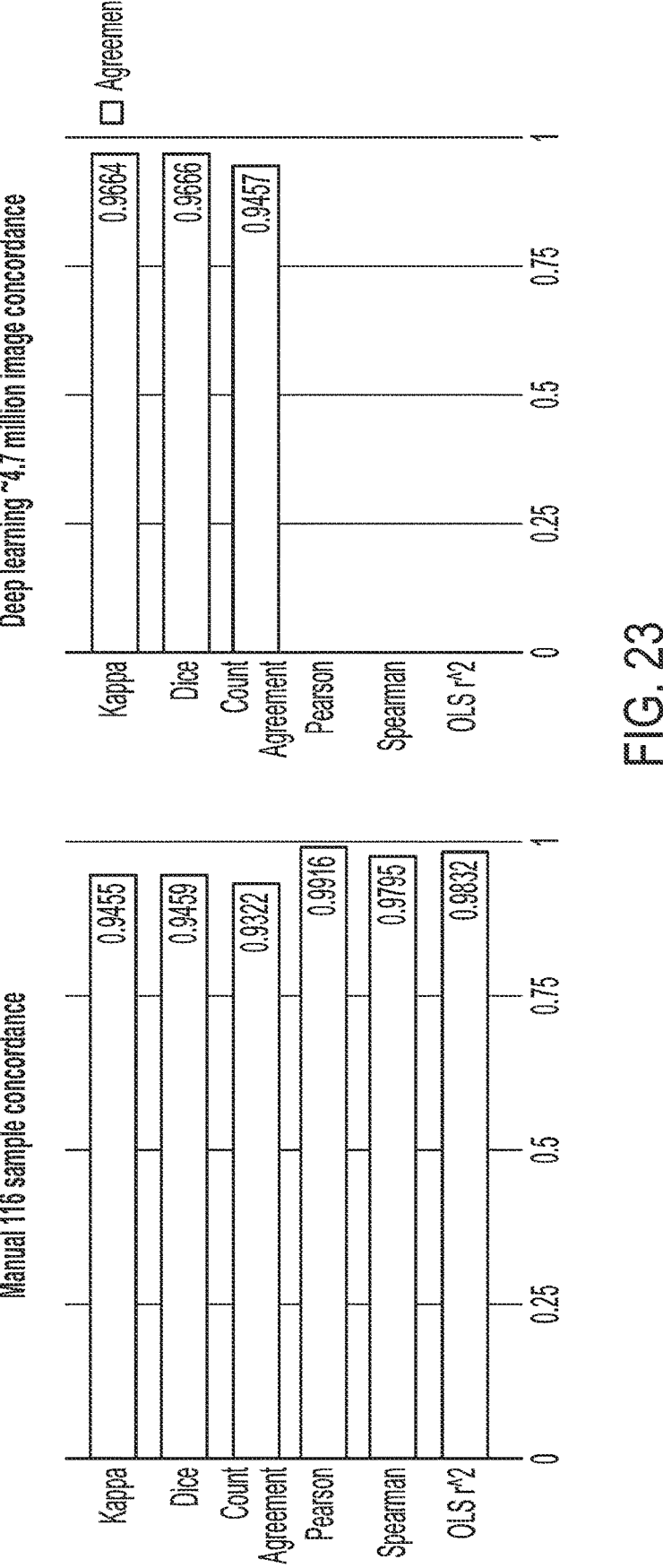

FIG. 23 shows the statistical concordance by various correlation methods of analyses performed by manual programming and analyses performed by deep learning segmentation. The x-axes show the level of statistical concordance and the y-axes show various correlation coefficients (Cohen's kappa coefficient, Sorensen-Dice coefficient, Count agreement, Pearson correlation coefficient, Spearman's rank correlation coefficient, and ordinary least squares correlation).

DETAILED DESCRIPTION OF CERTAIN EMBODIMENTS

The present disclosure provides methods for assessing a subject's risk of an aneurysm of the thoracic ascending aorta or the thoracic descending aorta using single nucleotide polymorphism (SNP) analysis, and optionally, anthropometric and/or phenotypic parameters.

Aortic Aneurysms and Aortic Diameter

The aorta is the largest blood vessel in the body, and enlargement or aneurysm of the vessel can predispose a subject to dissection, resulting in sudden death. Consequently, the epidemiological and genetic contributions to aortic aneurysm are of interest in order to enable the development of new therapeutic targets for medical intervention and to identify at-risk individuals with aortic aneurysms. Clinical studies have suggested the close association of aneurysms of the descending thoracic aorta with atherosclerosis and lifestyle associated risk factors, while those of the ascending aorta occur in younger patients, sometimes associated with pathogenic genetic predisposition (Fann (2002) Coron. Artery Dis. 13, 93-102; Guo et al. (2006) Ann. N. Y. Acad. Sci. 1085, 339-352; Vapnik et al. (2016) Am. J. Cardiol. 117, 1683-1690). Mutations in several genes have been associated with ascending aortic aneurysms, but the small number of implicated genes is mostly limited to highly penetrant Mendelian loci identified in family studies (Jondeau et al. (2014) Curr. Opin. Cardiol. 29, 492-498; Pinard et al. (2019) Circ. Res. 124, 588-606; Verstraeten et al. (2017) Nat. Rev. Cardiol. 14, 197-208). Defining the genetic basis of the diameter of the aorta, as described herein, may enable the identification of asymptomatic individuals at risk for aneurysm or dissection and facilitate the prioritization of potential therapeutic targets for the prevention or treatment of aortic aneurysm.

In some embodiments, the methods described herein may be used to assess a subject's risk of an ascending thoracic aortic aneurysm or a thoracic descending aortic aneurysm. Aortic aneurysms, which involve a ballooning of the wall of the aorta, can occur when the walls of the aorta become weakened. The force of the blood moving through the vessel can lead to an aneurysm. Over time, without treatment, the aneurysm can grow and either rupture or split (dissection), often leading to death. Increased aortic diameter may be associated with increased risk of aneurysm, dissection, and/or death. Accordingly, in some embodiments, a subject's risk of aneurysm is associated with the diameter of the subject's thoracic aorta (e.g., ascending or descending thoracic aorta).

A variety of different risk factors may be associated with thoracic aneurysms, including certain medical conditions, genetic conditions, and trauma. Medical conditions that may be risk factors include aneurysms of other blood vessels, chronic obstructive pulmonary disease, cardiovascular conditions (e.g., atherosclerosis, ischemic heart diseases, peripheral artery disease), high blood cholesterol, high blood pressure, infections, kidney conditions (e.g., chronic renal insufficiency, chronic kidney disease, polycystic kidney disease), pheochromocytoma, and/or vasculitis. There are also several genetic conditions that may increase the risk of thoracic aneurysm, including: Ehlers-Danlos syndrome, Loeys-Dietz syndrome, Marfan syndrome, Turner syndrome, the presence of an abnormal aortic valve (e.g., bicuspid aortic valve), or a family history of thoracic aortic aneurysms. Other risk factors include age (e.g., over 65 years of age), smoking status, obesity, and use of drugs (e.g., stimulants). A subject described herein may have one or more of the risk factors described above. In some embodiments, a subject does not have any of the risk factors described above.

In some embodiments, the diameter of the thoracic aorta positively correlates with at least one of the following risk factors: weight, height, blood pressure, and larger body size generally (e.g., greater forced expiratory volume over one second (FEV1), hand grip strength, and food and alcohol consumption). In some embodiments, the diameter of the thoracic aorta negatively correlates with heart rate and/or certain biomarkers, such as cholesterol, testosterone, and/or sex hormone-binding globulin. In further embodiments, the diameter of the ascending thoracic aorta is associated with at least one of the following risk factors: cardiovascular diseases (e.g., hypertension, aortic aneurysm, valvular disorders, and cardiac arrhythmias), varicose veins, obesity, and/or osteoarthritis. In some embodiments, the diameter of the descending thoracic aorta is associated with at least one of the following risk factors: obesity, hypertension, varicose veins, cholelithiasis, and/or headache. In some embodiments, the diameter of the descending thoracic aorta is inversely associated with coronary artery disease status and/or Type 1 diabetes status.

As aneurysms may develop and grow without any symptoms, physicians may recommend an imaging study to measure the size of the aorta in a subject. In some embodiments, if the subject is assessed to be at risk of aortic aneurysm using any one of the methods described herein, imaging may be performed on the subject. Imaging may be conducted using any method known in the art such as computed tomography (CT), magnetic resonance imaging (MRI), or echocardiography.

As described herein, it was found that the average diameter of ascending and descending aorta increased with age. In some embodiments, a subject's risk of aneurysm is increased when the subject's aortic diameter is found to be greater than that of a mean reference aortic diameter (e.g., the diameters disclosed in Table 2).

Assessment of a Subject's Thoracic Aortic Aneurysm Risk (Single Nucleotide Polymorphisms)

As described herein, it was determined that the diameters of the ascending thoracic aorta and the descending thoracic aorta are highly heritable: the single nucleotide polymorphism (SNP) heritability of the size of the ascending aorta was 63% (95% CI 60%-67%), while that of the descending aorta was 50% (95% CI 47%-53%).

In some embodiments, methods comprise assessing a subject's risk for an aneurysm of the ascending thoracic aorta or the descending thoracic aorta through detecting one or more SNPs in one or more of the genes listed in Tables 3 and 4, respectively. In some embodiments, the method comprises further assessing a subject's risk for an aneurysm of the ascending thoracic aorta or the descending thoracic aorta by detecting one more genes, as described herein.

As used herein, "assessing a subject's risk," refers to a process by which any type of test, assay, examination, result, readout, or interpretation that contributes to the determination of an increased or decreased probability that a subject has had, currently has, or will develop a particular disease, disorder, symptom, syndrome, or any condition related to health or bodily state, is performed. In some embodiments, the risk is a risk of an aneurysm, such as a thoracic aorta aneurysm (e.g., ascending thoracic aorta aneurysm or descending thoracic aorta aneurysm). Examples of disease outcomes include, but are not limited to survival, death, progression of aneurysm, or initiation of onset of an aneurysm in an otherwise disease-free subject. Assessing a subject's risk of a disease outcome also encompasses the concept of prognosis. A prognosis may be any assessment of the risk of disease outcome in an individual in which a particular disease has been diagnosed. Assessing a subject's risk further encompasses prediction of therapeutic response in which a treatment regimen is chosen based on the assessment. Assessing a subject's risk also encompasses a prediction of overall survival after diagnosis.

As used herein, "subject" includes human and non-human subjects. In some embodiments, the subject is human. In some embodiments, the human subject is less than 55 years of age. In some embodiments, the human is more than 55 years of age. In some embodiments, the human is more than 60 years, 65 years, 70 years, or 75 years of age. In other embodiments, the subject is a non-human. In some embodiments, the non-human subject is a non-human primate. In some embodiments, the non-human subject is an avian; a domestic household or farm animal such as a cat, dog, sheep, goat, cattle, horse or pig; a laboratory animal such as a mouse, rat or guinea pig; a fish; a reptile; a zoo animal; or a wild animal.

As disclosed herein, a subject's risk of aneurysm may be assessed, at least in part, by detecting one or more SNPs in one or more of the genes listed in Tables 3 and 4. In some embodiments, a subject's risk of aneurysm may be assessed by detecting one or more of the SNPs listed in Tables 3 and 4. SNPs may be detected by any method known in the art. For example, a SNP may be detected in a sample by hybridization-based methods, enzyme-based methods, or other post-amplifications methods. Examples of hybridization-based methods include, but are not limited to, dynamic allele-specific hybridization (DASH), the use of molecular beacons, and SNP microarrays (e.g., high-density oligonucleotide SNP arrays). Examples of enzyme-based methods include, but are not limited to, restriction fragment length polymorphism (RFLP), polymerase chain reaction (PCR)-based methods (e.g., amplification refractory mutation system PCR (ARMS-PCR), quantitative PCR (qPCR) with allele-targeted primer sets (Taq-MAMA)), the use of flap endonuclease (FEN) (e.g., the Invader assay, serial invasive signal amplification assay (SISAR)), primer extension methods (e.g., incorporation of fluorescently labeled dideoxynucleotides (ddNTP) or fluorescently labeled deoxynucleotides (dNTP) and then primer extension and detection, IPLEX SNP™, arrayed primer extension (APEX), APEX-2), use of 5'-nuclease (e.g., TAQMAN™ assay), and oligonucleotide ligation assays. Other post-amplification methods of SNP detection include, but are not limited to, single strand conformation polymorphism, temperature gradient gel electrophoresis (TGGE; also called temperature gradient capillary electrophoresis, TGCE), denaturing high performance liquid chromatography (DHPLC), high-resolution melting analysis, use of DNA mismatch-binding proteins, SNPLEX™, and the surveyor nuclease assay. In addition, next-generation sequencing (NGS) techniques (e.g., pyrosequencing) can also be used.

In some embodiments, detection of SNPs can be accomplished with sequencing using any sequencing means known in the art. Sequencing can include, for example, whole genome sequencing (WGS), plate-based single cell RNA sequencing, high-throughput single-cell RNA-seq and/or targeted nucleic acid profiling, or single nucleus RNA sequencing. In some embodiments, target genomic regions of interest may be enriched, such as from single cell sequencing libraries, prior to sequencing analysis.

Methods disclosed herein include detecting one or more SNPs in a sample from a subject. In some cases, the method may include detecting whether one or more SNPs in Tables 2 or 3 are present in a biological sample from a subject. Detecting may include, for example, contacting the biological sample with a set of probes to one or more SNPs, detecting binding to probes, amplifying genome regions comprising the SNPs using a set of amplification primers, sequencing genomic regions comprising or enriched for the SNPs, or any combination of these steps.

As used herein, the term "biological sample" is used in its broadest sense. A biological sample may be obtained from a subject (e.g., a human) or from components (e.g., tissues or cells) of a subject. The sample may be of any biological cell, tissue, or fluid from which SNPs may be assayed. Frequently, the sample will be a "clinical sample", i.e., a sample derived from a patient. Such samples include, but are not limited to, bodily fluids, e.g., urine, whole blood, blood plasma, saliva; tissue or fine needle biopsy samples; and archival samples with known diagnosis, treatment and/or outcome history. The term "biological sample" also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, and addition of reagents. In some embodiments, the biological sample is a whole blood sample. In some embodiments, the biological sample includes peripheral blood mononuclear cells (PBMCs) obtained from a subject. PBMCs can be extracted from whole blood using ficoll, a hydrophilic polysaccharide that separates layers of blood, and gradient centrifugation, which will separate the blood into a top layer of plasma, followed by a layer of PBMCs and a bottom fraction of polymorpho-nuclear cells (such as neutrophils and eosinophils) and erythrocytes.

The disclosure provides, in some aspects, a method of assessing a subject's risk for a descending thoracic aortic aneurysm by detecting a SNP in one or more of: PKN2, NAV1, GDF7, CCDC141, COL6A3, LMCD1, ULK4, FLNB, ZBTB20, MASP1, AFAP1, FIP1L1, FGF5, PDLIM5, FER, NKX2-5, MICA, CDKN1A, NT5E, ZNF292, TWIST1, TBX20, PI15, MAL2, SVIL, PLCE1, PCSK7, ADAMTS8, STAT6, ALDH2, ARHGEF40, MYH6, NFATC4, OTUB2, DISP2, FBN1, LOXL1, ADAMTS7, WWP2, TBC1D16, CTIF, DOT1L, ACTN4, SPTBN4, FBXO46, JAG1, and FHL1. In some embodiments, the SNP is detected in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or all 47 genes listed. In some embodiments, the SNP is detected in 1-5, 1-10, 1-15, 1-20, 1-25, 1-30, 1-35, 1-40, 1-45, 1-47, 5-10, 5-20, 5-25, 5-30, 5-35, 5-40, 5-45, 5-47, 10-15, 10-20, 10-25, 10-30, 10-35, 10-40, 10-45, 10-47, 15-20, 15-25, 15-30, 15-35, 15-40, 15-45, 15-47, 20-25, 20-30, 20-35, 20-40, 20-45, 20-47, 25-30, 25-35, 25-40, 25-45, 25-47, 30-35, 30-40, 30-45, 30-47, 35-40, 35-45, 35-47, 40-45, 40-47, or 45-47 of the genes listed.

The disclosure also provides, in some aspects, a method of assessing a subject's risk for an ascending thoracic aortic aneurysm, by detecting a SNP in one or more of: SPSB1, SF3A3, EDN2, FGGY, HMCN1, RYR2, OSR1, ZEB2, MBD5, FIGN, COL6A3, FGD5, ULK4, FLNB, LRIG1, GATA2, MASP1, FGF5, HAND2, ATP6AP1L, PCSK1, PPIC, PRDM6, KCNMB1, ADTRP, EDN1, CDKN1A, COL21A1, AIG1, ESR1, TBX20, HERPUD2, ELN, LIMK1, SEMA3D, MSRA, SLC25A37, PI15, ANGPT1, ENPP2, HAS2, FBXO32, TRAPPC9, LPAR1, CACNB2, ARIDSB, JMJD1C, PLCE1, NOC3L, ENTPD1, VTI1A, ABCC8, DCDC1, ANO1, NCAM1, ADAMTS8, RERG, ABCC9, USP15, LLPH, POC1B-GALNT4, CRADD, C12orf75, MED13L, FGF9, DLEU1, ASB2, DISP2, FBN1, THSD4, GNAO1, WWP2, HYDIN, CDH13, CBFA2T3, SMG6, CD68, MAP2K4, ATAD5, COPRS, PIEZO2, CCNE1, SLX4IP, SLC24A3, KCNE2, and TNRC6B. In some embodiments, the SNP is detected in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, or all 86 genes listed. In some embodiments, the SNP is detected in 1-5, 1-10, 1-20, 1-30, 1-40, 1-50, 1-60, 1-70, 1-80, 1-86, 5-10, 5-20, 5-30, 5-40, 5-50, 5-60, 5-70, 5-80, 5-86, 10-20, 10-30, 10-40, 10-50, 10-60, 10-70, 10-80, 10-86, 20-30, 20-40, 20-50, 20-60, 20-70, 20-80, 20-86, 30-40, 30-50, 30-60, 30-70, 30-80, 30-86, 40-50, 40-60, 40-70, 40-80, 40-86, 50-60, 50-70, 50-80, 50-86, 60-70, 60-80, 60-86, 70-80, 70-82, or 80-86 of the genes listed.

In some embodiments, the assessment of a subject's risk of thoracic aortic aneurysm (either ascending or descending) further comprises detecting a SNP in WWP2 (WW domain containing E3 ubiquitin protein ligase 2). For example, SNP rs62053262 is an expression quantitative trait locus (eQTL) in the aorta for WWP2 (Lonsdale et al. (2013) *Nat. Genet.* 45, 580-585); the rs62053262 G allele corresponds to reduced expression of WWP2 in aorta and smaller aortic size. WWP2 acts as an E3 ubiquitin ligase for PTEN (Maddika et al. (2011) *Nat. Cell Biol.* 13, 728-733) and has previously been shown to regulate cardiac fibrosis through modulation of SMAD signaling (Chen et al. (2019) *Nat. Commun.* 10, 1-19). As described herein, WWP2 expression has been found to be enriched in aortic vascular smooth muscle cells.

Polygenic Scoring

In some embodiments, a polygenic score is determined for a subject and is used, at least in part, to determine a subject's risk of an aortic aneurysm. In some embodiments, a subject's risk of an aortic aneurysm is increased if the subject's polygenic score is greater than that of a reference average polygenic score (e.g., an average polygenic score calculated from a population of subjects who do not have thoracic aortic aneurysms). In some embodiments, the risk of aortic aneurysm increases with increasing polygenic score and decreases with decreasing polygenic score. In some embodiments, a subject who has a polygenic score that is in the $55^{th}$, $60^{th}$, $65^{th}$, $70^{th}$, $75^{th}$, $80^{th}$, $85^{th}$, $90^{th}$, $91^{st}$, $92^{nd}$, $93^{rd}$, $94^{th}$, $95^{th}$, $96^{th}$, $97^{th}$, $98^{th}$, or $99^{th}$ percentile of the reference polygenic score, has a 1.5-fold, 2-fold, 2.5-fold, 3-fold, 3.5-fold, 4-fold, 4.5-fold, 5-fold, or greater risk of having an aortic aneurysm compared to a subject having a polygenic score that is in the $50^{th}$ percentile or lower.

Detection of Gene Expression

In some embodiments, a subject's risk is further assessed by detecting one or more genes and/or the expression level of one or more genes. Genes may be detected using any method known in the art (e.g., by PCR and/or sequencing).

In some embodiments, a subject's risk of descending thoracic aortic aneurysm is assessed, at least in part, by detecting one or more of the following genes: SVIL, MASP1, STAT6, AC003986.6, ACTN4, RNASE7, C2orf43, DISP2, CAPN12, FER, SIDT2, PLEKHJ1, AC012065.7, ADAMTS7, and PI15. In some embodiments, a subject's risk of descending thoracic aortic aneurysm is assessed, at least in part, by detecting 1, 2, 3, 4, 5, 6, 7, 8, 9, 10, 11, 12, 13, 14, or all 15 of the genes listed above. In some embodiments, a subject's risk of descending thoracic aortic aneurysm is assessed, at least in part, by detecting 1-2, 1-3, 1-4, 1-5, 1-6, 1-7, 1-8, 1-9, 1-10, 1-11, 1-12, 1-13, 1-14, 1-15, 2-5, 2-8, 2-10, 2-12, 2-14, 2-15, 3-5, 3-8, 3-10, 3-12, 3-14, 3-15, 4-5, 4-8, 4-10, 4-12, 4-14, 4-15, 5-8, 5-10, 5-12, -14, 5-15, 8-10, 8-12, 8-15, 10-12, 10-15, or 12-15 of the genes listed above.

In some embodiments, a subject's risk of descending thoracic aortic aneurysm is assessed by detecting SVIL (supervillin). SVIL encodes the supervillain protein, an F-actin and myosin II binding protein that localizes to and coordinates the action of invadosomes, cell surface extensions. Invadosomes promote matrix degradation through the localized release of extracellular matrix-lytic enzymes, such as disintegrin-and-metalloprotease domain-containing proteins and matrix metalloproteinases (Bhuwania et al. (2012) *J. Cell Sci.* 125, 2300-2314; Linder et al. (2011) *Annu. Rev. Cell Dev. Biol.* 27, 185-211).

In some embodiments, a subject's risk of ascending thoracic aortic aneurysm is further assessed, at least in part, by detecting one or more of the following genes: CTD-2337A12.1, RP11-254122.1, PRDM6, ULK4, AC008592.4, USP15, FIGN, AC092594.1, CBFA2T3, SRR, ABCC9, P11-589N15.2, ESR1, RP11-227D13.1, RP11-46107.1, AC008592.3, SMG6, GNAO1, RP11-441F2.5, THSD4, PI15, CDH13, RP11-981G7.2, FAM85B, TNRC6B, RP11-731K22.1, MTMR9, MASP1, HNRNPA1P16, MPPED2, SGK223, AF131215.8, CYP2C9, FLNB, RP11-713H12.1, NOC3L, RP11-470E16.1, ATP2B1, FHL3, SF3A3, ERI1, SNX24, RP11-830F9.6, RP11-467C18.1, AF131215.2, AF131215.9, MBD5, ACVR2A, FAM66A, RYR2, HSPD1, UTP11L, and RP11-145M4.3. In some embodiments, a subject's risk of ascending thoracic aortic aneurysm is assessed, at least in part, by detecting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or all 53 genes listed above. In some embodiments, a subject's risk of ascending thoracic aortic aneurysm is assessed, at least in part, by detecting 1-5, 1-10, 1-20, 1-30, 1-40, 1-50, 1-53, 5-10, 5-20, 5-30, 5-40, 5-50, 5-53, 10-20, 10-30, 10-40, 10-50, 10-53, 20-30, 20-40, 20-50, 20-53, 30-40, 30-50, 30-53, 40-45, 40-50, 40-53, 45-50, 45-53, or 50-53 of the genes listed above. In some embodiments, a subject's risk of ascending thoracic aortic aneurysm is assessed, at least in part, by detecting at least one of the following genes: ULK4 (UNC-51 like kinase 4), THSD4 (thrombospondin type 1 domain containing 4), and USP15 (ubiquitin specific peptidase 15).

Without wishing to be bound by theory, the increased expression of USP15 may lead to greater aortic diameter through the TGF-β signaling pathway, as USP15's protein product is a deubiquitinating enzyme that acts on the TGF-β receptor to increase TGF-β signaling. Therefore, in some embodiments, methods further comprise assessing a subject's level of TGF-β signaling using any method known in the art (e.g., through commercially available assays such as ELISAs, or other assays using antibodies that bind to bioactive TGF-β or pSMAD2 and/or pSMAD3).

Methods of Treatment

In some embodiments, methods further comprise treating a subject after assessing the subject's risk of an ascending thoracic aortic aneurysm or a descending thoracic aortic aneurysm. As used herein, "treating" refers to ameliorating at least one symptom of an aneurysm or slowing the progression of an aneurysm.

Treatments of aortic aneurysms depend on the cause, size, and location of the aneurysm. In some embodiments, the aneurysm is small enough that it may be managed with lifestyle changes or medicine (e.g., aspirin, blood pressure medications, statins). In some embodiments, the aneurysm is treated with surgery. The surgery may be an open surgical repair procedure, where a graft is added in place of the aneurysm, or an endovascular aneurysm repair procedure, where a stent graft is advanced through the aorta and then expanded in the location of the aneurysm to form a seal between the stent graft and the vessel wall, so that blood bypasses the aneurysm.

Kits for Detecting SNPs in a Sample

The present disclosure also provides kits for use in assessing a biological sample from a subject, for example, to assess the risk of aneurysm to the subject. The kits described herein may comprise means for collecting one or more biological samples (e.g., blood samples), means for DNA or RNA extraction, and/or means for detection of one or more of the 89 (ascending thoracic aorta) or 47 (descending thoracic aorta) SNPs described herein. For example, the kit may include one or more probes or primers for one or more of the SNPs listed in Table 3 or in Table 4.

In some embodiments, the kit is for assessing risk of a descending thoracic aortic aneurysm, and the kit includes one or more probes or primers for at least one of the following genes: SVIL, MASP1, STAT6, AC003986.6, ACTN4, RNASE7, C2orf43, DISP2, CAPN12, FER, SIDT2, PLEKHJ1, AC012065.7, ADAMTS7, and PI15. In certain embodiments, the kit comprises one or more probes or primers for all of the following genes: SVIL, MASP1, STAT6, AC003986.6, ACTN4, RNASE7, C2orf43, DISP2, CAPN12, FER, SIDT2, PLEKHJ1, AC012065.7, ADAMTS7, and PI15.

In some embodiments, the kit is for assessing risk of an ascending thoracic aortic aneurysm, and the kit includes one or more probes or primers for at least one of the following genes: CTD-2337A12.1, RP11-254122.1, PRDM6, ULK4, AC008592.4, USP15, FIGN, AC092594.1, CBFA2T3, SRR, ABCC9, P11-589N15.2, ESR1, RP11-227D13.1, RP11-46107.1, AC008592.3, SMG6, GNAO1, RP11-441F2.5, THSD4, PI15, CDH13, RP11-981G7.2, FAM85B, TNRC6B, RP11-731K22.1, MTMR9, MASP1, HNRNPA1P16, MPPED2, SGK223, AF131215.8, CYP2C9, FLNB, RP11-713H12.1, NOC3L, RP11-470E16.1, ATP2B1, FHL3, SF3A3, ERI1, SNX24, RP11-830F9.6, RP11-467C18.1, AF131215.2, AF131215.9, MBD5, ACVR2A, FAM66A, RYR2, HSPD1, UTP11L, and RP11-145M4.3. In certain embodiments, the kit comprises one or more probes or primers for all of the following genes: CTD-2337A12.1, RP11-254122.1, PRDM6, ULK4, AC008592.4, USP15, FIGN, AC092594.1, CBFA2T3, SRR, ABCC9, P11-589N15.2, ESR1, RP11-227D13.1, RP11-46107.1, AC008592.3, SMG6, GNAO1, RP11-441F2.5, THSD4, PI15, CDH13, RP11-981G7.2, FAM85B, TNRC6B, RP11-731K22.1, MTMR9, MASP1, HNRNPA1P16, MPPED2, SGK223, AF131215.8, CYP2C9, FLNB, RP11-713H12.1, NOC3L, RP11-470E16.1, ATP2B1, FHL3, SF3A3, ERI1, SNX24, RP11-830F9.6, RP11-467C18.1, AF131215.2, AF131215.9, MBD5, ACVR2A, FAM66A, RYR2, HSPD1, UTP11L, and RP11-145M4.3.

In some embodiments, the kit can comprise instructions for use in accordance with any of the methods described herein. The included instructions can comprise a description of gene expression measurement and interpretation of results. The kit may further comprise a description of selecting a subject suitable for treatment based on identifying whether that individual has, or is likely to have, an aortic aneurysm.

Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert may indicate that the kit is used for assessing the risk of an aortic aneurysm. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like.

Kits may optionally provide additional components such as buffers and interpretive information. Normally, the kit comprises a container and a label or package insert(s) on or associated with the container. In some embodiments, the invention provides articles of manufacture comprising contents of the kits described above.

The function and advantage of these and other embodiments of the present invention will be more fully understood from the Examples below. The following Examples are intended to illustrate the benefits of the present invention and to describe embodiments but are not intended to exemplify the full scope of the invention. Accordingly, it will be understood that the Examples are not meant to limit the scope of the invention.

EXAMPLES

Example 1: Genetic Analysis of Human Thoracic Aortic Dimension

Enlargement or aneurysm of the aorta can predispose a subject to dissection, an important cause of sudden death. By leveraging a deep learning architecture that was originally developed to recognize natural images, a model was trained to evaluate the dimensions of the ascending and descending thoracic aorta in cardiac magnetic resonance imaging. After manual annotation of just 116 samples, this model was applied to over 4.6 million images from the UK Biobank. Genome-wide association studies were then conducted in up to 39,688 individuals, revealing 89 loci associated with ascending and 47 with descending thoracic aortic diameter, of which 14 loci overlapped. Integration of common variation with transcriptome-wide analyses, rare-variant burden tests, and single nucleus RNA sequencing prioritized genes including SVIL, a gene highly expressed in vascular smooth muscle and significantly associated with the diameter of the descending aorta. A polygenic score for ascending aortic diameter was associated with a diagnosis of thoracic aortic aneurysm in the remaining 385,621 UK Biobank participants who did not undergo imaging (HR=1.43 per standard deviation; CI 1.32-1.54; P=$3.3 \cdot 10^{-20}$). Defining the genetic basis of the diameter of the aorta may enable the identification of asymptomatic individuals at risk for aneurysm or dissection and facilitate the prioritization of potential therapeutic targets for the prevention or treatment of aortic aneurysm. Finally, the results illustrate the potential for rapidly defining novel quantitative traits derived from a deep learning model, an approach that can be more broadly applied to biomedical imaging data.

It was hypothesized that the size of the thoracic aorta is a complex trait, with contributions from common genetic variants. Because the ascending and descending thoracic aorta have not only separate biological origins[10,11] but also separate clinical risk factors[12], these aortic regions were quantified independently.

Results

Semantic Segmentation of Aorta with Deep Learning

First, 116 cross-sectional cardiovascular magnetic resonance imaging (MRI) still-frame images at the level of the right pulmonary artery from the UK Biobank were manually annotated by a cardiologist. This annotation is known as semantic segmentation—the task of identifying and labeling all pixels that comprise an object in an image.

Those annotations were then used to train a deep learning model to perform the same semantic segmentation task. A U-Net architecture[13,14] was chosen because it has (a) an encoder that permits the model to recognize the image content (such as the presence of the aorta), and (b) skip-connections from some of the earliest layers to some of the deepest layers, enabling the fine-grained localization of that semantic label within the input image. This allows the model to precisely identify the boundaries of the aorta, permitting accurate measurements. As a form of transfer learning, this model's encoder had been pre-trained on ImageNet, which is a natural-image classification dataset. Therefore, instead of starting with random weights, the model was initialized with weights that are helpful for processing images, reducing the amount of manual annotation and model training necessary to achieve good results[13,15].

During training, 92 images were used for training and 24 as a validation set. The model achieved 96.5% pixel categorization accuracy for the ascending aorta and 94.1% for the descending aorta in the validation set. These were typical accuracies based on 10-fold cross validation (ascending aorta accuracy mean 95.2%, range 90.9%-97.2%; descending aorta accuracy mean 92.2%, range 88.9%-95.9%). Additionally, questions about inter-rater reliability between annotators were explored, models trained by different annotators were compared, and the dependence of model performance on the number of training examples was assessed (see below), with a visualization of model output in FIG. 6.

Figure 1:
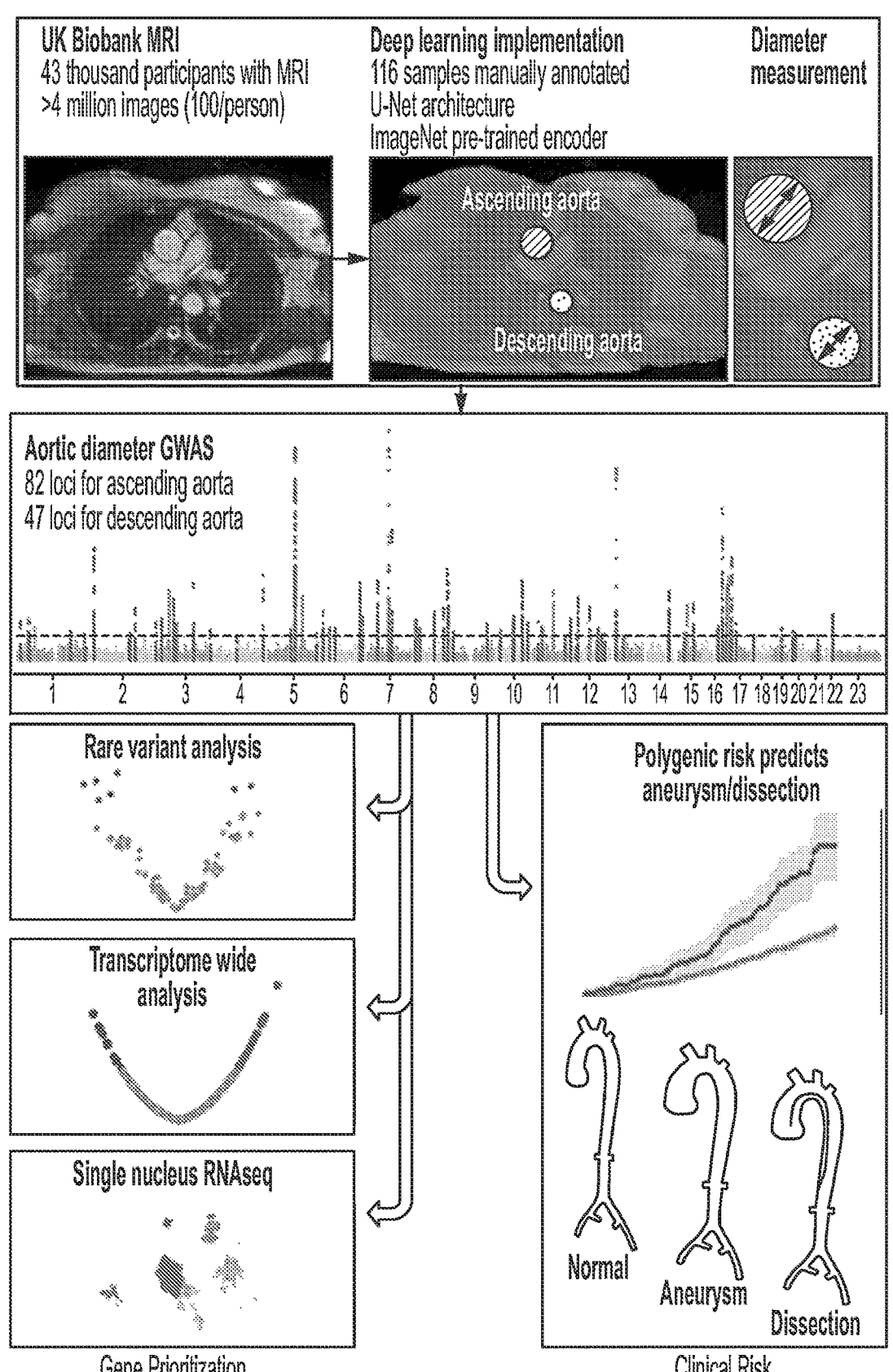
FIG. 1 illustrates a study overview.

Having trained a deep learning model to recognize the pixels of ascending and descending aorta using manually annotated images in the UK Biobank, the model was then applied to all aortic distensibility cardiovascular MRI data available in the UK Biobank (Table 1). The model was applied to 4,374,900 images from 43,243 participants who participated in the first UK Biobank imaging visit (FIG. 1). The deep learning model produced pixel labels with the same dimensions as the input MRI image (generally 240 px by 196 px).

TABLE 1

| Baseline characteristics of UK Biobank GWAS participants | | |
| --- | --- | --- |
| | Women | Men |
| N | 20,909 | 19,842 |
| Age at time of MRI | 64.0 (7.6) | 65.3 (7.8) |
| BMI (kg/m^2) | 25.9 (4.6) | 27.0 (3.9) |
| Height (cm) | 163 (6.2) | 176 (6.6) |
| Weight (kg) | 68.5 (12.7) | 83.6 (13.3) |
| Systolic blood pressure (mmHg) | 132 (18) | 139 (17) |
| Diastolic blood pressure (mmHg) | 79.4 (9.7) | 83.6 (9.6) |
| American standard drinks/week | 4.9 (5.5) | 6.1 (7.1) |
| Smoking status | | |
| Current | 1,055 (5%) | 1,470 (7%) |
| Never | 13,413 (64%) | 11,216 (57%) |
| Prefer not to answer | 37 (0%) | 35 (0%) |
| Previous | 6,400 (31%) | 7,118 (36%) |
| Unknown | 4 (0%) | 3 (0%) |
| Pack years of smoking | 3.6 (9.1) | 5.9 (13.0) |
| Ascending aorta diameter (cm) | 3.04 (0.31) | 3.32 (0.34) |
| Descending aorta diameter (cm) | 2.29 (0.18) | 2.55 (0.21) |

Demographic information is shown for UK Biobank participants with genetic and cardiac MRI data that passed quality control as detailed in the sample flow diagram in FIG. 10. For count data, values shown are N (%). For quantitative data, values shown are mean (SD).

Diameter Measurement and Quality Control

Classical computer vision algorithms were applied to post-process the deep learning output in order to measure the aortic diameter[16]. The elliptical minor axis was considered at its maximum size throughout the cardiac cycle to be the aortic diameter. The diameter of both the ascending and descending thoracic aorta were computed and these were treated as the primary phenotypes for subsequent analyses.

Quality control was then performed to exclude measurements from images in which the aorta was deemed to be incorrectly recognized according to one or more heuristics. In total, 42,518 UK Biobank participants had at least one measurement that passed quality control (40,363 with ascending aortic diameter and 41,415 with descending aortic diameter). 39,260 participants' measurements passed quality control for both ascending and descending aorta. A subset of 2,976 individuals who had undergone imaging at two different times were identified, and those data were used to confirm that the modeling approach yielded reproducible measurements (detailed below).

Characteristics of the Thoracic Aortic Diameter

The median diameter of the ascending aorta in women increased with age (FIG. 7), from 2.9 cm in women under the age of 55 to 3.1 cm in women over the age of 75. In men, the diameter ranged from 3.2 cm under the age of 55 to 3.4 cm over 75. These values are similar to those reported previously using MRI to measure ascending aortic diameter in other cohorts[17]. For the descending aorta, the median diameter in women increased from 2.2 cm in women under the age of 55 to 2.3 cm in women over the age of 75. In men, the diameter ranged from 2.4 cm under the age of 55 to 2.6 cm over 75. A standard reference table of aortic diameters by age and sex was computed and is available in Table 2. The ascending and descending aortic diameters were modestly correlated with one another (detailed below and shown in FIG. 8). The ascending aortic diameter had greater variance than that of the descending aorta (see below). This increase in the dispersion of the diameter of the ascending aorta compared to the descending thoracic aorta is consistent with prior observations[18].

TABLE 2

| Reference Ranges for Aortic Diameters | | | | | | | |
|---|---|---|---|---|---|---|---|
| Female | | | | Male | | | |
| Age Group | | | | | | | |
| <55 | 55-64 | 65-74 | >=75 | <55 | 55-64 | 65-74 | >=75 |
| N = 3237 | N = 8372 | N = 8743 | N = 1517 | N = 2657 | N = 6732 | N = 9028 | N = 2232 |
| Ascending Aorta, Diameter | | | | | | | |
| Mean (SD) 2.94 | 3.01 | 3.09 | 3.12 | 3.19 | 3.29 | 3.37 | 3.39 |
| (0.30) | (0.30) | (0.30) | (0.31) | (0.32) | (0.34) | (0.33) | (0.33) |
| Median 2.92 | 2.99 | 3.06 | 3.08 | 3.16 | 3.27 | 3.35 | 3.36 |
| [5%-95%] [2.49- | [2.56- | [2.64- | [2.66- | [2.70- | [2.77- | [2.86- | [2.91- |
| 3.47] | 3.54] | 3.62] | 3.69] | 3.72] | 3.88] | 3.95] | 3.97] |
| Missing N 123 | 262 | 272 | 67 | 167 | 423 | 631 | 210 |
| (%) (3.8%) | (3.1%) | (3.1%) | (4.4%) | (6.3%) | (6.3%) | (7.0%) | (9.4%) |
| Descending Aorta, Diameter | | | | | | | |
| Mean (SD) 2.19 | 2.26 | 2.33 | 2.35 | 2.44 | 2.52 | 2.58 | 2.60 |
| (0.16) | (0.17) | (0.18) | (0.19) | (0.19) | (0.20) | (0.20) | (0.22) |
| Median 2.18 | 2.26 | 2.32 | 2.34 | 2.44 | 2.51 | 2.57 | 2.59 |
| [5%-95%] [1.94- | [2.00- | [2.06- | [2.06- | [2.15- | [2.22- | [2.26- | [2.28- |
| 2.46] | 2.55] | 2.64] | 2.69] | 2.75] | 2.86] | 2.92] | 2.97] |
| Missing N 78 | 212 | 288 | 63 | 66 | 145 | 191 | 60 |
| (%) (2.4%) | (2.5%) | (3.3%) | (4.2%) | (2.5%) | (2.2%) | (2.1%) | (2.7%) |

Correlation Between Aortic Diameter and Other Traits

The relationship between the aortic diameter and other anthropometric measurements were characterized in the UK Biobank (FIG. 9A, left). The diameter of ascending aorta was strongly positively correlated with traits such as weight, height, and blood pressure, as well as traits that correspond with larger body size such as greater FEV1, hand grip strength, and food and alcohol consumption, consistent with previous reports[19]. It was strongly inversely correlated with heart rate and biomarkers including cholesterol, testosterone, and sex hormone binding globulin. Similar associations were observed for the descending aortic diameter (FIG. 9A, right).

The association between aortic size and PheCode-based disease labels[20] was also analyzed. The size of the ascending aorta was associated with cardiovascular diseases such as hypertension, aortic aneurysm, valvular disorders, and cardiac arrhythmias, as well as other traits including varicose veins, obesity, and osteoarthritis, several of which correspond to previous clinical observations[21]. Descending thoracic aortic size was associated with obesity, hypertension, and varicose veins. Notably, coronary artery disease was inversely associated with descending aortic diameter ($P=1.7 \cdot 10^{-6}$), but not associated with ascending diameter ($P=0.6$). In addition, the descending aortic size was directly associated with cholelithiasis and headache, and inversely associated with type 1 diabetes as has previously been observed[22,23] (FIG. 9B, left). While the ascending and descending aortic diameters shared similar correlations with most continuous traits, their relationships with PheCode-based disease phenotypes were more independent (FIG. 9B, right).

GWAS of Thoracic Aortic Diameter

Next, it was sought to understand the common genetic basis for variation in the size of the ascending and descending thoracic aorta in the UK Biobank. Participants were excluded from genetic analysis if they had an aortic diameter greater than 5 cm, a known history of aortic disease, or genetic data that did not pass sample-level quality control (FIG. 10). 38,694 participants had data that passed quality control and contributed to genetic analyses of the ascending aortic diameter, and 39,688 participants contributed to analyses of the descending aortic diameter (Table 1).

It was confirmed that both traits were highly heritable: the single nucleotide polymorphism (SNP) heritability of the size of the ascending aorta was 63% (95% CI 60%-67%), while that of the descending aorta was 50% (95% CI 47%-53%).

Figure 2A:
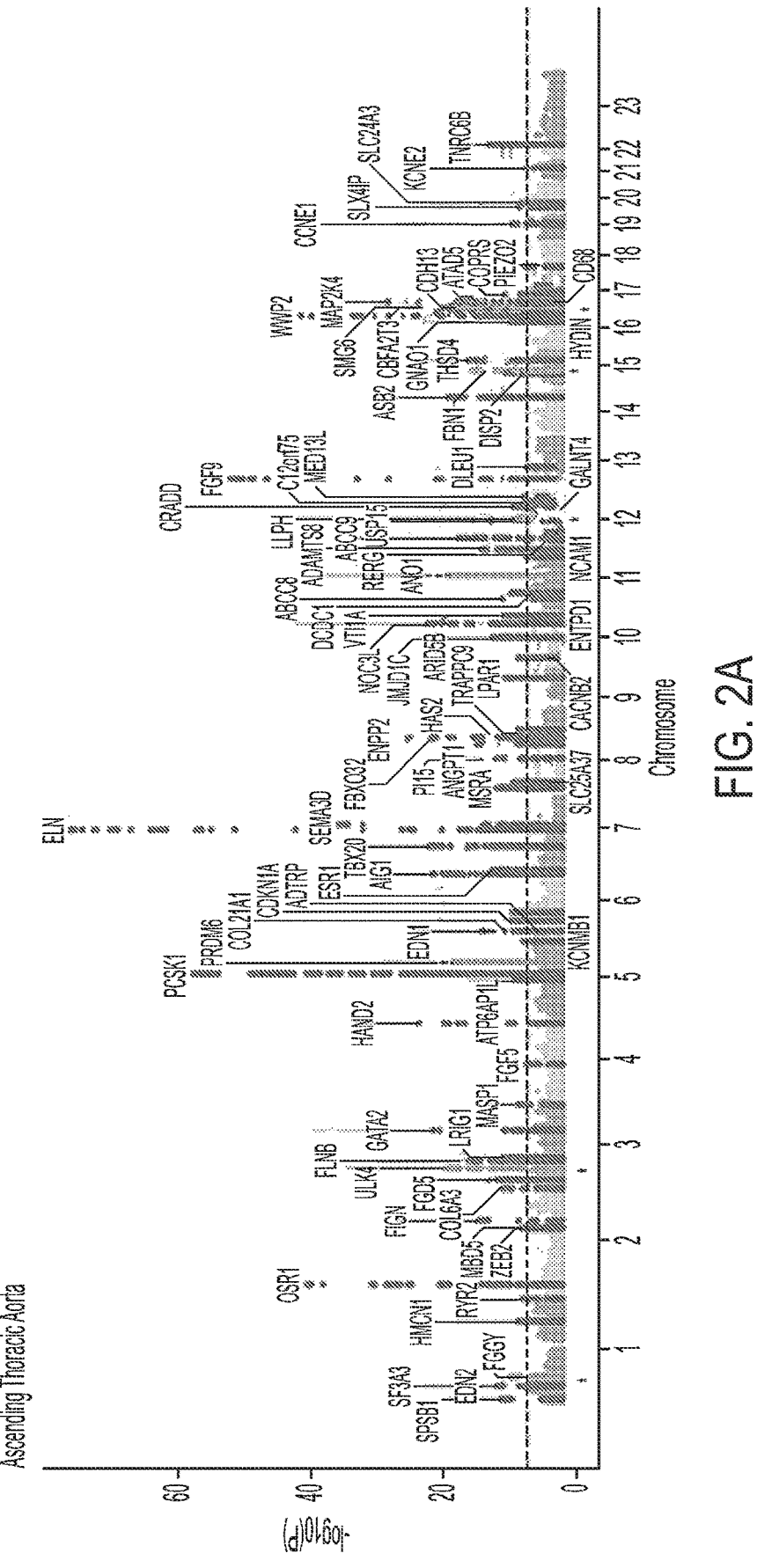
FIGS. 2A-2C illustrate genome-wide association study results.
Figure 2B:
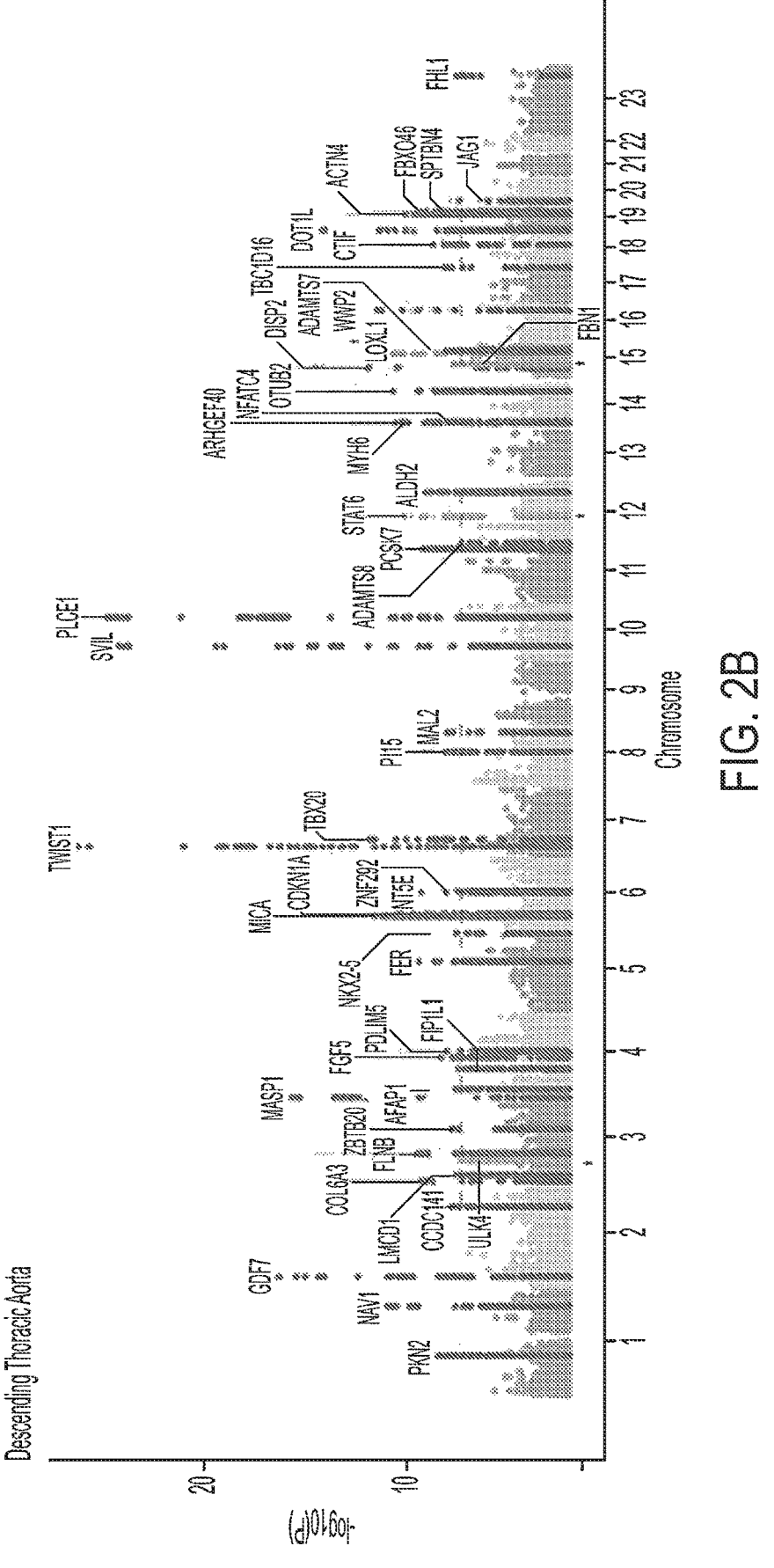
Figure 2C:
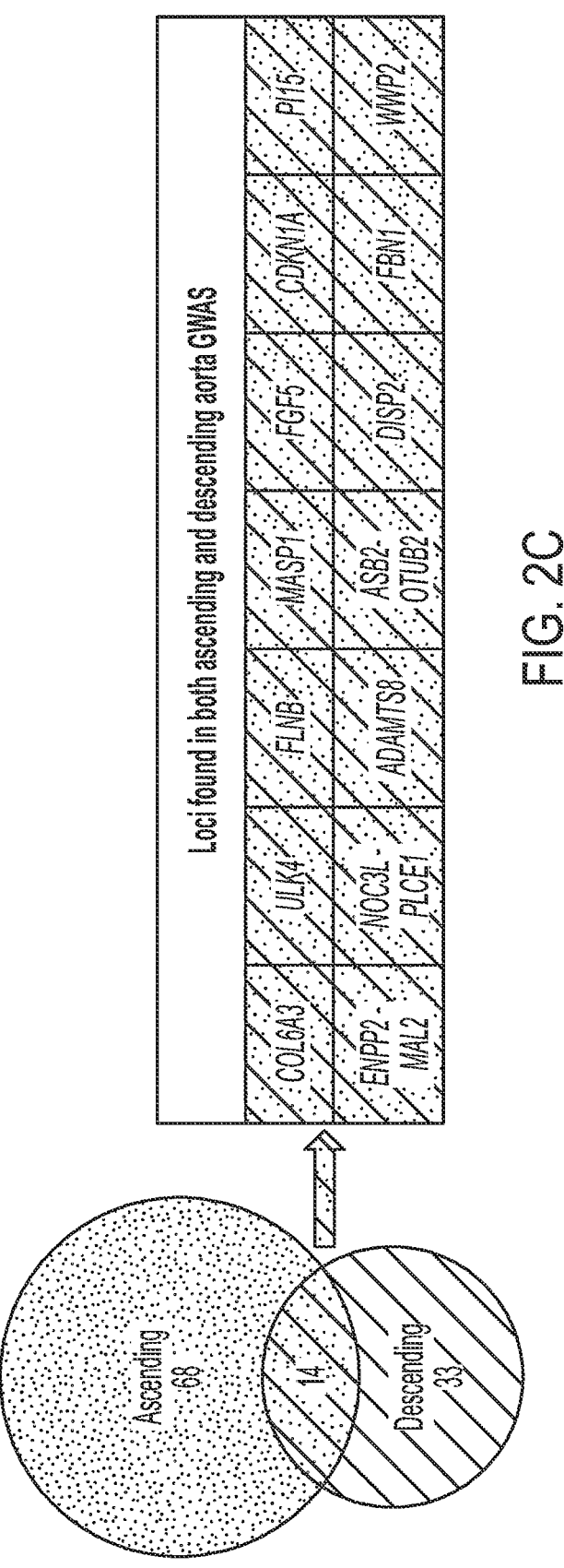

Genome-wide association studies (GWAS) of these two traits were then conducted, testing 16.7 million genotyped and imputed SNPs with MAF>0.001. 82 independent loci were identified that are associated with the diameter of the ascending aorta at a commonly used genome-wide significance threshold ($P<5 \cdot 10^{-8}$) (Table 3, FIGS. 2A and 2B). Of these, 75 loci were novel. In the descending aorta, 47 genome-wide significant loci were identified, of which 43 were novel and one was located on the X chromosome. In total, 115 loci were identified, of which 14 were associated at genome-wide significance with both traits (FIG. 2C). Test statistic inflation was observed in QQ plots (FIG. 11) and the low ldsc intercepts indicated that this inflation was consistent with polygenicity rather than confounding[24]. One autosomal lead SNP deviated from Hardy-Weinberg Equilibrium (HWE) with $P<1 \cdot 10^{-6}$ (rs10744777 near ALDH2 with HWE $P=1.9 \cdot 10^{-8}$ within the GWAS sample); however, other genome-wide significant SNPs within the locus did not violate HWE, including the nearby rs4766897 (50 kb away) with HWE $P=0.02$ and GWAS $P=6.6 \cdot 10^{-9}$. As a sensitivity analysis, the GWAS was also repeated in a European-only subset of the UK Biobank (see below). In the European-only analysis, the same SNP (rs10744777) remained the lead SNP for the locus (GWAS $P=2.7 \cdot 10^{-8}$) with HWE $P=0.91$.

TABLE 3

| GWAS Loci: Ascending thoracic aorta | | | | | | | | | |
|---|---|---|---|---|---|---|---|---|---|
| SNP | CHR | BP | Effect Allele | Other Allele | EAF | INFO | BETA | P Value | Nearest Gene |
| rs2871651 | 1 | 9434969 | C | T | 0.58 | 0.99 | −0.036 | 5.80E−12 | SPSB1 |
| rs67631072 | 1 | 38461821 | C | T | 0.45 | 0.99 | −0.072 | 1.40E−12 | SF3A3 |
| rs3768274 | 1 | 41951383 | C | T | 0.50 | 0.98 | 0.048 | 6.70E−12 | EDN2 |
| rs11207420 | 1 | 59646524 | G | A | 0.73 | 1.00 | 0.099 | 1.30E−10 | FGGY |
| rs66478136 | 1 | 59887078 | T | A | 0.70 | 0.96 | 0.040 | 3.40E−10 | FGGY |
| rs72727759 | 1 | 185663021 | T | C | 0.74 | 0.99 | −0.058 | 2.10E−09 | HMCN1 |
| rs35534155 | 1 | 237207943 | A | ATT | 0.19 | 0.90 | 0.062 | 9.70E−09 | RYR2 |
| rs6707048 | 2 | 19720468 | T | C | 0.32 | 1.00 | 0.034 | 3.50E−41 | OSR1 |
| rs138963986 | 2 | 145752940 | G | A | 0.93 | 0.96 | −0.046 | 4.00E−08 | ZEB2 |
| rs12992231 | 2 | 148799710 | C | A | 0.64 | 1.00 | −0.046 | 8.10E−09 | MBD5 |
| rs16849225 | 2 | 164906820 | C | T | 0.77 | 1.00 | −0.033 | 1.90E−15 | FIGN |
| rs12052878 | 2 | 238227594 | G | A | 0.69 | 1.00 | −0.059 | 1.10E−11 | COL6A3 |
| rs11712199 | 3 | 14858226 | G | A | 0.91 | 0.99 | 0.070 | 1.40E−12 | FGD5 |
| rs9847006 | 3 | 41755359 | T | C | 0.83 | 1.00 | 0.065 | 3.80E−20 | ULK4 |
| rs545996255 | 3 | 58100423 | G | GT | 0.70 | 0.97 | −0.048 | 5.10E−18 | FLNB |
| rs2306272 | 3 | 66434643 | T | C | 0.71 | 1.00 | −0.111 | 1.50E−11 | LRIG1 |
| rs55914222 | 3 | 128202943 | G | C | 0.97 | 0.99 | 0.058 | 3.90E−22 | GATA2 |
| rs1108450 | 3 | 186995297 | T | G | 0.83 | 0.99 | −0.075 | 1.50E−09 | MASP1 |
| rs16998073 | 4 | 81184341 | A | T | 0.71 | 1.00 | 0.044 | 3.50E−08 | FGF5 |
| rs67846163 | 4 | 174656889 | A | G | 0.77 | 0.99 | −0.043 | 2.30E−24 | HAND2 |
| rs73766539 | 5 | 81722919 | C | T | 0.79 | 1.00 | 0.048 | 6.80E−10 | ATP6AP1L |
| rs72787618 | 5 | 95591331 | A | G | 0.63 | 0.99 | −0.080 | 3.20E−58 | PCSK1 |
| rs35128692 | 5 | 122369014 | G | T | 0.65 | 0.99 | 0.050 | 1.30E−09 | PPIC |
| rs17470137 | 5 | 122531347 | G | A | 0.73 | 1.00 | 0.744 | 5.80E−19 | PRDM6 |
| rs76888257 | 5 | 169809901 | C | T | 0.90 | 1.00 | 0.048 | 1.30E−08 | KCNMB1 |
| rs496236 | 6 | 11641601 | A | G | 0.46 | 1.00 | −0.060 | 7.20E−10 | ADTRP |
| rs1630736 | 6 | 12295987 | C | T | 0.54 | 0.99 | −0.035 | 8.30E−15 | EDN1 |
| rs12199346 | 6 | 36641546 | C | A | 0.76 | 1.00 | 0.049 | 2.00E−10 | CDKN1A |
| rs6459130 | 6 | 56055564 | G | T | 0.44 | 1.00 | 0.042 | 3.30E−10 | COL21A1 |

TABLE 3-continued

| | | | | | | | | | |
|---|---|---|---|---|---|---|---|---|---|
| GWAS Loci: Ascending thoracic aorta | | | | | | | | | |
| SNP | CHR | BP | Effect Allele | Other Allele | EAF | INFO | BETA | P Value | Nearest Gene |
| rs1570350 | 6 | 143592386 | A | G | 0.56 | 0.99 | 0.045 | 2.90E-22 | AIG1 |
| rs13203975 | 6 | 152333104 | G | A | 0.89 | 0.99 | 0.044 | 3.30E-13 | ESR1 |
| rs79215950 | 7 | 35277067 | G | A | 0.62 | 1.00 | -0.128 | 7.80E-23 | TBX20 |
| rs73087411 | 7 | 35532991 | C | T | 0.82 | 0.98 | 0.079 | 4.80E-10 | HERPUD2 |
| rs6974735 | 7 | 73428222 | A | G | 0.55 | 1.00 | 0.031 | 7.90E-77 | ELN |
| rs1091813 | 7 | 73489736 | C | T | 0.09 | 0.99 | -0.049 | 9.10E-09 | LIMK1 |
| rs1583081 | 7 | 85034227 | G | T | 0.58 | 1.00 | -0.056 | 2.40E-36 | SEMA3D |
| rs483916 | 8 | 9793601 | A | C | 0.48 | 0.99 | 0.041 | 1.30E-12 | MSRA |
| rs11785562 | 8 | 23391493 | G | A | 0.80 | 0.97 | -0.093 | 3.70E-10 | SLC25A37 |
| rs9721183 | 8 | 75781818 | C | T | 0.63 | 0.95 | 0.055 | 1.40E-14 | PI15 |
| rs16876090 | 8 | 108363596 | G | A | 0.91 | 0.99 | 0.056 | 1.40E-15 | ANGPT1 |
| rs41475846 | 8 | 108508700 | G | A | 0.85 | 0.99 | -0.044 | 2.20E-09 | ANGPT1 |
| rs562291939 | 8 | 120709336 | T | C | 1.00 | 0.80 | 0.062 | 5.10E-26 | ENPP2 |
| rs10111085 | 8 | 122646152 | G | T | 0.71 | 0.99 | 0.054 | 2.00E-12 | HAS2 |
| rs34557926 | 8 | 124607159 | C | T | 0.63 | 0.99 | -0.082 | 2.90E-22 | FBXO32 |
| rs112342612 | 8 | 141047976 | AAC | A | 0.40 | 0.95 | 0.036 | 3.30E-09 | TRAPPC9 |
| rs4978966 | 9 | 113662374 | C | T | 0.79 | 1.00 | -0.043 | 2.50E-11 | LPAR1 |
| rs1757223 | 10 | 18514999 | G | A | 0.24 | 0.99 | 0.037 | 2.00E-09 | CACNB2 |
| rs16916931 | 10 | 63813744 | A | T | 0.69 | 0.98 | -0.039 | 1.20E-12 | ARID5B |
| rs7090111 | 10 | 65077994 | C | G | 0.58 | 1.00 | 0.042 | 3.10E-13 | JMJD1C |
| rs147121076 | 10 | 95924521 | T | G | 0.98 | 0.95 | 0.109 | 2.40E-09 | PLCE1 |
| rs71482305 | 10 | 96119130 | C | T | 0.84 | 1.00 | -0.032 | 6.30E-23 | NOC3L |
| rs1340837 | 10 | 97542035 | A | G | 0.59 | 1.00 | 0.055 | 4.90E-09 | ENTPD1 |
| rs11196083 | 10 | 114500004 | G | T | 0.77 | 1.00 | -0.044 | 1.60E-11 | VTI1A |
| rs77889556 | 11 | 17498057 | G | A | 0.83 | 0.91 | -0.082 | 8.40E-12 | ABCC8 |
| rs3741025 | 11 | 30851976 | C | T | 0.43 | 0.99 | 0.053 | 1.70E-10 | DCDC1 |
| rs111412755 | 11 | 69819139 | C | T | 0.91 | 0.98 | 0.042 | 7.80E-20 | ANO1 |
| 11:70022262__CT_C | 11 | 70022262 | CT | C | 0.57 | 0.85 | 0.187 | 2.10E-15 | ANO1 |
| rs12286728 | 11 | 113022450 | G | C | 0.90 | 1.00 | 0.275 | 3.10E-08 | NCAM1 |
| rs747249 | 11 | 130271647 | A | G | 0.36 | 0.99 | -0.045 | 1.30E-12 | ADAMTS8 |
| rs61907983 | 12 | 15448631 | C | T | 0.91 | 0.97 | 0.063 | 2.60E-08 | RERG |
| rs2307024 | 12 | 22005003 | T | G | 0.59 | 0.99 | -0.063 | 2.30E-18 | ABCC9 |
| rs56298756 | 12 | 62777565 | G | T | 0.89 | 1.00 | -0.072 | 8.40E-16 | USP15 |
| rs10400419 | 12 | 66389968 | T | C | 0.45 | 0.95 | 0.078 | 2.50E-09 | LLPH |
| rs7302816 | 12 | 89950320 | A | C | 0.80 | 0.98 | 0.053 | 2.50E-08 | POC1B-GALNT4 |
| rs2363080 | 12 | 94140463 | C | G | 0.56 | 0.99 | 0.044 | 4.30E-10 | CRADD |
| rs11112482 | 12 | 105738183 | C | G | 0.77 | 0.99 | -0.035 | 2.10E-08 | C12orf75 |
| rs61937394 | 12 | 116756670 | T | G | 0.81 | 0.91 | -0.039 | 1.60E-08 | MED13L |
| rs7994761 | 13 | 22871446 | A | G | 0.78 | 0.99 | 0.034 | 1.30E-52 | FGF9 |
| rs2687941 | 13 | 50760363 | T | C | 0.55 | 0.99 | 0.040 | 3.70E-08 | DLEU1 |
| rs4905134 | 14 | 94459845 | A | G | 0.50 | 0.99 | 0.051 | 5.40E-20 | ASB2 |
| rs3803359 | 15 | 40662748 | G | A | 0.83 | 1.00 | 0.057 | 7.50E-09 | DISP2 |
| rs2118181 | 15 | 48915884 | T | C | 0.90 | 0.99 | -0.036 | 2.30E-16 | FBN1 |
| rs1441358 | 15 | 71612514 | T | G | 0.66 | 1.00 | -0.072 | 8.10E-17 | THSD4 |
| rs369339295 | 16 | 56322945 | A | AAG | 0.68 | 0.97 | 0.048 | 1.50E-10 | GNAO1 |
| rs62053262 | 16 | 69969299 | C | G | 0.95 | 0.99 | 0.099 | 4.00E-42 | WWP2 |
| rs546590249 | 16 | 71104575 | A | C | 0.99 | 0.38 | 0.040 | 2.70E-08 | HYDIN |
| rs7500448 | 16 | 83045790 | A | G | 0.75 | 0.98 | -0.058 | 2.90E-11 | CDH13 |
| rs16965180 | 16 | 88989862 | A | G | 0.65 | 0.99 | 0.062 | 1.20E-21 | CBFA2T3 |
| 17:2088848_CCAGA_C | 17 | 2088848 | CCAGA | C | 0.68 | 1.00 | 0.034 | 6.80E-24 | SMG6 |
| rs78180894 | 17 | 7483662 | G | C | 0.93 | 0.94 | -0.046 | 6.60E-09 | CD68 |
| rs7215383 | 17 | 12182246 | A | G | 0.25 | 0.99 | -0.046 | 4.90E-29 | MAP2K4 |
| rs6505216 | 17 | 29206421 | G | T | 0.77 | 0.92 | -0.033 | 2.00E-11 | ATAD5 |
| rs76954792 | 17 | 30033514 | C | T | 0.77 | 0.98 | -0.059 | 3.90E-09 | COPRS |
| rs264203 | 18 | 10882121 | A | C | 0.38 | 0.99 | 0.070 | 2.50E-08 | PIEZO2 |
| rs7257694 | 19 | 30314666 | C | T | 0.60 | 0.99 | 0.065 | 3.00E-10 | CCNE1 |
| rs3063286 | 20 | 10488552 | T | TTA | 0.47 | 0.94 | -0.048 | 2.20E-09 | SLX4IP |
| rs6075516 | 20 | 19455985 | G | A | 0.75 | 0.97 | -0.111 | 6.30E-09 | SLC24A3 |
| rs28451064 | 21 | 35593827 | G | A | 0.87 | 0.96 | 0.058 | 4.20E-08 | KCNE2 |
| rs4402860 | 22 | 40554445 | A | T | 0.80 | 1.00 | -0.075 | 7.30E-14 | TNRC6B |

TABLE 4

| | | | | | | | | | Nearest |
| SNP | CHR | BP | Effect Allele | Other Allele | EAF | INFO | BETA | P Value | Gene |
|---|---|---|---|---|---|---|---|---|---|
| rs35584696 | 1 | 89145392 | C | CT | 0.44 | 1.00 | −0.033 | 3.80E−09 | PKN2 |
| rs527725 | 1 | 201752429 | A | C | 0.60 | 0.97 | 0.036 | 1.20E−11 | NAV1 |
| rs7255 | 2 | 20878820 | T | C | 0.45 | 1.00 | 0.045 | 4.80E−17 | GDF7 |
| rs202119031 | 2 | 179744659 | CAG | C | 0.87 | 1.00 | 0.045 | 3.80E−08 | CCDC141 |
| rs7580831 | 2 | 238219499 | C | A | 0.68 | 1.00 | −0.037 | 5.20E−10 | COL6A3 |
| rs11707002 | 3 | 8580237 | C | G | 0.55 | 0.99 | 0.031 | 2.40E−08 | LMCD1 |
| rs5848609 | 3 | 41802815 | G | GTTA | 0.84 | 0.99 | −0.041 | 4.50E−08 | ULK4 |
| rs56004178 | 3 | 58101471 | G | A | 0.70 | 0.99 | 0.038 | 3.10E−10 | FLNB |
| rs2055981 | 3 | 114203969 | T | C | 0.36 | 0.99 | −0.032 | 1.70E−08 | ZBTB20 |
| rs698099 | 3 | 186987941 | G | A | 0.17 | 1.00 | 0.060 | 2.20E−16 | MASP1 |
| rs6855532 | 4 | 7908237 | C | T | 0.57 | 1.00 | 0.030 | 2.70E−08 | AFAP1 |
| rs60991988 | 4 | 54801228 | T | G | 0.89 | 0.99 | −0.047 | 3.70E−08 | FIP1L1 |
| rs3733336 | 4 | 81207963 | A | G | 0.64 | 0.90 | −0.034 | 5.10E−09 | FGF5 |
| rs6853490 | 4 | 95544718 | A | G | 0.58 | 0.98 | 0.031 | 1.00E−08 | PDLIM5 |
| rs9285863 | 5 | 108071655 | T | C | 0.66 | 0.99 | −0.036 | 4.20E−10 | FER |
| rs35564079 | 5 | 172670611 | C | CT | 0.71 | 0.97 | −0.035 | 3.00E−08 | NKX2-5 |
| rs2853975 | 6 | 31382717 | A | T | 0.71 | 0.99 | −0.042 | 2.60E−12 | MICA |
| rs733590 | 6 | 36645203 | T | C | 0.65 | 1.00 | −0.035 | 2.20E−10 | CDKN1A |
| rs4707174 | 6 | 85987918 | A | C | 0.70 | 0.98 | −0.036 | 5.30E−10 | NT5E |
| 6:87836772__ACACACACACC_A | 6 | 87836772 | ACACACACACC | A | 0.65 | 0.77 | 0.035 | 3.40E−08 | ZNF292 |
| rs2107595 | 7 | 19049388 | G | A | 0.84 | 0.99 | 0.079 | 5.80E−27 | TWIST1 |
| rs343044 | 7 | 35508859 | A | G | 0.20 | 0.99 | −0.047 | 1.50E−12 | TBX20 |
| rs36086322 | 8 | 75735030 | C | T | 0.93 | 1.00 | 0.059 | 8.40E−09 | PI15 |
| rs574214679 | 8 | 120244723 | A | G | 1.00 | 0.71 | 0.413 | 1.10E−08 | MAL2 |
| rs10740811 | 10 | 30167754 | G | A | 0.41 | 1.00 | 0.057 | 6.40E−25 | SVIL |
| rs2901761 | 10 | 95895127 | G | A | 0.59 | 1.00 | 0.058 | 1.70E−25 | PLCE1 |
| 11:117085914_CTTA_C | 11 | 117085914 | CTTA | C | 0.94 | 1.00 | −0.068 | 6.60E−10 | PCSK7 |
| rs10894192 | 11 | 130266117 | T | A | 0.42 | 0.98 | −0.030 | 4.90E−08 | ADAMTS8 |
| rs4759275 | 12 | 57525756 | G | A | 0.58 | 1.00 | 0.035 | 8.10E−11 | STAT6 |
| rs10744777 | 12 | 112233018 | T | C | 0.66 | 1.00 | −0.035 | 8.80E−10 | ALDH2 |
| rs12889267 | 14 | 21542766 | A | G | 0.83 | 1.00 | 0.048 | 2.90E−11 | ARHGEF40 |
| rs422068 | 14 | 23864804 | T | C | 0.64 | 1.00 | 0.036 | 1.10E−09 | MYH6 |
| rs12590407 | 14 | 24835115 | G | A | 0.29 | 1.00 | 0.034 | 1.40E−08 | NFATC4 |
| rs12890024 | 14 | 94469801 | A | G | 0.62 | 0.98 | 0.038 | 2.10E−11 | OTUB2 |
| rs12913300 | 15 | 40655444 | C | T | 0.83 | 1.00 | −0.052 | 1.20E−12 | DISP2 |
| rs17352842 | 15 | 48694211 | C | T | 0.81 | 1.00 | −0.037 | 2.20E−08 | FBN1 |
| rs1048661 | 15 | 74219546 | G | T | 0.66 | 0.99 | −0.038 | 2.30E−11 | LOXL1 |
| rs116901435 | 15 | 79059695 | C | T | 0.58 | 0.98 | −0.032 | 7.90E−09 | ADAMTS7 |
| rs62053262 | 16 | 69969299 | C | G | 0.95 | 0.99 | 0.087 | 3.50E−12 | WWP2 |
| rs894871 | 17 | 77910932 | A | G | 0.68 | 0.98 | −0.032 | 7.50E−09 | TBC1D16 |
| rs8094206 | 18 | 46317137 | G | A | 0.89 | 0.98 | 0.052 | 2.00E−09 | CTIF |
| rs55678414 | 19 | 2177625 | T | G | 0.94 | 1.00 | 0.088 | 6.70E−15 | DOT1L |
| rs2303040 | 19 | 39138608 | T | C | 0.51 | 0.99 | −0.037 | 9.50E−11 | ACTN4 |
| rs1673096 | 19 | 41042755 | A | G | 0.52 | 0.99 | 0.031 | 3.20E−08 | SPTBN4 |
| rs11668847 | 19 | 46210365 | T | G | 0.48 | 0.98 | 0.033 | 5.30E−10 | FBXO46 |
| rs76496822 | 20 | 10687240 | G | T | 0.96 | 0.99 | −0.072 | 4.00E−08 | JAG1 |
| rs76530933 | 23 | 135204774 | G | T | 0.73 | 0.94 | −0.030 | 3.10E−08 | FHL1 |

The lead SNPs from the GWAS for the diameter of the ascending (Table 3) and descending (Table 4) thoracic aorta. SNP = the rsID of the valiant, where available. BP = genomic position, keyed to GRCh37. EAF = Effect allele frequency. INFO = imputation INFO score. BETA = effect size per effect allele on the inverse normal transformed trait.

Previous analyses of thoracic aortic phenotypes including aortic root diameter, ascending aortic dissection, or thoracic aortic aneurysm have identified only 16 genome-wide significant loci; of these, nine achieved genome-wide significance in the study, including all three loci that have been associated with thoracic aortic dissection (near FBN1, ULK4, and the STATE/LRP1 locus)[25-29].

It was sought to replicate the UK Biobank GWAS findings in 3,287 participants from the Framingham Heart Study (FHS) who had genotyping data and cross-sectional imaging of the ascending and descending thoracic aorta by computed tomography[30,31]. Since the FHS sample size was an order of magnitude smaller than the discovery population in the UK Biobank, directional agreement was focused on. Of the 82 lead SNPs in the ascending aorta, 72 were identified in the FHS dataset. 60 of these 72 SNPs were directionally consistent in both datasets (two-tailed binomial P=8.1·10⁻⁹; FIG. 12A). 41 of the 46 autosomal lead SNPs from the descending aorta were identified in FHS, and 36/41 were directionally consistent (two-tailed binomial P=7.8·10⁻⁷;

FIG. 12B). Thus, despite comprising a significantly smaller sample, as well as using a different imaging modality and measurement technique, the FHS results were aligned with the findings from the UK Biobank.

Genetic Correlation with Other Phenotypes

Genetic correlation was used to gain insight into the relationship between aortic diameter and other cardiovascular and anthropometric phenotypes in the UK Biobank. The ascending and descending aortic phenotypes had a genetic correlation with one another of 0.48 (95% CI 0.45-0.52) as estimated by BOLT-REML[32,33]. Linkage disequilibrium (LD) score regression was used to assess genetic correlation between the aortic traits and up to 281 additional quantitative phenotypes from the UK Biobank that were precomputed by the Neale Lab[34,35]. As expected, positive genetic correlations were observed between aortic size and anthropometric measures such as height and weight, as well as related phenotypes such as blood pressure (FIGS. 13A-13B and 14).

Given the observed genetic correlation with blood pressure (ldsc rg 0.30 for ascending aortic diameter and 0.17 for descending aortic diameter), the overlap between the aortic loci and genome-wide significant blood pressure loci was also surveyed. Ten of the 82 lead SNPs for ascending aortic diameter were within 500 kb of a lead SNP from a recent GWAS for blood pressure, as were six of the 47 descending aortic lead SNPs[36]. Of the nine adrenoceptor genes, which encode the molecular targets of alpha- and beta-blocking medicines, none were within 500 kb of a lead SNP from the study.

Transcriptome-Wide Association Study

To gain more insight into the GWAS loci themselves, three approaches were taken to prioritize genes at each locus and to link those genes to relevant cell types. First, a transcriptome wide association study (TWAS) was conducted, linking predicted gene expression in aorta (based on GTEx v7) with aortic size (FIG. 3A)[37,38]. 53 transcripts were identified that were significantly associated with the diameter of the ascending aorta and 15 with the descending aorta at $P<5\cdot10^{-8}$.

Figure 3A:
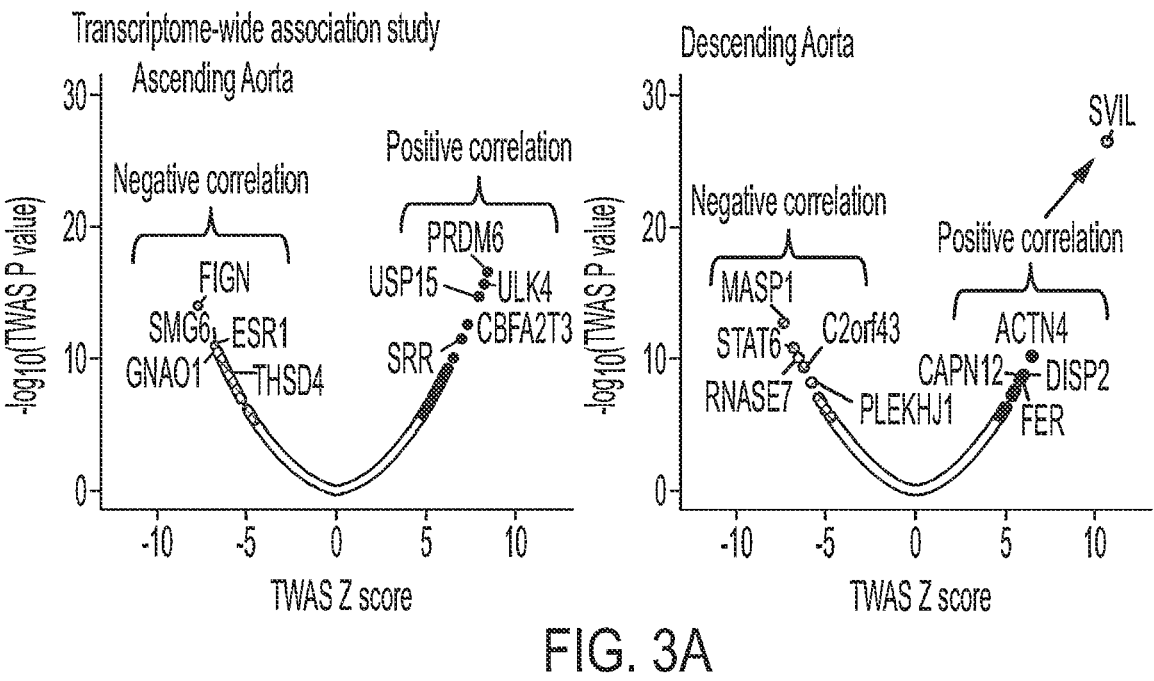
FIGS. 3A-3B illustrate gene-level association tests.

Among the strongest TWAS associations in the ascending aorta were ULK4, a gene previously linked with aortic dissection, and THSD4, whose protein product binds to fibrillin (FBN1) and modulates microfibril assembly[39]. Also notable was USP15, whose protein product is a deubiquitinating enzyme that acts on the TGF-β receptor and enhances TGF-β signaling[40,41]; the TWAS results suggest that higher USP15 expression is linked with a greater ascending aortic diameter. In the descending aorta, the strongest TWAS association was with the gene SVIL, in which increased transcription was associated with increased aortic diameter (FIG. 3A).

Rare Variant Association Test

Figure 3B:
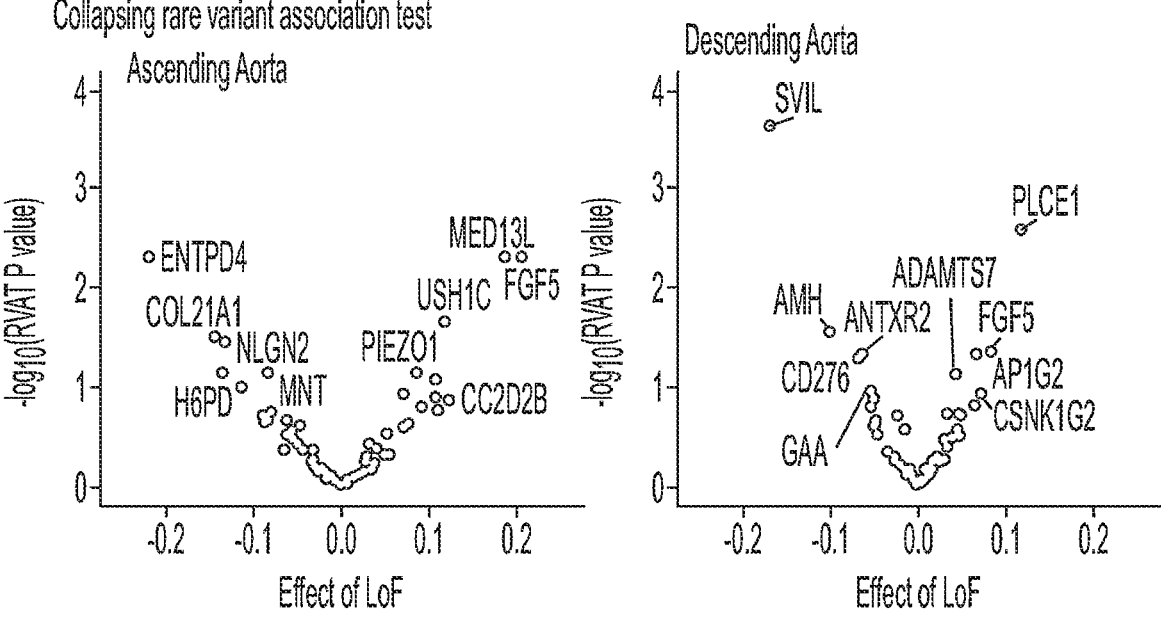

Second, a rare variant association test was conducted in 12,336 UK Biobank participants with both aortic imaging and exome sequencing data. No gene achieved Bonferroni significance in an exome-wide analysis. Restricting the analysis to genes within a 500 kb window around GWAS loci (67 genes for ascending aorta and 55 genes for descending aorta), it was found that loss of function variants in SVIL were most strongly associated with a decrease in descending aortic diameter (14 carriers; loss-of-function effect size −0.17 cm, 95% CI −0.08 to −0.26 cm, P=2.2·10⁻⁴; FIG. 3B).

Single Nucleus RNA Sequencing

Third, direct analysis of tissue and cell-specific expression patterns was performed to localize and identify relevant cell types. Tissue-specific LD score regression was used to test for enrichment of the aortic diameter GWAS results in 53 GTEx v6 tissue types[38,42]. For the ascending aortic loci, enrichment was significant in aortic and coronary artery tissues (P=8.8·10⁻⁵ and P=1.1·10⁻⁴, respectively). Enrichment of aortic and coronary artery tissues was also observed for the descending aortic loci (P=3.1·10⁻⁴ and P=1.8·10⁻³). These data are consistent with the expectation that the aorta itself is the most relevant tissue linked with the findings.

Figure 4A:
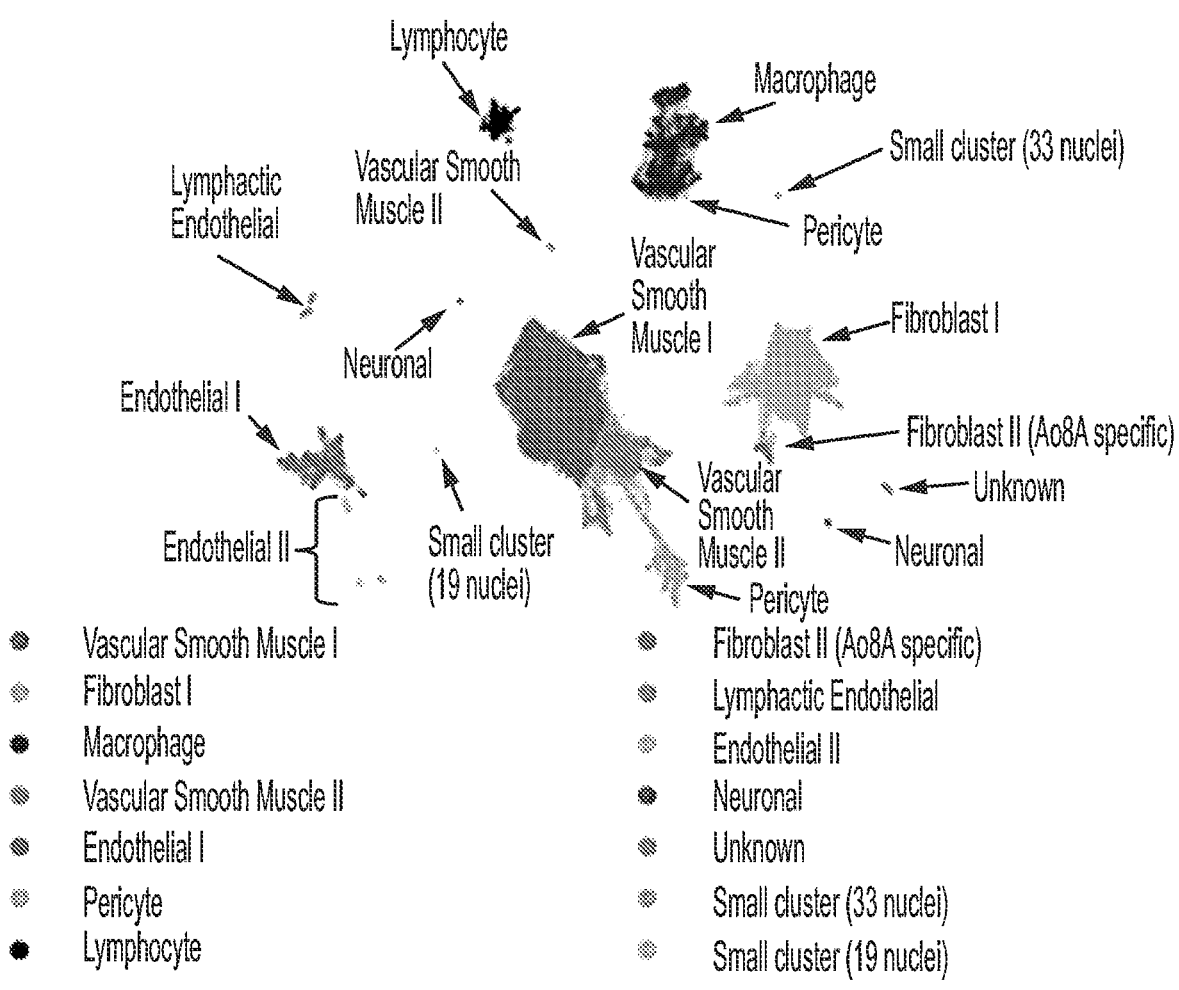
FIGS. 4A-4D illustrate single nucleus RNA sequencing analyses in human aorta. Single nucleus RNA sequencing was performed on paired ascending and descending thoracic aortic tissue from 3 humans.
Figure 4B:
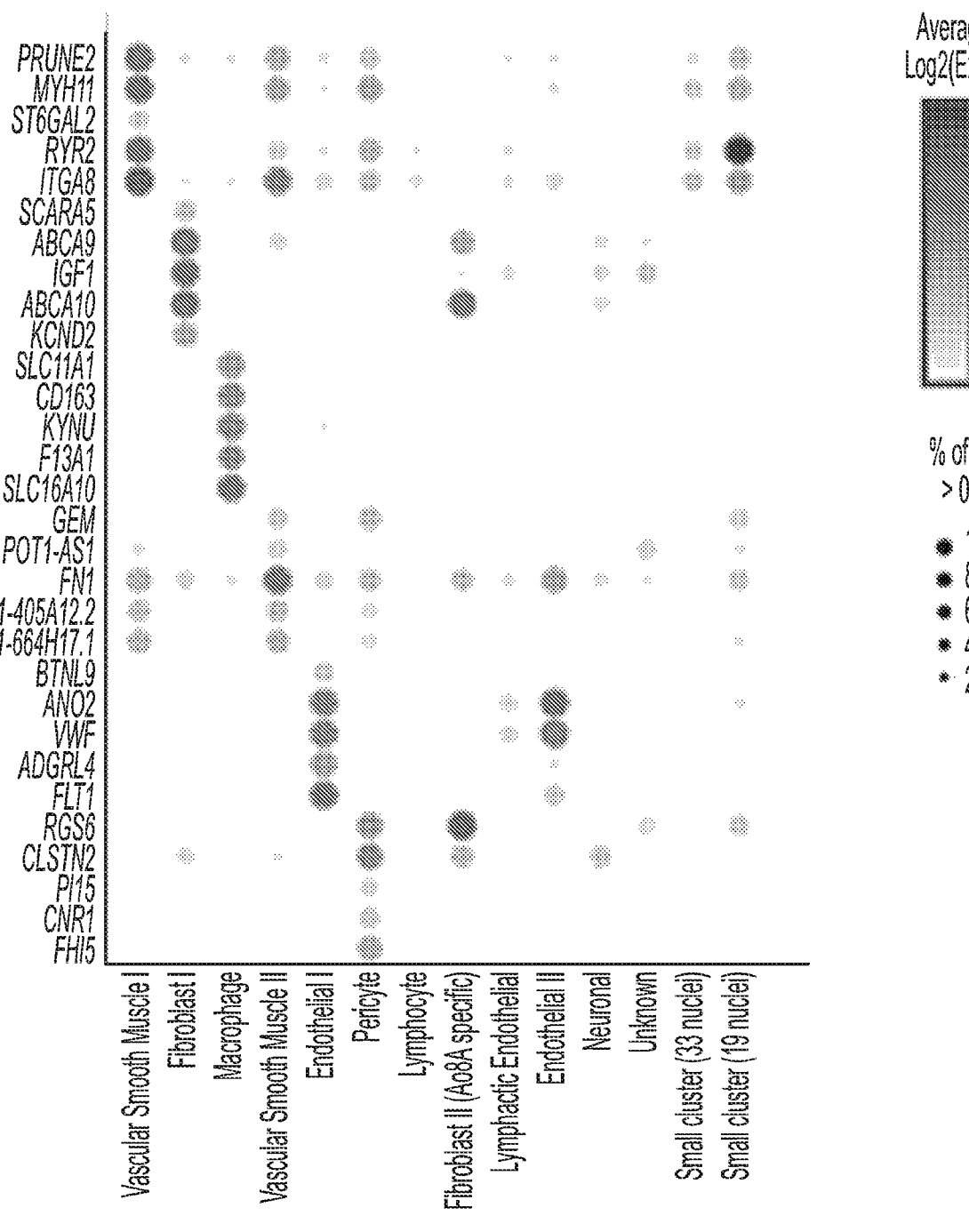
Figure 4B:
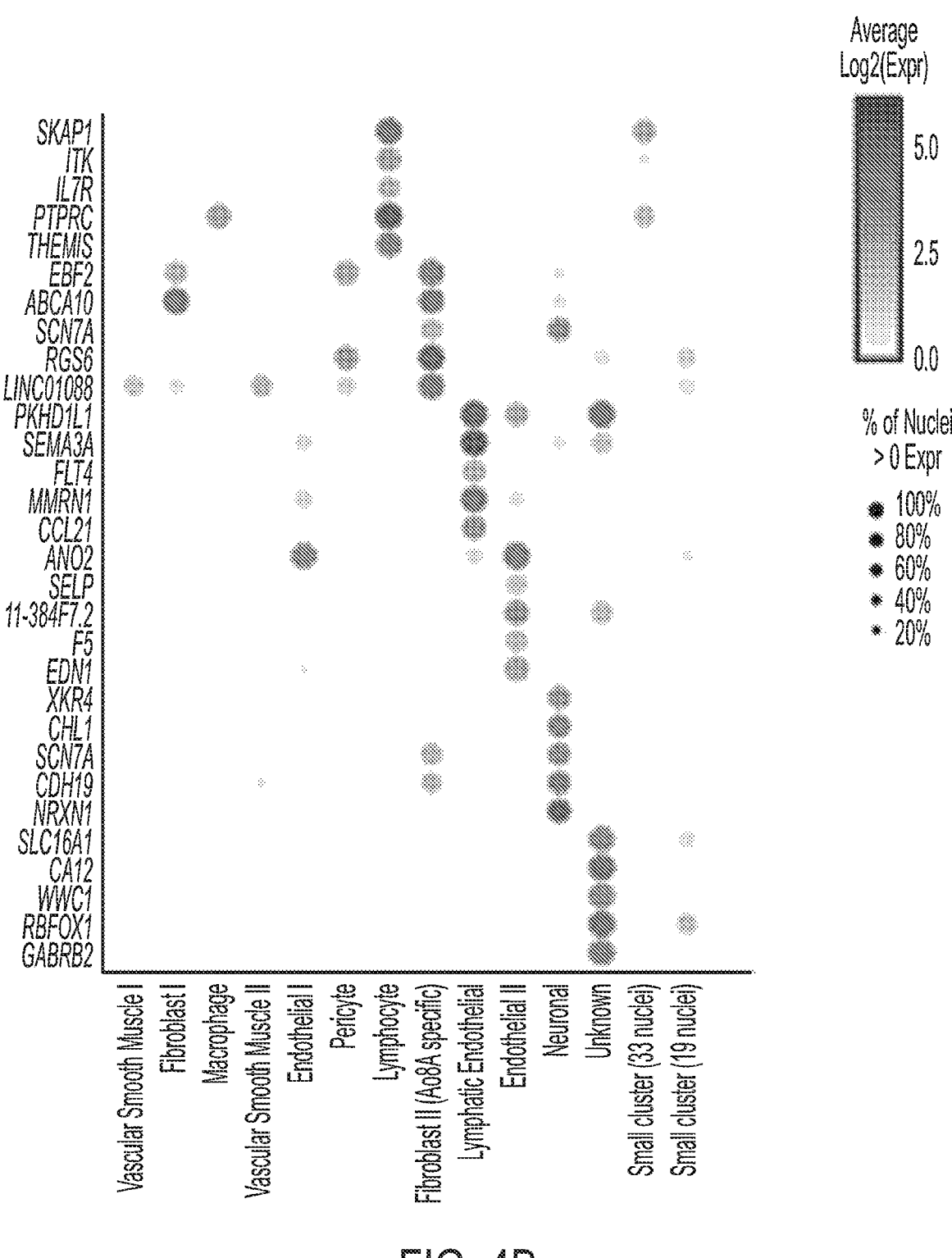
Figure 4C:
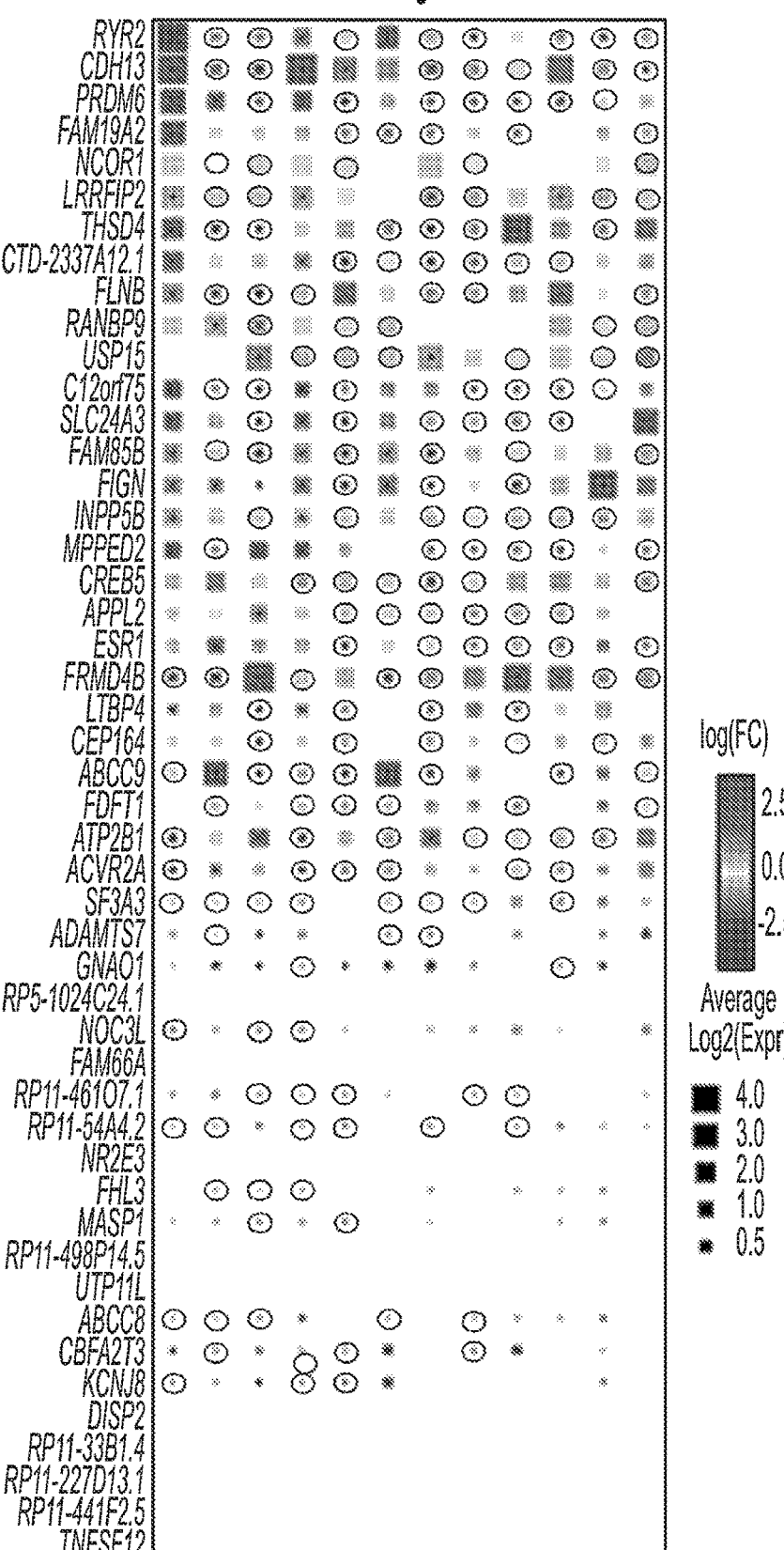
Figure 4D:
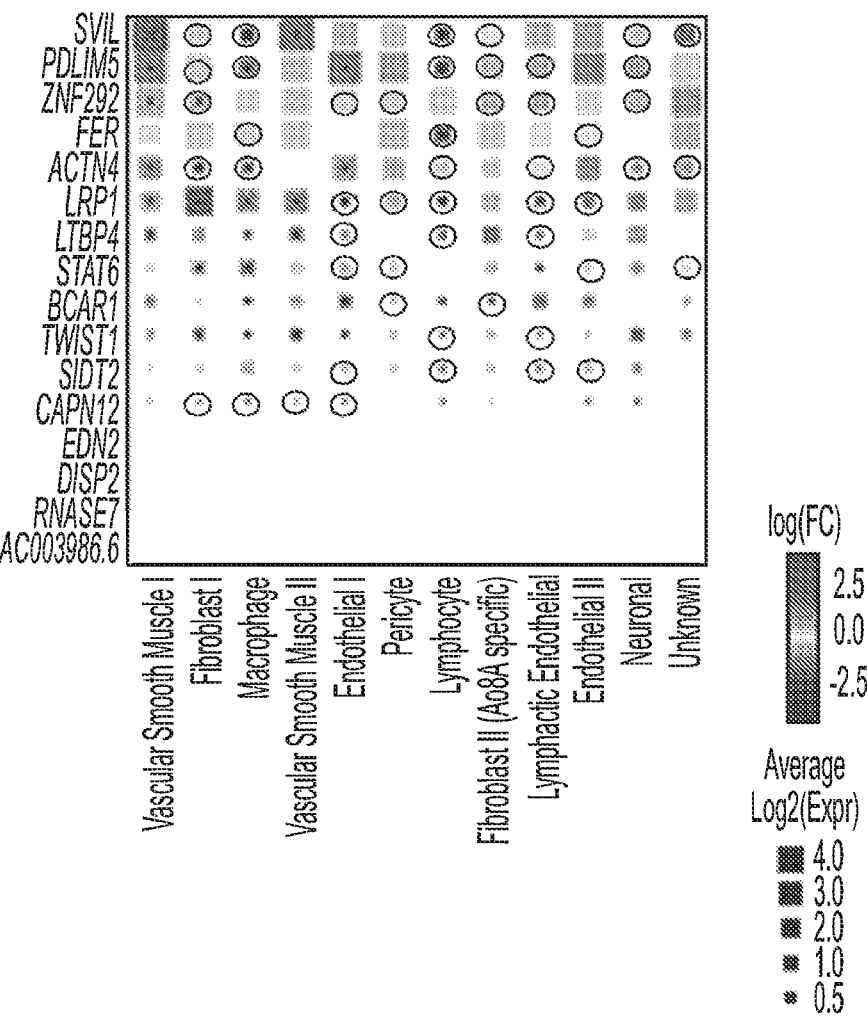

Therefore, an analysis of single-nucleus RNA sequencing (snRNA-seq) from 3 human aortas was incorporated to identify potentially relevant cell types for the genes at aortic GWAS loci. The transcriptomes of 126,239 single nuclei (of which 54,092 passed quality control) were sequenced and 14 primary cell clusters were identified (FIG. 4A). Through comparison of unique transcriptional profiles in each cluster to canonical cell markers, populations were identified comprising vascular smooth muscle cells, fibroblasts, three distinct types of endothelial cells, as well as macrophages and lymphocytes (FIG. 4B). The cell type-specific expression of the genes prioritized by the TWAS were then examined (FIGS. 4C and 4D).

Locus Prioritization

The gene SVIL was notable for being in proximity to one of the strongest GWAS signals for the descending aorta. In the TWAS, a predicted increase in SVIL expression corresponded to a larger descending aortic diameter (FIG. 3A), while loss of function variants in SVIL were associated with a smaller descending aortic diameter in the rare variant analysis (FIG. 3B). snRNA-seq revealed that SVIL is most strongly expressed in vascular smooth muscle cells within the aorta (FIGS. 4C and 4D), consistent with a role in aortic size determination.

In the ascending aorta, a lead SNP (rs1441358) was found within an intron of THSD4, which encodes ADAMTSL6, a protein that promotes the organized assembly of fibrillin-1 microfibrils[39]. In the TWAS, a decrease in predicted THSD4 expression was linked to an increase in aortic diameter. The gene was excluded from the RVAT because too few UK Biobank participants carried a loss-of-function variant. However, a recent familial study of thoracic aortic aneurysm or dissection linked loss-of-function variants in THSD4 to ascending aortic aneurysm[45], consistent with the expected direction of effect. The snRNA-seq data suggest that THSD4 is primarily expressed in aortic vascular smooth muscle cells (and a separate cell cluster with lymphatic character) consistent with a role in aortic size (FIG. 4C).

The genetic and single-nucleus transcriptomic analyses also highlight WWP2, which is linked to the size of both ascending and descending aorta. The lead SNP (rs62053262) is an expression quantitative trait locus (eQTL) in the aorta for WWP2[38]; the rs62053262 G allele corresponds to reduced expression of WWP2 in aorta and smaller aortic size. WWP2 acts as an E3 ubiquitin ligase for PTEN[46] and has previously been shown to regulate cardiac fibrosis through modulation of SMAD signaling[47]. Examining single-nucleus expression data, it is shown that WWP2 expression is enriched in aortic vascular smooth muscle cells (FIG. 15).

In other cardiovascular phenotypes, GWAS loci have been enriched for Mendelian genes[48,49], so it was asked whether the loci identified in the study were in closer proximity to more genes implicated in Mendelian aortopathies than expected by chance. An enrichment of previously described Mendelian thoracic aortic aneurysm and dissection genes[50] was not found (23 genes; 2 overlapping with ascending loci, P=0.14; 1 overlapping with descending loci, P=0.32 by one-tailed permutation tests). However, the analysis has independently identified loci containing relevant genes such as FBN1, well described as the causal gene in Marfan syndrome[51], and loci near genes such as P115, known to cause arterial dysfunction in rats[52], as well as the ABCC9/KCNJ8 locus, linked to Cantu syndrome—a rare recessive cause of aortic aneurysm in humans[53]. Other loci suggest the involvement of novel genes within networks previously implicated in aortic disease; for instance, the protein product of ASB2 is part of the E3 ligase that targets both filamin B (encoded by FLNB, the nearest gene to a lead SNP on chromosome 3) and the known aortic disease protein filamin A (FLNA) for degradation[54]. Moreover, TGF-β signaling, heavily implicated in clinical aortic disease, is also represented in the GWAS gene set as indicated by MAGMA analysis (FIGS. 16A-16B)[55].

Polygenic Score Associated with Clinical Aortic Disease

Finally, the clinical relevance of the GWAS loci was probed by asking whether a polygenic score for ascending aortic size produced from these loci was associated with thoracic aortic disease risk. The remaining UK Biobank participants who had not undergone MRI and who did not have a diagnosis of aortic disease at enrollment were analyzed. A polygenic score was built from the 89 autosomal, independently significant SNPs from the ascending aorta GWAS (including the lead SNPs as well as other SNPs with $P<5\cdot10^{-8}$ having $r^2<0.001$ with other significant SNPs within the derivation sample). This polygenic score was strongly associated with the 685 incident cases of thoracic aortic aneurysm or dissection (HR=1.43 per standard deviation; CI 1.32-1.54; $P=3.3\cdot10^{-20}$). Participants in the top 10% of the polygenic score had a 2.1-fold hazard ratio compared to the remaining 90% of the cohort (CI 1.8-2.6; $P=7.3\cdot10^{-15}$; FIG. 5). A descending aortic diameter polygenic score produced from the 46 autosomal lead SNPs had an attenuated association with thoracic aortic aneurysm or dissection (HR=1.15 per standard deviation; CI 1.07-1.24; $P=2.9\cdot10^{-4}$).

The study population largely consisted of European-ancestry UK Biobank participants. The aortic measurements were derived from a deep learning model that was trained on cardiologist-annotated segmentation data, but the vast majority of images were not manually reviewed; nevertheless, genetic results derived from manually annotated FHS imaging data were generally concordant with the findings. The experiments suggest that increasing the number of training examples would modestly improve the deep learning model, which may enhance the ability to discover genetic associations.

Discussion

In summary, deep learning was used to assess the size of the ascending and descending thoracic aorta using magnetic resonance imaging data in a large population-based biobank. 75 novel loci were identified in the ascending aorta and 43 in the descending aorta. The relationships of these loci to other traits was explored, and their association with aortic aneurysm or dissection was assessed. These findings permit several conclusions. First, these results demonstrate that deep learning is a powerful tool for deriving quantitative phenotypes from raw signal data at a population level. In particular, by using transfer learning from a deep learning model trained on a large but unrelated set of images compiled for a different task, a useful model was developed, while manually annotating only a small number of images. Second, these results highlight the value of studying quantitative traits, such as aortic size, in order to gain greater understanding of disease processes underlying aneurysm and dissection. Third, the modest genetic correlation and limited locus overlap of the ascending and descending thoracic aorta highlight their distinct biology. Fourth, several potential gene targets were prioritized based on integration of GWAS, TWAS, and rare variant analyses, and their likely cell type of relevance was identified with snRNA-seq. Fifth, a polygenic score for ascending aortic size is an independent risk factor for aneurysmal enlargement of aorta. In the future, it will be interesting to determine if a model incorporating a polygenic score and clinical risk factors might identify high-risk, asymptomatic individuals who would benefit from thoracic imaging to screen for ascending aortic aneurysm.

Methods

Study Design

The UK Biobank is a richly phenotyped, prospective, population-based cohort that recruited 500,000 individuals aged 40-69 in the UK via mailer from 2006-2010[56]. In total, 487,283 participants with genetic data were analyzed, who had not withdrawn consent as of October 2018. Analysis was approved by the Partners HealthCare institutional review board. GWAS replication was performed in an imaging substudy of the community-based Framingham Heart Study (FHS) Offspring and Third-Generation cohorts; participants were ascertained based on sex-specific age cutoffs (>35 years for men and >40 years for women), and weight (<350 pounds as described previously and approved by the institutional review boards of the Boston University Medical Center and the Massachusetts General Hospital[30]. Ascending and descending human aortas were obtained from 5 human patients through a rapid autopsy protocol within 4 hours of cardiac death.

The design was as follows: pixels belonging to the aortic blood pool were manually annotated in cardiac MRI from the UK Biobank. A deep learning model was then developed, trained on the manual annotations, to perform the same task at scale. The model was then applied to the remainder of the imaging data from the UK Biobank, permitted estimation of the aortic diameter for every participant with imaging. Genetic discovery of loci related to the diameter of the ascending and descending thoracic aorta, treated as quantitative traits, was performed in this same UK Biobank cohort. A replication GWAS, based on previously performed aortic diameter measurements using computed tomography, was performed in FHS. With the genetic results from the UK Biobank, a transcriptome-wide association study (TWAS) was performed by incorporating publicly available gene expression data in order to prioritize genes at each genomic locus. A rare-variant association test was also performed in just over −12,000 UK Biobank participants with both imaging and exome sequencing data. A single nucleus RNA sequencing study was then performed (using nuclei from aortas obtained from 5 human patients through a rapid autopsy protocol) to identify the aortic cell types that were most relevant to the genes highlighted by the bioinformatic analyses. A polygenic score produced from SNPs associated with aortic diameter in the UK Biobank GWAS was used to predict incident aortic disease in the remaining UK Biobank participants who had not undergone cardiac imaging.

Statistical analyses were conducted with R version 3.6 (R Foundation for Statistical Computing, Vienna, Austria).

Cardiac Magnetic Resonance Imaging

The UK Biobank is conducting an imaging substudy on 100,000 participants[57,58]. Cardiac magnetic resonance imaging was performed with 1.5 Tesla scanners (MAGNETOM Aera, Siemens Healthcare), using electrocardiographic gating for cardiac synchronization[58]. A balanced steady-state free precession cine, consisting of a series of exactly 100 images throughout the cardiac cycle, was acquired for each participant at the level of the right pulmonary artery[58].

Deep Learning for Segmentation of the Aorta

Segmentation maps were traced for the ascending and descending thoracic aorta manually by a cardiologist. To produce the final model used in this study, 116 samples were chosen, manually segmented, and were then used to train a deep learning model with FASTAI™ v1.0.59[13]. The model consisted of a U-Net-derived architecture, where the encoder was a resnet34 model pre-trained on ImageNet[13-15,59,60]. 80% of the samples were used to train the model, and 20% were used for validation. Development versions prior to this final model are detailed in the following section. Variations on this modeling approach, and inter-rater evaluations, are described in subsequent sections.

During training, all images were resized to be 160 pixels in width by 132 pixels in height for the first half of training ('small image training'), and then 240 pixels in width by 196 pixels in height, which is the native size of these images, for the second half ('large image training'), detailed below. The Adam optimizer was used, and the model was trained with a minibatch size of 4 (when training with small images) or 2 (when training with large images)[61]. Rather than using extensive hyperparameter tuning with a grid search, the model was instead trained using a cyclic learning rate training policy, which alternately decreases and increases the learning rate during training[62].

The maximum learning rate (the step size during gradient descent) was chosen with the learning rate finder from the FASTAI™ library[13]. During small image training, the maximum learning rate was set at 0.002, with 20% of the iterations permitted to have an increasing learning rate during each epoch across 20 epochs. This was performed while keeping all ImageNet-pretrained layers fixed, so that only the final layer was fine-tuned. Then all layers were unfrozen, and the model was trained for an additional 15 epochs with the same maximum learning rate. For large image training, the same model was then updated using full-dimension images, and the maximum learning rate was set to 0.0002, with 30% of the iterations permitted to have an increasing learning rate over 8 epochs. Then, all layers were unfrozen, and the model was trained for an additional 15 epochs with a maximum learning rate of 0.0002. Additional details about hyperparameter selection are provided in the subsequent sections.

Throughout training, augmentations (random perturbations of the images) were applied as a regularization technique. These augmentations included affine rotation, zooming, and modification of the brightness and contrast. Because medical imaging data is not symmetric across the midline of the human body, mirroring transformations was not permitted. Using the software default settings for splitting samples into training and validation sets, 92 images were used to train the model, and 24 were held out for validation. Segmentation accuracy was assessed separately for the ascending and descending aorta.

This model was then used to infer segmentation of the ascending and descending aorta on all available "CINE_segmented_Ao_dist" images in the UK Biobank. During inference, adaptive pooling was used to permit arbitrary image sizes[63], which allows for the production of output that matches the input size, preserving the number of millimeters per pixel as reported in the metadata.

Development Versions of the Training Data

The 116 annotations performed were initially annotated with a 3 pixel radius brush. Consequently, some of the aortic blood pool was frequently annotated as part of the aortic wall (FIG. 6, left and center panels). These annotations were revised using a 1 pixel brush, yielding training data with a more precise blood pool-wall boundary (FIG. 6, right panel). All training data described in this study, including data produced by other raters, were annotated with 1 pixel resolution. All models described in this study were trained on this 1 pixel resolution training data.

Development Versions of the Deep Learning Model

The first batch of manual segmentation mapping of aorta was performed by one cardiologist on 58 randomly chosen images from the UK Biobank, a sample size that was chosen to balance the time required for annotation (approximately 5 minutes per sample) against the need for diverse data to train the ImageNet-based segmentation model. When the output of this model was visualized, the notable recurring error was the miscategorization of breast prostheses as aorta. To produce the training set used to build the model described in this manuscript, the sample size was doubled from 58 images to 116, of which 15 contained breast prostheses.

The approach to choosing the model hyperparameters began with the default settings from the FastAI "Deep Learning Part 1" 2019 coursework (Lesson #3)[64]. The learning rate was chosen with the learning rate finder, as recommended by the FastAI library authors. The default notebook uses 10 training epochs with an increasing learning rate in 80-90% of iterations through each epoch. With the data, it was observed that the model trained with those parameters significantly underfit, which means that the validation loss was continuing to decrease at the end of the 10 epochs. So, the number of epochs was increased during small image training and the percentage of iterations with an increasing learning rate were decreased until the validation loss no longer continued decreasing, which required about 20 epochs while permitting the learning rate to increase in only 20% of epochs. In contrast, it was found that at the large image training step, fewer epochs were required to achieve a low validation loss, using only 8 while retraining the last layer.

Training Set Size

To assess whether additional training examples would have a significant impact on segmentation accuracy or the genetic findings, one rater annotated a total of 500 images. The same modeling procedure described above was performed using 30, 60, 116, 250, or 500 images for training. 5-fold cross-validation was used and the mean accuracy was reported, plotted in FIG. 17.

Inter-Rater Reliability

Two individuals independently performed manual annotation of the ascending and descending aortic blood pool in the same 116 images. Cohen's kappa (an estimate of observed agreement that accounts for agreement that is expected by chance, and which ranges from 0-1) was used to assess agreement between the two raters on a per-pixel basis[65]. Pixels were said to agree when they were annotated as part of the same blood pool (of either ascending or descending aorta) or as background. They were said to disagree when one rater identified a pixel as background when the other identified the pixel as blood pool, or vice versa. This was performed for all 116 images, and the kappa statistic for ascending and descending aorta were averaged across all images.

The two raters' 116 manually annotated images were then separately used to train their own deep learning models (using the same hyperparameters as described above). These models were both applied to all images available in the UK Biobank, and Cohen's kappa was then assessed on all images and averaged.

Segmentation Quality Control

All subsequent analyses in the UK Biobank were performed with the output from the deep learning model trained on 116 images annotated by one annotator.

Single-image quality control was performed first: images which lacked any pixels labeled as aorta were flagged. Next, adjacent pixels were grouped into connected components using the Rosenfeld-Pfaltz algorithm[16]. Images having several ascending or descending aortic components more than 5 standard deviations above the mean were flagged.

Then, a quality control step was performed that took advantage of the dynamics of the cardiac cycle. The largest frame-to-frame change in the cross-sectional area of the ascending and descending aorta was computed. Outliers beyond 5 standard deviations above the mean were flagged.

Any participant with at least one image that was flagged with this quality control procedure was excluded from further analysis. This quality control procedure was iterative: the above steps were performed repeatedly until no further samples were removed. Exclusion due to failing quality control was performed separately for both traits: 9 iterations were required before no additional samples were excluded for the ascending aorta, while 5 iterations were required for the descending aorta. Participants whose images were excluded from the ascending aortic analysis due to failing quality control were still eligible to be included in the descending aortic analysis and vice versa.

Extraction of Aortic Diameter from Deep Learning Output

Having identified which pixels represented aorta, the aorta's cross-sectional dimensions were determined. The aorta was treated as an ellipse: major and minor axes were computed using classical image moment algorithms[66]. Separately for the ascending and the descending thoracic aorta, the length of the minor elliptical axis (in centimeters) was ascertained at the point in the cardiac cycle when the aorta was at its maximum size (closely corresponding with end-systole). The minor axis was chosen for analysis because imperfection in the orientation of the plane of image acquisition may falsely elongate the apparent major axis of the ascending and descending aorta; in contrast, the dimension of the minor axis is not affected by such perturbations. The length of the minor axis, in pixels, was converted to an absolute length in centimeters by using the metadata accompanying each image; in the UK Biobank, the reported pixel width and height is 1.58 millimeters for nearly all "CINE_segmented_Ao_dist" images. The length of the minor axis (i.e., the diameter) of the ascending and descending aorta were treated as the primary phenotypes for subsequent analyses.

Characteristics of the Thoracic Aortic Diameter

The correlation between ascending and descending aortic diameter was assessed with ordinary least squares regression. Because of the strong dependence of aortic diameter on sex, the model was configured to treat sex as a fixed effect and predicted the ascending aortic diameter from that of the descending aorta. To remove the contribution of sex from the estimate of model fit ($r^2$), ascending aorta diameter from sex alone was also predicted, and then an F test was performed to compare the two nested models.

It was also assessed whether the dispersion of the diameters of ascending and descending aorta differed. This analysis was stratified by sex. First, it was asked whether the variance was equal between ascending and descending diameter using the F-test in R (implemented as var.test). Because the means of the two diameters were also different, it was then tested whether the coefficient of variation, a dimensionless value computed by dividing the standard deviation by the mean, was equivalent between ascending and descending aorta. Significance testing to compare the coefficients of variation was performed using the function asymptotic_test from the cvequality package[67].

Repeat Measurements

Nearly 3,000 UK Biobank participants have undergone imaging at two separate visits. For these participants, only data from their initial imaging visit was used for all analyses in this study, aside from the analysis in this section.

In these participants, linear regression was used to compare the estimated ascending and descending aortic diameters derived from the deep learning model in the second imaging visit to the estimates from the first imaging visit. For instance, linear regression of the estimated ascending (descending) aorta diameters derived from the deep learning model from the first visit and the estimated ascending (descending) aorta diameters derived from the deep learning model from the second visit in both male and female subjects is shown in FIG. 19.

Aortic Disease Codes

International Classification of Diseases version 10 (ICD-10) codes and Office of Population Censuses and Surveys Classification of Interventions and Procedures version 4 (OPCS-4) codes used to define aortic procedures and thoracic aortic aneurysm, dissection, or rupture were used for GWAS participant exclusion and polygenic score assessment.

Correlation Between Phenotypes and Aortic Measurements

Phenome-wide association studies (PheWAS) were conducted to assess the relationship between the observed aortic traits and (a) other continuous traits measured in the UK Biobank, and (b) other disease phenotypes based on ICD-10 and OPCS-4 codes.

All participants with aortic measurements were used in the continuous trait PheWAS. The number of participants modeled for each trait varied based on availability in the UK Biobank. 669 traits had sufficient data for analysis using a linear model accounting for the MRI serial number, sex, PC1-5, age at enrollment, the cubic natural spline of age at the time of MRI, and the genotyping array.

The same covariates were used in a logistic regression model testing the relationship between the aortic traits and 1,333 PheCode-defined diseases derived from hospital billing codes.

Genotyping, Imputation, and Genetic Quality Control

As detailed previously, UK Biobank samples were genotyped on either the UK BiLEVE or UK Biobank Axiom arrays, then centrally imputed into the Haplotype Reference Consortium panel and the UK10K+1000 Genomes panel[68]. Variant positions were identified using the GRCh37 human genome reference. Genotyped variants with genotyping call rate <0.95 and imputed variants with INFO score <0.3 or minor allele frequency <=0.001 in the analyzed samples were excluded. After variant-level quality control, 16,080, 416 imputed autosomal variants and 566,283 imputed variants on the X chromosome remained for analysis.

Participants without imputed genetic data, or with a genotyping call rate <0.98, mismatch between self-reported sex and sex chromosome count, sex chromosome aneuploidy, excessive third-degree relatives, or outliers for heterozygosity as defined centrally by the UK Biobank were excluded[68].

Participants with a measured aortic diameter greater than 5 cm, a history of aortic aneurysm or dissection, or a history of aortic surgical procedures were excluded. It was assessed whether individuals with rare variants likely to lead to Mendelian aortopathy from the GWAS could also be excluded; however, in the subset of ~12,000 participants in the imaging substudy who had exome sequencing data, none had Marfan-related FBN1 variants identified in ClinVar.

The aortic diameters were found to be non-normally distributed (with non-zero skewness and kurtosis). Therefore, for the heritability analysis and genome-wide association study, they were first inverse-normal transformed[69].

Heritability and Genetic Correlation of Aortic Traits

BOLT-REML v2.3.4 was used to assess the SNP heritability of the minor axis length of the ascending and descending thoracic aorta and their genetic correlation with one another using the directly genotyped variants in the UK Biobank[32].

Genome-Wide Association Study of Aortic Traits

The inverse-normal transformed values of the diameter of the ascending and descending thoracic aorta were analyzed at the frame within the cardiac cycle when they were at their largest. These traits were adjusted for age at enrollment, age and age[2] at the time of MRI, age at enrollment, the first 10 principal components of ancestry, sex, the genotyping array, and the MRI scanner's unique identifier.

Genome-wide association studies for the diameter of the ascending and descending thoracic aorta were conducted using BOLT-LMM version 2.3.4 to account for cryptic population structure and sample relatedness[32,33]. The full autosomal panel of 714,512 directly genotyped SNPs that passed quality control were used to construct the genetic relationship matrix (GRM). GWAS covariates included age at enrollment, age and age$^2$ at the time of MRI, the first five principal components of ancestry, sex, the genotyping array, and the MRI scanner's unique identifier. Associations on the X chromosome were also analyzed, using all autosomal SNPs and X chromosomal SNPs to construct the GRM (N=732,151 SNPs), with the same covariate adjustments and significance threshold as in the autosomal analysis. In this analysis mode, BOLT treats individuals with one X chromosome as having an allelic dosage of 0/2 and those with two X chromosomes as having an allelic dosage of 0/1/2. Variants with association $P < 5 \cdot 10^{-8}$, a commonly used threshold, were considered to be genome-wide significant.

In order to identify independently significantly associated variants, linkage disequilibrium (LD) clumping was performed with plink-1.9[70] in the same participants used to conduct the GWAS. A wide 5-megabase window (--clump-kb 5000) and a stringent LD threshold (--r2 0.001) were used in order to identify independently significant SNPs despite long LD blocks (particularly on chromosome 16 near WWP2). Using the independently significant SNPs, distinct genomic loci were defined by starting with the SNP with the strongest P value, excluding other SNPs within 500 kb, and iterating until no SNPs remained. The independently significant SNPs that defined each genomic locus are termed the lead SNPs. Lead SNPs were tested for deviation from Hardy-Weinberg equilibrium at a threshold of $P < 1 \cdot 10^{-670}$.

Assessment for Test Statistic Inflation

Quantile-quantile plots of SNP association test statistics were produced. Linkage disequilibrium (LD) score regression analysis was performed with ldsc version 1.0.0[24]. For both the ascending and descending aorta GWAS, the genomic control factor (lambda GC) was partitioned into polygenic and inflation components using the ldsc software's defaults.

European Sensitivity Analysis

As a sensitivity analysis, the ascending and descending aortic diameter GWAS were repeated while excluding participants that were not centrally labeled by the UK Biobank as "white British." This is a label that was applied to people who self-identified as British and who were, in addition, "genetic inliers" based on the first three pairs of genetic principal components (PC1&2, PC3&4, PC5&6) by using the aberrant package as described previously[68,71.]

GWAS Replication

For external replication of the UK Biobank GWAS results, a GWAS of ascending and descending aortic diameter in FHS was conducted, measured on computed tomography (CT) images.

The genetic profiles of FHS participants were measured by the Affymetrix GeneChip 500k Array Set & 50K Human Gene Focused Panel, and genotyping was called using BRLMM as previously described[72,73]. Variants with call rate <0.97, HWE $P < 10^{-6}$, N>100 Mendelian errors, or MAF <0.01 were excluded. The remaining variants were then imputed to the TOPMed imputation panel using Michigan Imputation Server (imputationserver.sph.umich.edu/index.html)[74].

A multi-detector computed tomography (CT) scanner (General Electric Lightspeed+8 detector scanner) was used to assess the aorta in FHS participants[3"1]. All measurements have been deposited into dbGaP (Accession: phs000007.v30.p11). The association between each genetic variant and CT traits was tested with linear mixed effects models using the kinship package in R, and adjusted for sex, age, age square, cohort (original cohort, offspring cohort, or third generation cohort), and first five principal components of ancestry.

Lead SNPs were then identified from the main UK Biobank GWAS which were also available in the FHS GWAS and ensured that their effect alleles were matched. A two-tailed binomial test was then performed for directional consistency of effect direction (i.e., the expected effect of SNP dosage on aortic diameter). The null hypothesis was that for each of these independent SNPs, directional agreement would be expected by chance 50% of the time. Additionally, linear regression was performed, predicting the FHS Z scores with the UK Biobank Z scores. To assess whether more extreme Z scores corresponded with better agreement between the primary study and the replication study, the SNPs allowed to participate in the linear model were iteratively restricted by adjusting the UK Biobank SNP P value inclusion threshold from $P < 5 \cdot 10^{-6}$ to $P < 5 \cdot 10^{-14}$, assessing the coefficient of determination of the model at several incremental thresholds within that range. This analysis was performed for both ascending and descending aortic SNPs.

Genetic Correlation with Other Quantitative Traits

Genetic correlation across traits was assessed using ldsc[35] in 281 continuous traits from the UK Biobank whose ldsc-formatted summary statistics were made available by the Neale Lab[34]. Of the 281 tested traits, genetic correlation with 257 traits was computable in the ascending aorta and with 256 traits in the descending aorta.

Tissue-Specific LD Score Regression

To address which tissues were most tightly linked to the ascending and descending aorta GWAS results, tissue-specific LD score regression was applied against 53 GTEx v6 tissue types that were preprocessed by the ldsc authors[38,42]. The ldsc authors identified genes that were specifically expressed in each tissue, retaining the top 10% of genes most specifically expressed from each of the 53 tissues. Stratified LD score regression was then conducted with these specifically enriched gene sets (ldsc-SEG) to determine the contribution of the tissue-specific expression to the heritability of the size of the aorta. The returned P value represents the probability of seeing such a large coefficient if the null hypothesis (that the tissue is not enriched) were true; i.e., it tests whether the tissue-specific contribution is distinguishable from zero. Significance was determined using a false discovery rate (FDR) of 5%.

Mendelian Aortopathy Gene Set Enrichment

The 23 thoracic aortic aneurysm and dissection-related genes from Category A, B, or C from Renard, et al, were considered to be Mendelian aortopathy genes[50]. SNPsnap was used to generate 10,000 sets of SNPs that match the lead SNPs from the GWAS based on minor allele frequency, number of SNPs in linkage disequilibrium, distance to the nearest gene, and gene density at the locus[75]. A lead SNP was considered to be near a Mendelian locus if it was within 500 kilobases upstream or downstream of any gene on the panel. Significance was assessed by permutation testing across the 10,000 SNP sets to determine the neutral expectation for the number of overlapping genes in loci with characteristics similar to those discussed above, yielding a one-tailed permutation P value.

Transcriptome-Wide Association Study

For ascending and descending thoracic aorta separately, a TWAS was performed to identify genes whose imputed cis-regulated gene expression correlates with aortic size[37,76-78]. FUSION was used with eQTL data from GTEx v7. Precomputed transcript expression reference weights for the aorta (N=6,462 genes) were obtained from the FUSION authors' website (gusevlab.org/projects/fusion/)[37,38]. FUSION was then run with its default settings.

MAGMA Gene Set Analysis

Using MAGMA 1.07b, 7,706 gene sets from MSigDB were tested for enrichment in the ascending and descending aortic GWAS results[55,79]. Gene locations for GRCh37 and European reference data were used that were preprocessed by MAGMA's authors (ctg.cncr.nl/software/magma). The composite "GO_PANTHER_INGENUITY_KEGG_REAC-TOME_BIOCARTA" gene sets from MSigDB were used, provided by the MAGENTA authors[80,81].

Exome Sequencing in UK Biobank

An exome sequencing analysis was conducted in the first 50,000 exomes released by the UK Biobank. Samples from the UK Biobank were chosen for exome sequencing based on enrichment for MRI data and linked health records[82]. Exome sequencing was performed by Regeneron and reprocessed centrally by the UK Biobank following the Functional Equivalent pipeline[83]. Exomes were captured with the IDT xGen Exome Research Panel v1.0, and sequencing was performed with 75-base paired-end reads on the Illumina NovaSeq 6000 platform using S2 flowcells. Alignment to GRCh38 was performed centrally with BWA-mem. Variant calling was performed centrally with GATK 3.0[84]. Variants were hard-filtered if the inbreeding coefficient was <−0.03, or if none of the following were true: read depth was greater than or equal to 10; genotype quality was greater than or equal to 20; or allele balance was greater than or equal to 0.2. In total, 49,997 exomes were available. Variants were annotated with the Ensembl Variant Effect Predictor version 95 using the --pick-allele flag[85]. LOFTEE was used to identify high-confidence loss of function variants: stop-gain, splice-site disrupting, and frameshift variants[86].

Rare Variant Association Test

A collapsing burden test was conducted to assess the impact of loss-of-function variants in up to 12,336 participants who had aortic measurements and exome sequencing data available. For quantitative traits (minor axis length of the ascending and descending thoracic aorta), with heritability of approximately 0.6, it was estimated that 13 loss-of-function variant carriers would be sufficient to achieve a power of 0.8 at an alpha of 0.05. Variants with MAF >=0.001 were excluded. Using the LOFTEE "high-confidence" loss-of-function variants, for each of the 3,285 protein-encoding genes with at least 13 carriers of one or more loss-of-function variants in the UK Biobank, it was tested whether loss-of-function carrier status was associated with aortic minor axis length. The model was adjusted for weight (kg), height (cm), the MRI serial number, age at enrollment, the cubic natural spline of age at the time of MRI, sex, genotyping array, and PC1-5. An additional analysis was performed that subset the gene list to those within a 500 kb window of one of the independently associated SNPs from the GWAS.

Association of Aortic Polygenic Scores with Incident Disease

Within a strictly defined European subset of the UK Biobank, a polygenic score was computed from the 89 autosomal, independently significant SNPs from the ascending aorta GWAS and another from the 46 autosomal, independently significant SNPs from the descending aorta GWAS, excluding participants whose data was used for the GWAS.

The strict European ancestry was defined using individuals who self-identified in the UK Biobank as British, Irish, or of other European ancestry as previously described[87]. The R package aberrant was applied to the first three pairs of principal components with the parameter lambda set to 40; only inliers were considered "European" for this analysis[71].

The relationship between the ascending aorta polygenic score and incident thoracic aortic aneurysm or dissection was analyzed in 385,621 individuals (685 cases) using a Cox proportional hazards model that was also adjusted for clinical risk factors. There is limited data regarding clinical risk factors for thoracic aortic aneurysm outside of associated syndromes and family history, so putatively relevant covariates were chosen based in part on inference from evidence in the abdominal aortic aneurysm literature[88]. These covariates included sex, prevalent diagnoses of type 2 diabetes or hypertension, tobacco smoking history (the number of pack years of tobacco smoking), body mass (the cubic natural spline of BMI), and age (the cubic natural spline of age at enrollment). Adjustments were also made for other covariates including the cubic natural spline of height, the number of standard alcoholic drinks consumed per week, the genotyping array, and the first five principal components of ancestry. This analysis was performed separately for the ascending and descending aorta polygenic scores.

Human Single Nucleus RNA Sequencing: Aortic Nuclei Isolation and Library Generation Ascending and descending human aortas were obtained from 5 human patients through a rapid autopsy protocol within 4 hours of cardiac death. Aortic segments from the aortic root, ascending aorta, descending thoracic aorta and infrarenal abdominal aorta were surgically collected by a single operator and immediately frozen in LN2 and stored at −80° C. until use. For nuclei isolation, aortas were mounted frozen on OCT and sectioned at 65 um at −20° C. with a cryotome (Leica CM 1950). Cut tissues were incubated in ice cold nuclei isolation buffer (NIB: Hepes, Sucrose, MgCl2, KCl, Igepal-630, BSA, pH 7.2, 1:100 murine RNAse inhibitor, 1:1000 elastase) and then liberated by dounce homogenization in isolation buffer without elastase. Homogenates were centrifuged at 40 g×4', at 4° C. Supernatant was filtered through sequential 40 μm and 10 μm meshes (Pluriselect, Germany), and filtrate was centrifuged at 600 g×5', at 4° C. Supernatant was discarded and pellet resuspended and washed once (600 g×5', 4° C.) with nuclei wash buffer (NIB without detergent). Final pellet was resuspended in 150 μL nuclei storage buffer (NWB with 1:80 murine RNAse inhibitor, NEB). All procedures were performed on ice. Nuclei, stained with Trypan blue, were manually counted using a hemocytometer (inCyto.com). 7,000 nuclei (5,000 recovery) per aorta were used for droplet generation and library construction according to manufacturer's protocol (10× Genomics, V3).

Human Single Nucleus RNA Sequencing: Data Processing

BCL files for a total of 10 experiments (5 individuals each with ascending and descending aorta) were processed using cellranger mkfastq (CellRanger 3.0.2, 10× Genomics) to generate FASTQ files. These FASTQ files were trimmed using cutadapt to remove the template switch oligo adapter sequence and its reverse complement [AAGCAGTGGTAT-CAACGCAGAGTACATGGG (SEQ ID NO: 1), CCCATGTACTCTGCGTTGATACCACTGCTT (SEQ ID NO: 2)] (max_error_rate=0.07, min_overlap=10) and all four homopolymer repeats [$A_{30}$, $C_{30}$, $G_{30}$, $T_{30}$] (max_error_rate=0.1, min_overlap=20)[89]. The trimmed FASTQ files were used as input to cellranger count (CellRanger 3.0.2) using the human GRCh38 pre-mRNA gene reference in order to obtain count matrices.

Human Single Nucleus RNA Sequencing: Sample-Level Quality Control

Quality control at the level of entire samples was performed by examining QC metrics produced by cellranger count, as well as Uniform Manifold Approximation and Projection (UMAP) plots and plots of log(UMI count) versus log(droplet ID) ranked by decreasing UMI count[90]. Both ascending and descending aorta samples from 2 individuals (4 experiments) were identified as such strong outliers that they were deemed to be QC failures and subsequently removed. Therefore, the remainder of analyses were conducted with the data from the 3 individuals (6 experiments) passing quality control.

Human Single Nucleus RNA Sequencing: Noise Removal

Count matrices from the remaining 6 datasets were processed using cellbender remove-background to call cells (and eliminate empty droplets) and to remove background noise caused by ambient RNA and barcode swapping (CellBender 0.1, default settings with expected-cells=5000, total-droplets-included=30000, z-dim=100, z-layers=500, epochs=350)[91]. As an extreme number of counts are assigned to the gene MALAT1 it is excluded from all downstream analysis.

Human Single Nucleus RNA Sequencing: Nuclei QC

A series of quality control metrics were used to remove low quality nuclei. Nuclei with total unique molecular identifiers less than 500, or greater than the third quartile multiplied by the interquartile range (IQR), per experiment were removed. Nuclei with a total number of genes less than 250, or greater than the third quartile multiplied by the IQR, per experiment were removed. Strict upper bounds were set for the percent of reads mapping to mitochondrial genes (<0.5%), the proportion of reads mapping exclusively to exons (<0.20) as calculated in scR-Invex (github.com/broadinstitute/scrinvex), and a predicted doublet score (<0.25) as calculated in Scrublet with default parameters[92]. Finally, per-nucleus entropy was calculated using the ndd python library (pypi.org/project/ndd/1.6.3/) and any nucleus with entropy less than 8 or greater than 10 was removed. A total of 54,092 nuclei remained after quality control.

Human Single Nucleus RNA Sequencing: Aggregated Map

The top 2000 highly variable genes were calculated using in Seurat 3.1.5 (method=vst, n_genes=2000) followed by batch correction using these highly variable genes with scVI (latent_dimension=50, max_epochs=300, early_stopping=True)[93,94]. A neighborhood graph was constructed in scanpy using the latent embeddings of each nucleus from scVI with n_neighbors=15 and Euclidean distance[95]. A two dimensional visualization of the data was created with UMAP (min_dist=0.1) on this neighborhood graph. Nuclei in the aggregated map were clustered using the Leiden algorithm at resolution 0.4.

Human Single Nucleus RNA Sequencing: Differential Expression Between Cell Types

Differential expression testing was performed for each gene by comparing expression in each cluster to all other clusters in R limma[96]. Testing was carried out as per the recommendation by Lun and Marioni[97], after (1) summing count data per sample per cluster, (2) normalizing using DESeq2[98], and (3) correcting for the mean-variance trend using voom. Contrasts of one cell cluster versus all others were fit using the model (~0+cluster+experiment) to extract an estimate of a log fold-change between the given cluster and all others. To account for the fact that multiple experiments came from the same individual, a random effect was fit with duplicate Correlation( ) for individuals in limma[99]. Multiple-testing correction was performed using the Benjamini-Hochberg method with a false discovery rate of 0.01. Only genes with a positive log fold-change that were expressed in at least 30% of nuclei from a given cluster were considered markers of that cluster. Overall, tens to hundreds of genes were found to significantly discriminate each cluster. Cell types were named by examination of these genes and manual searching of the literature.

Training Set Size

As the number of manually annotated images used to train the deep learning model (with 30, 60, 116, 250, or 500 images for training) was increased, it was observed that the model's accuracy increased markedly as new training examples were added until approximately 100 images were used for training. Subsequently, the model continued improving with additional training examples, but at a much slower rate (FIG. 17).

Inter-Rater Reliability

The agreement between two annotators was first directly compared in terms of accuracy metrics for pixels belonging to the ascending and descending aorta. In 116 images, the mean Cohen's kappa was 0.95 in the ascending aorta and 0.92 in the descending aorta.

A deep learning model was then trained on one of the annotator's annotations, using the same architecture and hyperparameters as described above. Both models were applied to 4.7 million images in the UK Biobank and then computed Cohen's kappa on the deep learning output of both models. Interestingly, it was noted that the agreement of the model output for ascending aorta (Cohen's kappa 0.97) and descending aorta (Cohen's kappa 0.94) was higher than observed for the manual annotations. Other correlation coefficients such as Sorensen-Dice coefficient, Count agreement, Pearson correlation coefficient, Spearman's rank correlation coefficient, and ordinary least squares correlation were also used in the 116 manual images for training and 4.7 million images for deep learning model (FIG. 23).

Comparison of Ascending and Descending Aortic Diameter

After conditioning out the effects of participant sex, the descending aortic diameter explained 18% of the variance in the ascending aortic diameter in the 39,260 participants with both measurements. In this population, the ascending aortic diameter could be approximated with the following formula based on the regression output (units in centimeters): 1.25+0.78 (descending aortic diameter)+0.08 (male sex). The 95% confidence interval for the coefficient of the descending aortic diameter in predicting the ascending aortic diameter was 0.77-0.80 (F test P=$2.3\cdot10^{-2,090}$ against the alternative hypothesis of the ascending and descending aortic diameters being uncorrelated). The relationship between the ascending and descending aorta for each of these individuals is plotted in FIG. 8.

It was sought to understand whether the dispersion of the diameter of the ascending aorta was similar to that of the descending aorta in this population. The variance of the ascending and descending aortic diameters was first compared in sex-stratified fashion. The variance in ascending aortic diameter was greater than that of the descending aorta in 20,504 women (0.095 $cm^2$ vs 0.032 $cm^2$; P=$1.3\cdot10^{-1,240}$ against the alternative hypothesis that the variances were equal by the F-test) and in 18,756 men (0.114 $cm^2$ vs 0.042 $cm^2$; P=$2.0\cdot10^{-977}$).

Testing was then performed for equality of the sex-stratified coefficients of variation (standard deviation divided by mean), which is a dimensionless metric that permits comparison between values with different means. In women, the coefficient of variation was greater for the ascending aorta (0.101 for ascending vs 0.079 for descending; $P=1.7 \cdot 10^{-283}$ against the alternative hypothesis that the coefficients of variation were equal). In men, the coefficient of variation was 0.102 for ascending and 0.081 for descending aorta; $P=1.8 \cdot 10^{-216}$.

Repeated Measures

Some individuals in the UK Biobank have undergone imaging more than once: "instance 2" is defined in the UK Biobank as the first imaging visit, and "instance 3" is the second imaging visit. 298,000 images obtained at "instance 3" were identified from 2,976 participants who had undergone a second imaging visit. Of these, 2,731 individuals had data from both imaging visits that passed the quality control procedure described in the Online Methods (2,491 with acceptable ascending aorta measurements and 2,615 with acceptable descending aorta measurements, of whom 2,375 overlapped). On average, the repeated imaging was obtained 2.3 years after the first imaging (SD=0.12 years; 95% CI 2.0-2.5 years). The average age at the time of the first imaging visit was 63.5 years.

Given the short follow-up time, agreement in aortic diameter measurements between the two imaging visits were considered to serve largely as a quality control measure, representing the ability of the model to generate reproducible measurements for each person from images obtained at different times.

The ascending aortic diameter at the first visit explained 94.8% of the variance in ascending aortic diameter at the repeat visit in the 2,491 participants with ascending measurements at both times. On average, the ascending aortic diameter was 0.14 millimeters larger at the repeat visit, consistent with an average increase of 0.06 millimeters per year. There was slight evidence for reversion to the mean, which was considered to be an indicator of measurement error: for every millimeter greater than the average ascending aortic diameter at the first visit, the repeated measurement was predicted to be 0.02 millimeters smaller at the repeat visit (model $r^2=0.01$).

The descending aortic diameter at the first visit explained 88.5% of the variance in descending aortic diameter at the repeat visit in the 2,615 participants with descending measurements at both times. On average, the descending aortic diameter was 0.13 millimeters larger at the repeat visit, consistent with an average increase of 0.06 millimeters per year. There was slight evidence for reversion to the mean: for every millimeter greater than the average descending aortic diameter at the first visit, the repeated measurement was predicted to be 0.05 millimeters smaller at the repeat visit (model $r^2=0.02$).

European GWAS

As a sensitivity analysis, the GWAS was repeated on a subset of participants who were considered strictly European (see above). The European ascending aortic diameter GWAS was conducted in 33,637 participants and the descending GWAS in 34,532 participants, both of which are 87% of the sample size of the primary GWAS. The European ascending aortic GWAS identified 67 loci (82% as many as the primary GWAS) and the descending GWAS identified 36 (78% as many as the primary).

REFERENCES

1. Benjamin Emelia J. et al. Heart Disease and Stroke Statistics-2019 Update: A Report From the American Heart Association. *Circulation* 139, e56-e528 (2019).

2. Isselbacher, E. M. Thoracic and abdominal aortic aneurysms. *Circulation* 111, 816-828 (2005).
3. Owens, D. K. et al. Screening for Abdominal Aortic Aneurysm: US Preventive Services Task Force Recommendation Statement. *JAMA* 322, 2211-2218 (2019).
4. Fann, J. I. Descending thoracic and thoracoabdominal aortic aneurysms. *Coron. Artery Dis.* 13, 93-102 (2002).
5. Guo, D.-C., Papke, C. L., He, R. & Milewicz, D. M. Pathogenesis of thoracic and abdominal aortic aneurysms. *Ann. N. Y. Acad. Sci.* 1085, 339-352 (2006).
6. Vapnik, J. S. et al. Characteristics and Outcomes of Ascending Versus Descending Thoracic Aortic Aneurysms. *Am. J. Cardiol.* 117, 1683-1690 (2016).
7. Jondeau, G. & Boileau, C. Familial thoracic aortic aneurysms. *Curr. Opin. Cardiol.* 29, 492-498 (2014).
8. Pinard Annelie, Jones Gregory T. & Milewicz Dianna M. Genetics of Thoracic and Abdominal Aortic Diseases. *Circ. Res.* 124, 588-606 (2019).
9. Verstraeten, A., Luyckx, I. & Loeys, B. Aetiology and management of hereditary aortopathy. *Nat. Rev.* Cardiol. 14, 197-208 (2017).
10. Lindsay, M. E. & Dietz, H. C. Lessons on the pathogenesis of aneurysm from heritable conditions. *Nature* 473, 308-316 (2011).
11. Majesky, M. W. Developmental basis of vascular smooth muscle diversity. *Arterioscler. Thromb. Vasc. Biol.* 27, 1248-1258 (2007).
12. Hagan, P. G. et al. The International Registry of Acute Aortic Dissection (RAD): new insights into an old disease. *JAMA* 283, 897-903 (2000).
13. Howard, J. & Gugger, S. fastai: A Layered API for Deep Learning. *ArXiv200204688 Cs Stat* (2020).
14. Ronneberger, O., Fischer, P. & Brox, T. U-Net: Convolutional Networks for Biomedical Image Segmentation. *ArXiv150504597 Cs* (2015).
15. Deng, J. et al. ImageNet: A large-scale hierarchical image database. in 2009 *IEEE Conference on Computer Vision and Pattern Recognition* 248-255 (2009). doi: 10.1109/CVPR.2009.5206848.
16. Rosenfeld, A. & Pfaltz, J. L. Sequential Operations in Digital Picture Processing. *J. ACM JACM* 13, 471-494 (1966).
17. Turkbey, E. B. et al. Determinants and Normal Values of Ascending Aortic Diameter by Age, Gender and Race/Ethnicity in the Multi-Ethnic Study of Atherosclerosis (MESA). *J. Magn. Reson. Imaging JMRI* 39, 360-368 (2014).
18. Kaplan, S. et al. Prevalence of an increased ascending and descending thoracic aorta diameter diagnosed by multislice cardiac computed tomography in men versus women and in persons aged 23 to 50 years, 51 to 65 years, 66 to 80 years, and 81 to 88 years. *Am. J. Cardiol.* 100, 1598-1599 (2007).
19. Campens, L. et al. Reference Values for Echocardiographic Assessment of the Diameter of the Aortic Root and Ascending Aorta Spanning All Age Categories. *Am. J. Cardiol.* 114, 914-920 (2014).
20. Wu, P. et al. Mapping ICD-10 and ICD-10-CM Codes to Phecodes: Workflow Development and Initial Evaluation. *JMIR Med. Inform.* 7, e14325 (2019).
21. Bradley, T. J., Bowdin, S. C., Morel, C. F. J. & Pyeritz, R. E. The Expanding Clinical Spectrum of Extracardiovascular and Cardiovascular Manifestations of Heritable Thoracic Aortic Aneurysm and Dissection. *Can. J. Cardiol.* 32, 86-99 (2016).
22. Avdic Tarik et al. Reduced Long-Term Risk of Aortic Aneurysm and Aortic Dissection Among Individuals With Type 2 Diabetes Mellitus: A Nationwide Observational Study. *J. Am. Heart Assoc.* 7, e007618.

23. Prakash Siddharth K., Pedroza Claudia, Khalil Yameen A. & Milewicz Dianna M. Diabetes and Reduced Risk for Thoracic Aortic Aneurysms and Dissections: A Nationwide Case-Control Study. *J. Am. Heart Assoc.* 1, e000323.

24. Bulik-Sullivan, B. K. et al. L D Score regression distinguishes confounding from polygenicity in genome-wide association studies. *Nat. Genet.* 47, 291-295 (2015).

25. Guo, D. et al. Genetic Variants in LRP1 and ULK4 Are Associated with Acute Aortic Dissections. *Am. J. Hum. Genet.* 99, 762-769 (2016).

26. van't Hof, F. N. G. et al. Shared Genetic Risk Factors of Intracranial, Abdominal, and Thoracic Aneurysms. *J. Am. Heart Assoc.* 5, (2016).

27. LeMaire, S. A. et al. Genome-wide association study identifies a susceptibility locus for thoracic aortic aneurysms and aortic dissections spanning FBN1 at 15q21.1. *Nat. Genet.* 43, 996-1000 (2011).

28. Vasan, R. S. et al. Genetic variants associated with cardiac structure and function: a meta-analysis and replication of genome-wide association data. *JAMA* 302, 168-178 (2009).

29. Wild, P. S. et al. Large-scale genome-wide analysis identifies genetic variants associated with cardiac structure and function. *J. Clin. Invest.* 127, 1798-1812 (2017).

30. Is, R. et al. Distribution, Determinants, and Normal Reference Values of Thoracic and Abdominal Aortic Diameters by Computed Tomography (From the Framingham Heart Study). *Am. J. Cardiol.* (2013) doi:10.1016/j.amjcard.2013.01.306.

31. Qazi, S. et al. Increased Aortic Diameters on Multidetector Computed Tomographic Scan Are Independent Predictors of Incident Adverse Cardiovascular Events: The Framingham Heart Study. *Circ. Cardiovasc. Imaging* 10, (2017).

32. Loh, P.-R. et al. Efficient Bayesian mixed-model analysis increases association power in large cohorts. *Nat. Genet.* 47, 284-290 (2015).

33. Loh, P.-R., Kichaev, G., Gazal, S., Schoech, A. P. & Price, A. L. Mixed model association for biobank-scale data sets. *Nat. Genet.* 50, 906-908 (2018).

34. Abbott, L., Neale, B. & Palmer, D. Genetic correlation between traits and disorders in the UK Biobank. https://ukbb-rg.hail.is/ (2019).

35. Bulik-Sullivan, B. et al. An atlas of genetic correlations across human diseases and traits. *Nat. Genet.* 47, 1236-1241 (2015).

36. Wain, L. V. et al. Novel Blood Pressure Locus and Gene Discovery Using Genome-*Wide* Association Study and Expression Data Sets From Blood and the Kidney. *Hypertens. Dallas Tex* 1979 (2017) doi:10.1161/HYPERTENSIONAHA.117.09438.

37. Gusev, A. et al. Integrative approaches for large-scale transcriptome-wide association studies. *Nat. Genet.* 48, 245-252 (2016).

38. Lonsdale, J. et al. The Genotype-Tissue Expression (GTEx) project. *Nat. Genet.* 45, 580-585 (2013).

39. Tsutsui, K. et al. ADAMTSL-6 is a novel extracellular matrix protein that binds to fibrillin-1 and promotes fibrillin-1 fibril formation. *J. Biol. Chem.* 285, 4870-4882 (2010).

40. Chou, C.-K. et al. The Regulations of Deubiquitinase USP15 and Its Pathophysiological Mechanisms in Diseases. *Int. J. Mol. Sci.* 18, (2017).

41. Eichhorn, P. J. A. et al. USP15 stabilizes TGF-β receptor I and promotes oncogenesis through the activation of TGF-β signaling in glioblastoma. *Nat. Med.* 18, 429-435 (2012).

42. Finucane, H. K. et al. Heritability enrichment of specifically expressed genes identifies disease-relevant tissues and cell types. *Nat. Genet.* 50, 621-629 (2018).

43. Bhuwania, R. et al. Supervillin couples myosin-dependent contractility to podosomes and enables their turnover. *J. Cell Sci.* 125, 2300-2314 (2012).

44. Linder, S., Wiesner, C. & Himmel, M. Degrading Devices: Invadosomes in Proteolytic Cell Invasion. *Annu. Rev. Cell Dev. Biol.* 27, 185-211 (2011).

45. Elbitar, S. et al. Pathogenic variants in THSD4, encoding the ADAMTS-like 6 protein, predispose to inherited thoracic aortic aneurysm. *Genet. Med.* 1-12 (2020) doi: 10.1038/s41436-020-00947-4.

46. Maddika, S. et al. WWP2 is an E3 ubiquitin ligase for PTEN. *Nat. Cell Biol.* 13, 728-733 (2011).

47. Chen, H. et al. WWP2 regulates pathological cardiac fibrosis by modulating SMAD2 signaling. *Nat. Commun.* 10, 1-19 (2019).

48. Pirruccello, J. P. et al. Analysis of cardiac magnetic resonance imaging traits in 29,000 individuals reveals shared genetic basis with dilated cardiomyopathy. *bioRxiv* 2020.02.12.946038 (2020) doi:10.1101/2020.02.12.946038.

49. Teslovich, T. M. et al. Biological, clinical and population relevance of 95 loci for blood lipids. *Nature* 466, (2010).

50. Renard, M. et al. Clinical Validity of Genes for Heritable Thoracic Aortic Aneurysm and Dissection. *J. Am. Coll. Cardiol.* 72, 605-615 (2018).

51. Dietz, H. C. et al. Marfan syndrome caused by a recurrent de novo missense mutation in the fibrillin gene. *Nature* 352, 337-339 (1991).

52. Falak, S. et al. Protease inhibitor 15, a candidate gene for abdominal aortic internal elastic lamina ruptures in the rat. *Physiol. Genomics* 46, 418-428 (2014).

53. Parrott, A. et al. Cantu syndrome: A longitudinal review of vascular findings in three individuals. *Am. J. Med. Genet. A.* 182, 1243-1248 (2020).

54. Heuzé, M. L. et al. ASB2 targets filamins A and B to proteasomal degradation. *Blood* 112, 5130-5140 (2008).

55. de Leeuw, C. A., Mooij, J. M., Heskes, T. & Posthuma, D. MAGMA: Generalized Gene-Set Analysis of GWAS Data. *PLoS Comput. Biol.* 11, (2015).

56. Sudlow, C. et al. UK biobank: an open access resource for identifying the causes of a wide range of complex diseases of middle and old age. *PLoS Med.* 12, e1001779 (2015).

57. Petersen, S. E. et al. Imaging in population science: cardiovascular magnetic resonance in 100,000 participants of UK Biobank—rationale, challenges and approaches. *J. Cardiovasc. Magn. Reson.* 15, 46 (2013).

58. Petersen, S. E. et al. UK Biobank's cardiovascular magnetic resonance protocol. *J. Cardiovasc. Magn. Reson.* 18, (2016).

59. He, K., Zhang, X., Ren, S. & Sun, J. Deep Residual Learning for Image Recognition. *ArXiv*151203385 *Cs* (2015).

60. Krizhevsky, A., Sutskever, I. & Hinton, G. E. ImageNet Classification with Deep Convolutional Neural Networks.

61. Kingma, D. P. & Ba, J. Adam: A Method for Stochastic Optimization. *ArXiv*14126980 *Cs* (2017).

62. Smith, L. N. Cyclical Learning Rates for Training Neural Networks. *ArXiv*150601186 *Cs* (2015).

63. He, K., Zhang, X., Ren, S. & Sun, J. Spatial Pyramid Pooling in Deep Convolutional Networks for Visual Recognition. *ArXiv*14064729 *Cs* 8691, 346-361 (2014).

64. Gugger, S. fastai/course-v3. GitHub https://github.com/fastai/course-v3 (2019).

65. McHugh, M. L. Interrater reliability: the kappa statistic. *Biochem. Medica* 22, 276-282 (2012).

66. Horn, B. *Robot vision*. (MIT Press; McGraw-Hill, 1986).

67. Marwick, B. & Krishnamoorthy, K. *benmarwick/cvequality*. (2019).

68. Bycroft, C. et al. The UK Biobank resource with deep phenotyping and genomic data. *Nature* 562, 203 (2018).

69. Yang, J. et al. FTO genotype is associated with phenotypic variability of body mass index. *Nature* 490, 267-272 (2012).

70. Chang, C. C. et al. Second-generation PLINK: rising to the challenge of larger and richer datasets. *GigaScience* 4, (2015).

71. Bellenguez, C. et al. A robust clustering algorithm for identifying problematic samples in genome-wide association studies. *Bioinforma. Oxf. Engl.* 28, 134-135 (2012).

72. Benjamin, E. J. et al. Variants in ZFHX3 are associated with atrial fibrillation in individuals of European ancestry. *Nat. Genet.* 41, 879-881 (2009).

73. Hong, H. et al. Assessing batch effects of genotype calling algorithm BRLMM for the Affymetrix GeneChip Human Mapping 500 K array set using 270 HapMap samples. *BMC Bioinformatics* 9, S17 (2008).

74. Das, S. et al. Next-generation genotype imputation service and methods. *Nat. Genet.* 48, 75. Pers, T. H., Timshel, P. & Hirschhorn, J. N. SNPsnap: a Web-based tool for identification and annotation of matched SNPs. *Bioinformatics* 31, 418-420 (2015).

76. Gamazon, E. R. et al. A gene-based association method for mapping traits using reference transcriptome data. *Nat. Genet.* 47, 1091-1098 (2015).

77. Gusev, A. et al. Transcriptome-wide association study of schizophrenia and chromatin activity yields mechanistic disease insights. *Nat. Genet.* 50, 538-548 (2018).

78. Zhu, Z. et al. Integration of summary data from GWAS and eQTL studies predicts complex trait gene targets. *Nat. Genet.* 48, 481-487 (2016).

79. de Leeuw, C. A., Neale, B. M., Heskes, T. & Posthuma, D. The statistical properties of gene-set analysis. *Nat. Rev. Genet.* 17, 353-364 (2016).

80. Liberzon, A. et al. Molecular signatures database (MSigDB) 3.0. *Bioinformatics* 27, 1739-1740 (2011).

81. Segrè, A. V. et al. Common Inherited Variation in Mitochondrial Genes Is Not Enriched for Associations with Type 2 Diabetes or Related Glycemic Traits. *PLOS Genet.* 6, e1001058 (2010).

82. Hout, C. V. V. et al. Whole exome sequencing and characterization of coding variation in 49,960 individuals in the UK Biobank. *bioRxiv* 572347 (2019) doi:10.1101/572347.

83. Regier, A. A. et al. Functional equivalence of genome sequencing analysis pipelines enables harmonized variant calling across human genetics projects. *Nat. Commun.* 9, 4038 (2018).

84. Van der Auwera, G. A. et al. From FastQ data to high confidence variant calls: the Genome Analysis Toolkit best practices pipeline. *Curr. Protoc. Bioinforma.* 43, 11.10.1-33 (2013).

85. McLaren, W. et al. The Ensembl Variant Effect Predictor. *Genome Biol.* 17, 122 (2016).

86. Karczewski, K. J. et al. Variation across 141,456 human exomes and genomes reveals the spectrum of loss-offunction intolerance across human protein-coding genes. *bioRxiv* 531210 (2019) doi:10.1101/531210.

87. Haas, M. E. et al. Genetic Association of Albuminuria with Cardiometabolic Disease and Blood Pressure. *Am. J. Hum. Genet.* 103, 461-473 (2018).

88. Kent, K. C. et al. Analysis of risk factors for abdominal aortic aneurysm in a cohort of more than 3 million individuals. *J. Vasc. Surg.* 52, 539-548 (2010).

89. Kechin, A., Boyarskikh, U., Kel, A. & Filipenko, M. cutPrimers: A New Tool for Accurate Cutting of Primers from Reads of Targeted Next Generation Sequencing. *J. Comput. Biol. J. Comput. Mol. Cell Biol.* 24, 1138-1143 (2017).

90. McInnes, L., Healy, J. & Melville, J. UMAP: Uniform Manifold Approximation and Projection for Dimension Reduction. *ArXiv*180203426 *Cs Stat* (2018).

91. Fleming, S. J., Marioni, J. C. & Babadi, M. CellBender remove-background: a deep generative model for unsupervised removal of background noise from scRNA-seq datasets. *bioRxiv* 791699 (2019) doi:10.1101/791699.

92. Wolock, S. L., Lopez, R. & Klein, A. M. Scrublet: Computational Identification of Cell Doublets in Single-Cell Transcriptomic Data. *Cell Syst.* 8, 281-291.e9 (2019).

93. Lopez, R., Regier, J., Cole, M. B., Jordan, M. I. & Yosef, N. Deep generative modeling for single-cell transcriptomics. *Nat. Methods* 15, 1053-1058 (2018).

94. Stuart, T. et al. Comprehensive Integration of Single-Cell Data. *Cell* 177, 1888-1902.e21 (2019).

95. Wolf, F. A., Angerer, P. & Theis, F. J. SCANPY: large-scale single-cell gene expression data analysis. *Genome Biol.* 19, 15 (2018).

96. Ritchie, M. E. et al. limma powers differential expression analyses for RNA-sequencing and microarray studies. *Nucleic Acids Res.* 43, e47 (2015).

97. Lun, A. T. L. & Marioni, J. C. Overcoming confounding plate effects in differential expression analyses of single-cell RNA-seq data. *Biostat. Oxf. Engl.* 18, 451-464 (2017).

98. Love, M. I., Huber, W. & Anders, S. Moderated estimation of fold change and dispersion for RNA-seq data with DESeq2. *Genome Biol.* 15, 550 (2014).

99. Smyth, G. K., Michaud, J. & Scott, H. S. Use of within-array replicate spots for assessing differential expression in microarray experiments. *Bioinforma. Oxf. Engl.* 21, 2067-2075 (2005).

EQUIVALENTS AND SCOPE, INCORPORATION BY REFERENCE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize or be able to ascertain using no more than routine experimentation, many equivalents to the specific embodiments of the invention described here. Such equivalents are intended to be encompassed by the following claims.

All references, including patent documents, are incorporated by reference in their entirety.

What is claimed is:

1. A method for assessing a human subject's risk for an aneurysm of the ascending thoracic aorta, comprising:

detecting, in a sample from the human subject, a G allele at single nucleotide polymorphism (SNP) rs1441358 in;

determining that the human subject is at increased risk for the aneurysm of the ascending thoracic aorta based on the detection; and administering to the human subject a treatment to reduce the risk for the aneurysm of the ascending thoracic aorta, the treatment comprising a medication, a surgery, or both.

2. The method of claim 1, further comprising:

detecting, in the sample, an allele at SNP rs9847006 in ULK4;

calculating a polygenic score based on the number of SNPs detected the G allele at the SNP rs1441358 in THSD4 and the detected allele at the SNP rs9847006 in ULK4, wherein detection of a T allele at the SNP rs9847006 in ULK4 increases the polygenic score; and determining that the human subject is at a further increased risk for the aneurysm of the ascending thoracic aorta when the polygenic score is greater than a reference polygenic score calculated from a population of subjects who do not have thoracic aortic aneurysms.

3. The method of claim 2, further comprising administering thoracic imaging to the human subject when the polygenic score is greater than the reference polygenic score.

4. The method of claim 1, further comprising assessing an aortic diameter of the human subject relative to a mean reference aortic diameter.

5. The method of claim 4, wherein the aortic diameter is determined by computed tomography (CT), magnetic resonance imaging (MRI), or echocardiography.

6. The method of claim 1, wherein;

the medication is selected from the group consisting of: aspirin, blood pressure medications, and statins; and the surgery is open surgical repair or endovascular aneurysm repair.

7. The method of claim 1, further comprising:

detecting, in the sample, an allele at SNP rs56298756 in USP15;

calculating a polygenic score based on the G allele at the SNP rs1441358 in THSD4 and the detected allele at the SNP rs56298756 in USP15, wherein detection of a T allele at the SNP rs56298756 in USP15 increases the polygenic score; and determining that the human subject is at a further increased risk for the aneurysm of the ascending thoracic aorta when the polygenic score is greater than a reference polygenic score calculated from a population of subjects who do not have thoracic aortic aneurysms.

8. The method of claim 7, further comprising administering thoracic imaging to the human subject when the polygenic score is greater than the reference polygenic score.

9. The method of claim 1, further comprising:

detecting, in the sample, alleles at each of SNP rs9847006 in ULK4, SNP rs56298756 in USP15, SNP rs2118181 in FBN1, SNP rs62053262 in WWP2, and SNP rs6974735 in ELN;

calculating a polygenic score based on the G allele at the SNP rs1441358 in THSD4 and the detected alleles, wherein the polygenic score is increased by detection of a T allele at the SNP rs9847006 in ULK4, a T allele at the SNP rs56298756 in USP15, a C allele at the SNP rs2118181 in FBN1, a C allele at the SNP rs62053262 in WWP2, and an A allele at the SNP rs6974735 in ELN; and determining that the human subject is at a further increased risk for the aneurysm of the ascending thoracic aorta when the polygenic score is greater than a reference polygenic score calculated from a population of subjects who do not have thoracic aortic aneurysms.

* * * * *